(12) United States Patent
Goodman et al.

(10) Patent No.: US 11,549,115 B2
(45) Date of Patent: Jan. 10, 2023

(54) COMPOSITIONS AND METHODS FOR REGULATED GENE EXPRESSION

(71) Applicant: YALE UNIVERSITY, New Haven, CT (US)

(72) Inventors: Andrew Goodman, Guilford, CT (US); Bentley Lim, New Haven, CT (US); Natasha Barry, Shelton, CT (US)

(73) Assignee: Yale University, New Haven, CT (US)

( * ) Notice: Subject to any disclaimer, the term of this patent is extended or adjusted under 35 U.S.C. 154(b) by 447 days.

(21) Appl. No.: 16/606,278

(22) PCT Filed: Apr. 18, 2018

(86) PCT No.: PCT/US2018/028056
§ 371 (c)(1),
(2) Date: Oct. 18, 2019

(87) PCT Pub. No.: WO2018/195136
PCT Pub. Date: Oct. 25, 2018

(65) Prior Publication Data
US 2021/0115455 A1    Apr. 22, 2021

Related U.S. Application Data

(60) Provisional application No. 62/486,526, filed on Apr. 18, 2017.

(51) Int. Cl.
*C12N 15/63* (2006.01)
*C12N 15/74* (2006.01)

(52) U.S. Cl.
CPC ........... *C12N 15/635* (2013.01); *C12N 15/74* (2013.01)

(58) Field of Classification Search
CPC ...... C12N 15/635; C12N 15/74; C12N 15/01; C12N 15/102; C07K 14/195
See application file for complete search history.

(56) References Cited

U.S. PATENT DOCUMENTS

2015/0004705 A1    1/2015 Lu

FOREIGN PATENT DOCUMENTS

WO    WO 2016-201174 A2 * 12/2016

OTHER PUBLICATIONS

Rodriguez-Garcia et al. Natural and synthetic tetracycline-inducible promoters for use in the antibiotic-producing bacteria. Nucleic Acids Research, 2005, 33(9), e87, 1-8.*
Accetto, T. et al., 2011, "Inability of Prevotella bryantii to form a functional Shine-Dalgarno interaction reflects unique evolution of ribosome binding sites in Bacteroidetes," PLoS ONE, 6:e22914-e22919.
Altschul, S.F. et al., 1990, "Basic local alignment search tool," Journal of Molecular Biology 215:403-410.
Bayley, D.P. et al., 2000, "Analysis of cepA and other Bacteroides fragilis genes reveals a unique promoter structure," FEMS Microbiol. Lett., 193:149-154.
Bertram, R. et al. 2008, "The application of Tet repressor in prokaryotic gene regulation and expression," Microbial Biotechnology, 1:2-16.
Bohl, D. et al., 1998, "Control of erythropoietin delivery by doxycycline in mice after intramuscular injection of adeno-associated vector," Blood, 92:1512-1517.
Bremer et al., 2008, "Modulation of Chemical Composition and Other Parameters of the Cell at Different Exponential Growth Rates," EcoSal Plus, 3:1-49.
Bryksin, A.V. et al., 2010, "Overlap extension PCR cloning: a simple and reliable way to create recombinant plasmids," Biotech., 48:463-465.
Caporaso, J.G. et al., 2010, "QIIME allows analysis of high-throughput community sequencing data," Nat. Meth., 7:335-336.
Cetin, M. et al., 2011, "Preparation and characterization of metformin hydrochloride loaded-Eudragit®RSPO and Eudragit®RSPO/PLGA nanoparticles," Pharmaceutical Development and Technology, 18:570-576.
Chatzidaki-Livanis, M. et al., 2016, "Bacteroides fragilis type VI secretion systems use novel effector and immunity proteins to antagonize human gut Bacteroidales species," Proceedings of the National Academy of Sciences, 113:3627-3632.
Crooks, G.E. et al., 2004, "WebLogo: a sequence logo generator," Genome Research, 14:1188-1190.
Cullen, T.W. et al., 2015, "Gut microbiota. Antimicrobial peptide resistance mediates resilience of prominent gut commensals during inflammation," Science, 347:170-175.
Dereeper, A. et al., 2008, "Phylogeny.fr: robust phylogenetic analysis for the non-specialist," Nucleic Acids Research, 36:W465-W469.
Dereeper, A. et al., 2010, "BLAST-Explorer helps you building datasets for phylogenetic analysis," BMC Evol. Biol., 10:8.
Faith, J.J., et al., 2013, "The long-term stability of the human gut microbiota," Science, 341:1237439-1237439.
Goodman, A.L. et al., 2009, "Identifying genetic determinants needed to establish a human gut symbiont in its habitat," Cell Host and Microbe, 6:279-289.
Goodman, A.L. et al., 2011, "Identifying microbial fitness determinants by insertion sequencing using genome-wide transposon mutant libraries," Nat. Protoc., 6:1969-1980.
Gourse, R.L. et al., 2000, "UPs and downs in bacterial transcription initiation: the role of the alpha subunit of RNA polymerase in promoter recognition," Mol. Microbiol., 37:687-695.
Hall, M.P. et al., 2012, "Engineered luciferase reporter from a deep sea shrimp utilizing a novel imidazopyrazinone substrate," ACS Chem. Biol., 7:1848-1857.
Hamady, Z.Z.R. et al., 2008, "Identification and use of the putative Bacteroides ovatus xylanase promoter for the inducible production of recombinant human proteins," Microbiology, 154:3165-3174.

(Continued)

*Primary Examiner* — Iqbal H Chowdhury
(74) *Attorney, Agent, or Firm* — Riverside Law LLP

(57) ABSTRACT

The present invention provides compositions and methods for regulated gene expression. In certain aspects, the invention relates to an inducible synthetic promoter that can be used for regulated gene expression or to generate mutations in one or more bacterial cells of the gut microbiota.

13 Claims, 19 Drawing Sheets
Specification includes a Sequence Listing.

(56) References Cited

OTHER PUBLICATIONS

Helbl, V. et al., 1998, "Stepwise selection of TetR variants recognizing tet operator 4C with high affinity and specificity," Journal of Molecular Biology, 276:313-318.
Helbl, V. et al., 1998, "Stepwise selection of TetR variants recognizing tet operator 6C with high affinity and specificity," Journal of Molecular Biology, 276:319-324.
Henssler, E.-M. et al., 2004, "Structure-based design of Tet repressor to optimize a new inducer specificity," Biochemistry, 43:9512-9518.
Hillen, W. et al., 1994, "Mechanisms underlying expression of Tn10 encoded tetracycline resistance," Annu. Rev. Microbiol., 48:345-369.
Hsiao, E.Y., et al., 2013, "Microbiota modulate behavioral and physiological abnormalities associated with neurodevelopmental disorders," Cell, 155:1451-1463.
Kamionka, A. et al., 2004, "Two mutations in the tetracycline repressor change the inducer anhydrotetracycline to a corepressor," Nucleic Acids Research, 32:842-847.
Koropatkin, N.M. et al., 2008, "Starch catabolism by a prominent human gut symbiont is directed by the recognition of amylose helices," Structure, 16:1105-1115.
Kotula, J.W. et al., 2014, "Programmable bacteria detect and record an environmental signal in the mammalian gut," Proceedings of the National Academy of Sciences, 111:4838-4843.
Krueger, M. et al., 2007, "Engineered Tet repressors with recognition specificity for the tetO-4C5G operator variant," Gene, 404:93-100.
Larsbrink, J. et al., 2014, "A discrete genetic locus confers xyloglucan metabolism in select human gut Bacteroidetes," Nature, 506:498-502.
Lim, B et al., "Engineered Regulatory Systems Modulate Gene Expression of Human Commensals in the Gut", Cell. Apr. 20, 2017, vol. 169, pp. 547-558.
Lutz, R. et al., 1997, "Independent and tight regulation of transcriptional units in *Escherichia coli* via the LacR/O, the TetR/O and AraC/I1-I2 regulatory elements," Nucleic Acids Research, 25:1203-1210.
Manfredsson, F.P. et al., 2009, "Tight Long-term dynamic doxycycline responsive nigrostriatal GDNF using a single rAAV vector," Molecular Therapy, 17:1857-1867.
Martens, E.C. et al., 2008, "Mucosal glycan foraging enhances fitness and transmission of a saccharolytic human gut bacterial symbiont," Cell Host and Microbe, 4:447-457.
Mastropaolo, Md et al., "Comparison of Bacteroides thetaiotaomicron and *Escherichia coli* 16S rRNA Gene Expression Signals", Microbiology. 2009, vol. 155, pp. 2683-2693.
McDonald, N.D. et al., 2016, "Host-Derived Sialic Acids are an Important Nutrient Source Required for Optimal Bacterial Fitness In Vivo," mBio, 7:e02237-15.
Mimee, M. et al., 2015, "Programming a Human Commensal Bacterium, Bacteroides thetaiotaomicron, to Sense and Respond to Stimuli in the Murine Gut Microbiota," Cell Syst., 1:62-71.
Ng, K.M., et al., 2013, "Microbiota-liberated host sugars facilitate post-antibiotic expansion of enteric pathogens," Nature, 502:96-99.
Parker, A.C. et al., 2012, "Development of an IPTG inducible expression vector adapted for Bacteroides fragilis," Plasmid, 68:86-92.
Rey, FE et al., "Dissecting the in Vivo Metabolic Potential of Two Human Gut Acetogens", The Journal of Biological Chemistry. May 5, 2010, vol. 285, No. 29, pp. 22082-22090.
Rogers, J.K. et al., 2015, "Synthetic biosensors for precise gene control and real-time monitoring of metabolites," Nucleic Acids Research, 43:7648-7660.
Scholz, O. et al., 2003, "Teaching TetR to recognize a new inducer," Journal of Molecular Biology, 329:217-227.
Scholz, O. et al., 2004, "Activity reversal of Tet repressor caused by single amino acid exchanges," Mol. Microbiol., 53:777-789.
Sonnenburg, J.L. et al., 2005, "Glycan foraging in vivo by an intestine-adapted bacterial symbiont," Science, 307:1955-1959.
The Human Microbiome Project Consortium, 2012, "Structure, Function and Diversity of the Healthy Human Microbiome," Nature, 486:207-214.
Wasik, B.R. et al., 2016, "Effects of Sialic Acid Modifications on Virus Binding and Infection," Trends in Microbiology, 24:991-1001.
Wegmann, U. et al., 2013, "Defining the Bacteroides Ribosomal Binding Site," Appl. Environ. Microbiol., 79:1980-1989.
Wexler, A.G. et al., 2016, "Human symbionts inject and neutralize antibacterial toxins to persist in the gut," Proceedings of the National Academy of Sciences, 113:3639-3644.
Wexler, H.M., 2007, "Bacteroides: the Good, the Bad, and the Nitty-Gritty," Clinical Microbiology Reviews, 20:593-621.

* cited by examiner

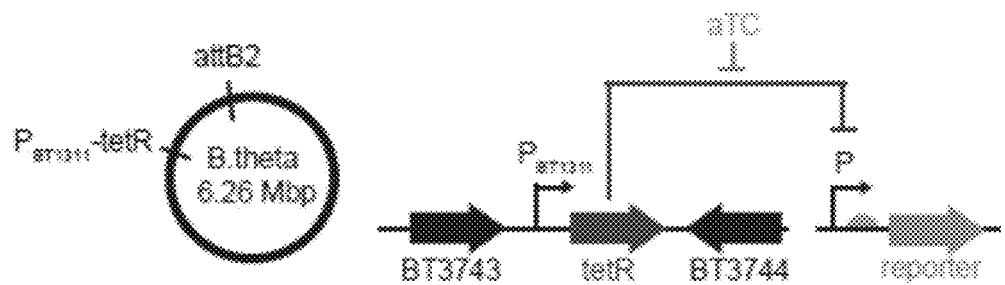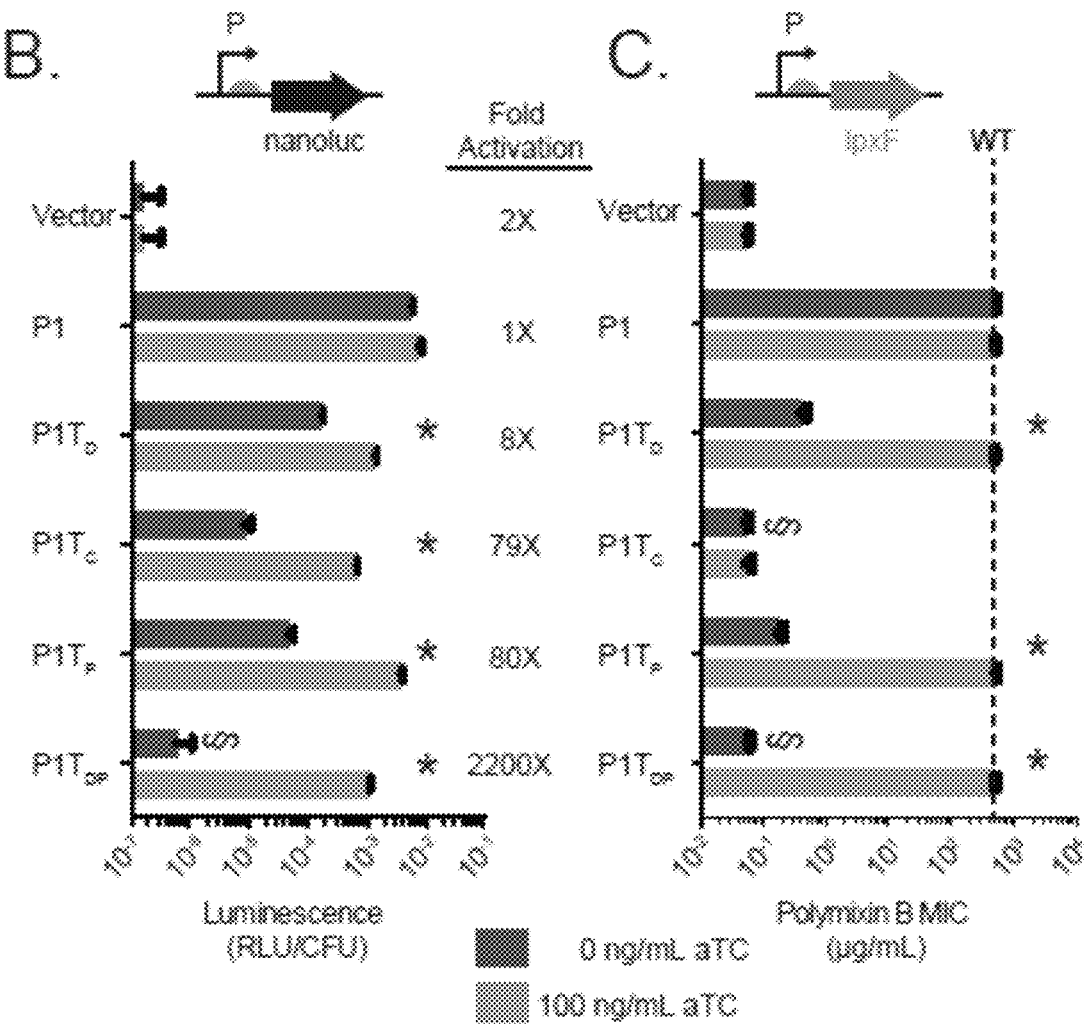
Fig. 2A-2C

SEQUENCE LISTING

<160> NUMBER OF SEQ ID NOS: 101

<210> SEQ ID NO 1
<211> LENGTH: 516
<212> TYPE: DNA
<213> ORGANISM: Artificial sequence
<220> FEATURE:
<223> OTHER INFORMATION: Luciferase reporter (from Promega)

<400> SEQUENCE: 1

```
atggtcttca cactcgaaga tttcgttggg gactggcgac agacagccgg ctacaacctg      60
gaccaagtcc ttgaacaggg aggtgtgtcc agtttgtttc agaatctcgg ggtgtccgta     120
actccgatcc aaaggattgt cctgagcggt gaaaatgggc tgaagatcga catccatgtc     180
```

-continued

```
atcatcccgt atgaaggtct gagcggcgac caaatgggcc agatcgaaaa aatttttaag      240
gtggtgtacc ctgtggatga tcatcacttt aaggtgatcc tgcactatgg cacactggta      300
atcgacgggg ttacgccgaa catgatcgac tatttcggac ggccgtatga aggcatcgcc      360
gtgttcgacg gcaaaaagat cactgtaaca gggaccctgt ggaacggcaa caaaattatc      420
gacgagcgcc tgatcaaccc cgacggctcc ctgctgttcc gagtaaccat caacggagtg      480
accggctggc ggctgtgcga acgcattctg gcgtaa                                516
```

<210> SEQ ID NO 2
<211> LENGTH: 678
<212> TYPE: DNA
<213> ORGANISM: Artificial sequence
<220> FEATURE:
<223> OTHER INFORMATION: BT1854; reporter for growth on polymyxin B

<400> SEQUENCE: 2

```
atgatagaat ttctttcgga tatagacacc caactgcttt tgttcttcaa tggaatacat       60
tcgccttcct gggattactt catgagtgca ttcacaggta aagttatatg ggtcccgatg      120
tatgccagta tcttatatat actgctcaag aatttcatt ggaaagtggc tttgtgctat      180
gtggtagcga tcgccctcac tatcacgttt gccgatcaga tgtgcaatag ttttcttcgt      240
ccgctggtag gtcgcctgcg tccctccaat ccggaaaatc cgatagcgga tttggtctat      300
attgtgaatg aagacgagg aggaggattc ggtttccctt cctgtcatgc tgccaattct      360
ttcggacttg ccatatttct gatttgcctg ttccgtaaac gctggttaag catatttatc      420
gtactttggg catttaccaa ctcttataca cgcctgtacc tgggattgca ttatcccggt      480
gatttagtag caggagccat tatcggtgga ttcggaggtt ggctgttcta ctttatcgcc      540
cacaagttaa cggcacgact tcagtcagac actcctgttc ctggaaaggg tgccggaatg      600
aaacaaacag aagttatgat ctataccgga ttgctgactt tagcaggcat tatcatctat      660
tccatcgtgc aaagttag                                                   678
```

<210> SEQ ID NO 3
<211> LENGTH: 2766
<212> TYPE: DNA
<213> ORGANISM: Artificial sequence
<220> FEATURE:
<223> OTHER INFORMATION: HTCS gene BT1754; reporter for growth in
      fructose

<400> SEQUENCE: 3

```
atgatgagat ggatgaagac gatgagatat ctgaagtgga tgctggtgct gtttggttta       60
atcgggatga cggcttgccg gcaggataca ccccattttc gtattggggt ggctcaatgc      120
agcgatgatt catggcgaca taagatgaat gatgagattc ttcgggaagc aatgttttat      180
aatggcgttt cggtggaaat ccgttcggca ggagatgata acagtaagca ggcggaagat      240
gtccattatt ttatggacga aggagtcgat ctgctgatta tttccgctaa cgaagctgct      300
cctatgactc cgattgtaga agaagcttat cagaaaggca tccccgttat tcttgtagac      360
cggaagattc tttcggataa atatactgcc tatatcggag ccgataatta tgaaatcggt      420
cgttcggtag gaaactatat tgcctccagt ctgaaaggga agggaaatat agtagaactg      480
acaggattga gcggttcgac tcctgcaatg gaacggcatc agggatttat ggctgccatc      540
agtaaattcc cggatataaa gctgattgat aaagcggatc tgcgtgggga acgtggtccg      600
gcagagatag aaatggatag tatgcttcgg aggcatccta agattgatgc tgtgtatgcc      660
```

```
cataatgacc gtatcgctcc gggtgcctat caggcagcaa agatggcagg gcgggagaag    720
gaaatgattt ttgtcggcat agatgccttg ccgggtaagg gaaacggact ggaactggtt    780
ttggacagtg tgctggatgc cacctttatc tatccgacca atggcgataa ggtactgcaa    840
ctggctatgg acattctgga gaagaaaccc tatcccaaag aaacggtgat gaataccgct    900
gttgtggacc gtaccaacgc acacgtcatg cagttgcaga ctacacacat ctccgaactc    960
gataaaaaga ttgaaacgct caacggacgt atcggtggat acctctctca ggtagctaca   1020
caacaggtcg ttttatacgg cagtctgatt atccttttat tggtagccgg cttattattg   1080
gtcgtttata aatcactccg ctctaagaat cgcttgaata aagagctttt taagcagaag   1140
cagcaattgg aagagcagcg tgacaaactg gaagaacagc gtgaccaatt gatacagctc   1200
tctcatcaac tggaagaagc tacccatgcc aagctggtct ttttcaccaa tatttctcac   1260
gacttccgta ctccgttgac attggttgcc gacccggtag aacatttatt ggcggacaag   1320
acattgagtg gagatcagca ccggatgctc atgctgattc agcgaaatgt gaatatcctt   1380
ttgcgcctgg tcaatcagat tttggatttc cgtaaatatg aaaacggcaa gatggaatat   1440
actccggtta cggtggatgt cctttcttct ttcgaaggat ggaatgagtc ttttcaggcg   1500
gcagcccgta agaagcatat ccatttttct tttgatagta tgccggatac ggattatcat   1560
acactggcag acatggagaa gctggaacgt atttatttca atctcctgtc caatgccttt   1620
aagtttacac cggaaaacgg gaaaatagcc atccgtctgt cttcccttag taagaggac    1680
aagcgatgga tacgtttcac ggtggcaaat accggttcca tgatttctgc gaacatatc    1740
cgcaatgtat tcgaccgttt ctataagatt gatatgcacc ataccggttc gggaatcgga   1800
ctggcattgg taaaagcctt cgtagaaatg cacggtggta tgatctccgt agagagcgat   1860
gagaaacagg gcacggtctt taccgttgaa ctgcctgtac agtcttgtga ggctgttgct   1920
gccgaaccgg ataccaccct tgtttctgcg gattcccgta caacagatgt tctattggca   1980
gaagaggaag aactggaaaa aggatatgac tcttccaaac cgtccgtact gattattgat   2040
gataatgagg atatccgttc gtatgtccat acgctgttgc atacagacta tcggtgatt    2100
gaagcggcag acggctccga aggaatccgt aaggctatga gtatgttcc ggacctgatc    2160
atttctgatg tgatgatgcc gggcattgat ggcattgaat gttgccgccg gctgaaaagt   2220
gagttacaga cctgtcatat tccggttatt ctgctgacag cgtgttcact ggacgaacag   2280
cgtattcagg gatatgacgg tggtgcggat tcttatattt caaagccgtt cagttcacag   2340
ctgttgctgg cacgtgtccg caatctgatc gattctcacc gtcgtctgaa acagttcttt   2400
ggtgacgggc agacattggc aaaagaagat gtctgcgata tggacaagga ttttgtagaa   2460
agattcaagt cattgattga agagaaaatg ggagactccg gtttgaatgt ggaggacttg   2520
ggcaaagaca tgggactaag ccgtgtgcag ctttatcgca agattaaatc attgactaac   2580
tactctccga tgaattgct ccgtatcgcc cgtttgaaga aggcagcttc tttgcttgct   2640
tcttcggaca tgaccgtagc ggagattggt tatgaagtcg gtttcagttc accttcttat   2700
ttcgccaagt gctataaaga gcagtttgga gagagcccga cagatttcct gaaaaggaaa   2760
ggatga                                                              2766
```

<210> SEQ ID NO 4
<211> LENGTH: 63
<212> TYPE: DNA
<213> ORGANISM: Artificial sequence
<220> FEATURE:
<223> OTHER INFORMATION: Periplasmic localization signal from BT4676

<400> SEQUENCE: 4

| | |
|---|---|
| atgaagaaaa ttttatcttt gcttgtgatg gctattgtag ctatacagtt ctcatttgcc | 60 |
| ggc | 63 |

<210> SEQ ID NO 5
<211> LENGTH: 927
<212> TYPE: DNA
<213> ORGANISM: Artificial sequence
<220> FEATURE:
<223> OTHER INFORMATION: Periplasmic-localized T6SS effector from B. fragilis NCTC 9343

<400> SEQUENCE: 5

| | |
|---|---|
| atgaagaaaa ttttatcttt gcttgtgatg gctattgtag ctatacagtt ctcatttgcc | 60 |
| ggcggtaagg aaatagaaat aaagaaattg ccagagttcg aggctatggt gaatgccggt | 120 |
| aatacgacct atacgggatt ggtagaaggc atcgggtatg tgtattggac aacagaaacc | 180 |
| ctatatttta tccgcactaa tccagaacaa ttatgggcga ttccaaaata tcagcaaata | 240 |
| cctttcccct atttttcaaag gaaagatgca atcattgaga ccaaaacatt acatacactc | 300 |
| catgtcttgt caaagatgaa actgttgaaa ttggattacg atgcctatta tgcattttat | 360 |
| ggtatcgtgg aggagatgct aaaatttatt catcgggcgg atgctattaa aagttattgt | 420 |
| gaaataccct ttcccataat aaaatccaaa ggagcactaa aggaaatgac gcaagaaat | 480 |
| gggatactat cattaggtag tcaaataaat gaccaaatcg agctcccct tgatgcagcg | 540 |
| aatatgctaa tggataataa acatataggc aaaattggag atggattgtc gcttatttct | 600 |
| attatagatg aggtaggtaa tggtgaatat tggtcagctg ccggagacat tttactgttt | 660 |
| gcagccggaa aaacaaaatt aagtccctat atgactgtca taagtttagg cacatggatg | 720 |
| tatgagacgg acttgatgca atggagatta gcatgtataa attatagcga ttacaaaaaa | 780 |
| acactaataa aatatcgaga attacaaaaa aaatttgaaa gtggagacaa atctgtagag | 840 |
| gaaaagatga atgaatgtca caaaatactg aattcacatt atatagagat gcaaaaaaat | 900 |
| ttaggtaatc taggagttaa attctaa | 927 |

<210> SEQ ID NO 6
<211> LENGTH: 1056
<212> TYPE: DNA
<213> ORGANISM: Artificial sequence
<220> FEATURE:
<223> OTHER INFORMATION: Periplasmic-localized T6SS effector from B. fragilis 638R

<400> SEQUENCE: 6

| | |
|---|---|
| atgaagaaaa ttttatcttt gcttgtgatg gctattgtag ctatacagtt ctcatttgcc | 60 |
| ggcgcttata gaaatgaata taaaacgcaa agtgaattta atgtcatctt ggaacggggg | 120 |
| gatgactatg aaggatttgt agttggcttg ggatatactt ggatgagtag caaggtaatt | 180 |
| ctaccggtaa atcaaaacgg atggagtcca atatctcgga tgtttcggt ggacgagagt | 240 |
| tttcatacga tagtctcaga aaggaaatac gatacctccc aatatgccta tgaaaaaagt | 300 |
| ctgatgcaag atccaacaaa agtttccgaa aaggtccgtg acttaatagt taaaacaaa | 360 |
| ggtaataata tcactgagat aaatttaggc caagaaaagc aatatttgcc cacgcgataat | 420 |
| agtcagataa gtattgtaat tactgacact ggcagtcggt acgaaattgt gattagtgcc | 480 |
| acggataact caaatggaaa gacttatgag gcaaagtatg agagtttgac ggacttggtg | 540 |
| tcagcggtac gcgattctgg tagcctgcct gctgtaaata aggaaggacc caatctggaa | 600 |

```
ggactggcag ggttaggatt cggaattgct gaaacagccg gaaattgggc tgagaagatt        660
atggataatc gaggtgcgta cttacctaag cagatgcgtt tctcgcccaa aacgcttccg        720
ccgattataa gattgccttt agggaactat caagtcccg ctaaaggtat gagtagagtg         780
cgtggagtag gtaaagcttt gggatgggca ggaatggtgc ttactggcta tcaagttgtg        840
cgtgatgtgc aaaatggtcg atttgccgtg gcaggtacaa gaattgccgt agcaggttta        900
gcttatggcg ttacttttat tccctatgtc ggttgggtct tagctatcgg tatcggagtg        960
gctgattata cttggggtga cgagttctat gactggatag acaatagagc ttctgaattg       1020
gaaatgtggt gggacggtgt aagattagca ttatga                                 1056
```

<210> SEQ ID NO 7
<211> LENGTH: 624
<212> TYPE: DNA
<213> ORGANISM: Artificial sequence
<220> FEATURE:
<223> OTHER INFORMATION: tetR (E. coli) Transcriptional Repressor

<400> SEQUENCE: 7

```
atgtctagat tagataaaag taaagtgatt aacagcgcat tagagctgct taatgaggtc         60
ggaatcgaag gtttaacaac ccgtaaactc gcccagaagc taggtgtaga gcagcctaca        120
ttgtattggc atgtaaaaaa taagcgggct ttgctcgacg ccttagccat tgagatgtta        180
gataggcacc atactcactt tgccccttta gaaggggaaa gctggcaaga ttttttacgt        240
aataacgcta aagttttag atgtgctta ctaagtcatc gcgatggagc aaaagtacat         300
ttaggtacac ggcctacaga aaacagtat gaaactctcg aaaatcaatt agcctttta         360 tgccaacaag gttttcact agagaatgca ttatatgcac tcagcgctgt ggggcatttt        420
actttaggtt gcgtattgga agatcaagag catcaagtcg ctaaagaaga agggaaaca         480 cctactactg atagtatgcc gccattatta cgacaagcta tcgaattatt tgatcaccaa        540
ggtgcagagc cagccttctt attcggcctt gaattgatca tatgcggatt agaaaaacaa        600
cttaaatgtg aaagtgggtc ttaa                                              624
```

<210> SEQ ID NO 8
<211> LENGTH: 138
<212> TYPE: DNA
<213> ORGANISM: Artificial sequence
<220> FEATURE:
<223> OTHER INFORMATION: Constitutive promoter (last nucleotide is +1
      TSS)

<400> SEQUENCE: 8

```
ttttgcaccc gctttccaag agaagaaagc cttgttaaat tgacttagtg taaaagcgca         60
gtactgcttg accataagaa caaaaaaact tccgataaag tttggaagat aaagctaaaa        120
gttcttatct ttgcagtc                                                     138
```

<210> SEQ ID NO 9
<211> LENGTH: 19
<212> TYPE: DNA
<213> ORGANISM: Artificial sequence
<220> FEATURE:
<223> OTHER INFORMATION: RBS

<400> SEQUENCE: 9

```
gaaataaaga catataaaa                                                     19
```

```
<210> SEQ ID NO 10
<211> LENGTH: 172
<212> TYPE: DNA
<213> ORGANISM: Artificial sequence
<220> FEATURE:
<223> OTHER INFORMATION: Constitutive promoter+RBS GH023

<400> SEQUENCE: 10
ttttgcaccc gctttccaag agaagaaagc cttgttaaat tgacttagtg taaaagcgca      60
gtactgcttg accataagaa caaaaaaact tccgataaag tttggaagat aaagctaaaa     120
gttcttatct ttgcagtccg aaataaagac atataaaga aagacacca tg              172

<210> SEQ ID NO 11
<211> LENGTH: 19
<212> TYPE: DNA
<213> ORGANISM: Artificial sequence
<220> FEATURE:
<223> OTHER INFORMATION: tetO2 operator binding site for TetR

<400> SEQUENCE: 11
tccctatcag tgatagaga                                                   19

<210> SEQ ID NO 12
<211> LENGTH: 183
<212> TYPE: DNA
<213> ORGANISM: Artificial sequence
<220> FEATURE:
<223> OTHER INFORMATION: P1TD Synthetic aTC-inducible promoter (distal
      tetO2)+RBS GH023

<400> SEQUENCE: 12
tttgcacccg ctttccaaga gaagaaagcc ttgttaaatt gacttagtgt aaaagcgcag      60
tactgcttga ccataagaac aaaaaaatct ctatcactga tagggataaa gtttggaaga     120
taaagctaaa agttcttatc tttgcagtcc gaaataaaga catataaaag aaaagacacc     180
atg                                                                   183

<210> SEQ ID NO 13
<211> LENGTH: 172
<212> TYPE: DNA
<213> ORGANISM: Artificial sequence
<220> FEATURE:
<223> OTHER INFORMATION: P1TC Synthetic aTC-inducible promoter (core
      tetO2)+RBS GH023

<400> SEQUENCE: 13
ttttgcaccc gctttccaag agaagaaagc cttgttaaat tgacttagtg taaaagcgca      60
gtactgcttg accataagaa caaaaaaact tccgataaag tttggtccct atcagtgata     120
gagattatct ttgcagtccg aaataaagac atataaaga aagacacca tg              172

<210> SEQ ID NO 14
<211> LENGTH: 191
<212> TYPE: DNA
<213> ORGANISM: Artificial sequence
<220> FEATURE:
<223> OTHER INFORMATION: P1TPSynthetic aTC-inducible promoter (proximal
      tetO2)+RBS GH023

<400> SEQUENCE: 14
ttttgcaccc gctttccaag agaagaaagc cttgttaaat tgacttagtg taaaagcgca      60
gtactgcttg accataagaa caaaaaaact tccgataaag tttggaagat aaagctaaaa     120
```

```
gttcttatct tgcagtctc cctatcagtg atagagacga aataaagaca tataaaagaa    180
aagacaccat g                                                        191

<210> SEQ ID NO 15
<211> LENGTH: 203
<212> TYPE: DNA
<213> ORGANISM: Artificial sequence
<220> FEATURE:
<223> OTHER INFORMATION: P1TDPSynthetic aTC-inducible promoter (distal
      and promixal tetO2)+RBS GH023

<400> SEQUENCE: 15
ttttgcaccc gctttccaag agaagaaagc cttgttaaat tgacttagtg taaaagcgca    60
gtactgcttg accataagaa caaaaaaatc tctatcactg atagggataa agtttggaag    120
ataaagctaa aagttcttat ctttgcagtc tccctatcag tgatagagac gaaataaaga    180
catataaaag aaaagacacc atg                                           203

<210> SEQ ID NO 16
<211> LENGTH: 137
<212> TYPE: DNA
<213> ORGANISM: Artificial sequence
<220> FEATURE:
<223> OTHER INFORMATION: P2  Constitutive promoter (last nucleotide is
      +1 TSS)

<400> SEQUENCE: 16 aagaaaggc gttttgtttt tcttctttac cttctttccc tttcgctaag agagtctgag    60
aaacgataga aaaagaaaag cgaaaaaact tccgaaaaca tttggtagtt aaaataaaac    120
ctcttacctt tgcaccc                                                  137

<210> SEQ ID NO 17
<211> LENGTH: 300
<212> TYPE: DNA
<213> ORGANISM: Artificial sequence
<220> FEATURE:
<223> OTHER INFORMATION: PBT1311Constitutive promoter of BT1311
      (upstream 300 base pairs)

<400> SEQUENCE: 17
tgatctggaa gaagcaatga aagctgctgt taagtctccg aatcaggtat tgttcctgac    60
aggtgtattc ccatccggta aacgcggata ctttgcagtt gatctgactc aggaataaat    120
tataaattaa ggtaagaaga ttgtaggata agctaatgaa atagaaaaag gatgccgtca    180
cacaacttgt cggcattctt ttttgtttta ttagttgaaa atatagtgaa aaagttgcct    240
aaatatgtat gttaacaaat tatttgtcgt aactttgcac tccaaatctg tttttaaaga    300

<210> SEQ ID NO 18
<211> LENGTH: 43
<212> TYPE: DNA
<213> ORGANISM: Artificial sequence
<220> FEATURE:
<223> OTHER INFORMATION: A21  RBS

<400> SEQUENCE: 18
cgcattttaa aataaaataa attatttatg atattaaacg aat                     43

<210> SEQ ID NO 19
<211> LENGTH: 43
<212> TYPE: DNA
<213> ORGANISM: Artificial sequence
```

<220> FEATURE:
<223> OTHER INFORMATION: B1 RBS

<400> SEQUENCE: 19
cgcattttaa aataaaataa ataatttact taattaaacg aat        43

<210> SEQ ID NO 20
<211> LENGTH: 43
<212> TYPE: DNA
<213> ORGANISM: Artificial sequence
<220> FEATURE:
<223> OTHER INFORMATION: rpiL* RBS

<400> SEQUENCE: 20
cgcattttaa aataaaataa attatttatt taattaaacg aat        43

<210> SEQ ID NO 21
<211> LENGTH: 43
<212> TYPE: DNA
<213> ORGANISM: Artificial sequence
<220> FEATURE:
<223> OTHER INFORMATION: B41 RBS

<400> SEQUENCE: 21
cgcattttaa aataaaataa atcatatagt taattaaacg aat        43

<210> SEQ ID NO 22
<211> LENGTH: 43
<212> TYPE: DNA
<213> ORGANISM: Artificial sequence
<220> FEATURE:
<223> OTHER INFORMATION: B40 RBS

<400> SEQUENCE: 22
cgcattttaa aataaaataa atcatgtagt taattaaacg aat        43

<210> SEQ ID NO 23
<211> LENGTH: 43
<212> TYPE: DNA
<213> ORGANISM: Artificial sequence
<220> FEATURE:
<223> OTHER INFORMATION: C56 RBS

<400> SEQUENCE: 23
cgcattttaa aataaaataa attattcgtt tagttaaacg aat        43

<210> SEQ ID NO 24
<211> LENGTH: 216
<212> TYPE: DNA
<213> ORGANISM: Artificial sequence
<220> FEATURE:
<223> OTHER INFORMATION: P1TDP-A21 Synthetic aTC-inducible promoter
      (distal and promixal tetO2)+RBS A21

<400> SEQUENCE: 24
tttgcacccg ctttccaaga gaagaaagcc ttgttaaatt gacttagtgt aaaagcgcag        60
tactgcttga ccataagaac aaaaaaatct ctatcactga tagggataaa gtttggaaga       120
taaagctaaa agttcttatc tttgcagtct ccctatcagt gatagagacg cattttaaaa       180
taaaataaat tatttatgat attaaacgaa tccatg                                 216

<210> SEQ ID NO 25
<211> LENGTH: 216
<212> TYPE: DNA
<213> ORGANISM: Artificial sequence

```
<220> FEATURE:
<223> OTHER INFORMATION: P1TDP-B1  Synthetic aTC-inducible promoter
      (distal and promixal tetO2)+RBS B1

<400> SEQUENCE: 25
tttgcacccg ctttccaaga gaagaaagcc ttgttaaatt gacttagtgt aaaagcgcag      60
tactgcttga ccataagaac aaaaaaatct ctatcactga tagggataaa gtttggaaga     120
taaagctaaa agttcttatc tttgcagtct ccctatcagt gatagagacg cattttaaaa     180
taaaataaat aatttactta attaaacgaa tccatg                              216

<210> SEQ ID NO 26
<211> LENGTH: 216
<212> TYPE: DNA
<213> ORGANISM: Artificial sequence
<220> FEATURE:
<223> OTHER INFORMATION: P1TDP-rpiL*  Synthetic aTC-inducible promoter
      (distal and promixal tetO2)+RBS rpiL*

<400> SEQUENCE: 26
tttgcacccg ctttccaaga gaagaaagcc ttgttaaatt gacttagtgt aaaagcgcag      60
tactgcttga ccataagaac aaaaaaatct ctatcactga tagggataaa gtttggaaga     120
taaagctaaa agttcttatc tttgcagtct ccctatcagt gatagagacg cattttaaaa     180
taaaataaat tatttattta attaaacgaa tccatg                              216

<210> SEQ ID NO 27
<211> LENGTH: 217
<212> TYPE: DNA
<213> ORGANISM: Artificial sequence
<220> FEATURE:
<223> OTHER INFORMATION: P1TDP-B41  Synthetic aTC-inducible promoter
      (distal and promixal tetO2)+RBS B41

<400> SEQUENCE: 27
ttttgcaccc gctttccaag agaagaaagc cttgttaaat tgacttagtg taaaagcgca      60
gtactgcttg accataagaa caaaaaaatc tctatcactg atagggataa agtttggaag     120
ataaagctaa aagttcttat ctttgcagtc tccctatcag tgatagagac gcattttaaa     180
ataaaataaa tcatatagtt aattaaacga atccatg                             217

<210> SEQ ID NO 28
<211> LENGTH: 216
<212> TYPE: DNA
<213> ORGANISM: Artificial sequence
<220> FEATURE:
<223> OTHER INFORMATION: P1TDP-B40  Synthetic aTC-inducible promoter
      (distal and promixal tetO2)+RBS B40

<400> SEQUENCE: 28
tttgcacccg ctttccaaga gaagaaagcc ttgttaaatt gacttagtgt aaaagcgcag      60
tactgcttga ccataagaac aaaaaaatct ctatcactga tagggataaa gtttggaaga     120
taaagctaaa agttcttatc tttgcagtct ccctatcagt gatagagacg cattttaaaa     180
taaaataaat catgtagtta attaaacgaa tccatg                              216

<210> SEQ ID NO 29
<211> LENGTH: 216
<212> TYPE: DNA
<213> ORGANISM: Artificial sequence
<220> FEATURE:
<223> OTHER INFORMATION: P1TDP-C56  Synthetic aTC-inducible promoter
      (distal and promixal tetO2)+RBS C56
```

<400> SEQUENCE: 29

```
tttgcacccg ctttccaaga gaagaaagcc ttgttaaatt gacttagtgt aaaagcgcag      60
tactgcttga ccataagaac aaaaaaatct ctatcactga tagggataaa gtttggaaga     120
taaagctaaa agttcttatc tttgcagtct ccctatcagt gatagagacg cattttaaaa     180
taaaataaat tattcgttta gttaaacgaa tccatg                               216
```

<210> SEQ ID NO 30
<211> LENGTH: 181
<212> TYPE: DNA
<213> ORGANISM: Artificial sequence
<220> FEATURE:
<223> OTHER INFORMATION: P2-A21  Constitutive promoter+RBS A21

<400> SEQUENCE: 30

```
aagaaaaggc gttttgtttt tcttctttac cttctttccc tttcgctaag agagtctgag      60
aaacgataga aaagaaaag cgaaaaaact tccgaaaaca tttggtagtt aaaataaaac     120
ctcttacctt tgcacccgcg cattttaaaa taaaataaat tatttatgat attaaacgaa     180
t                                                                     181
```

<210> SEQ ID NO 31
<211> LENGTH: 1008
<212> TYPE: DNA
<213> ORGANISM: Artificial sequence
<220> FEATURE:
<223> OTHER INFORMATION: P2-A21-tetR; P1TDPSingle unit tetracycline
      inducible cassette

<400> SEQUENCE: 31

```
ttaagaccca ctttcacatt taagttgttt ttctaatccg catatgatca attcaaggcc      60
gaataagaag gctggctctg caccttggtg atcaaataat tcgatagctt gtcgtaataa     120
tggcggcata ctatcagtag taggtgtttc ccttcttct ttagcgactt gatgctcttg     180
atcttccaat acgcaaccta agtaaaatg ccccacagcg ctgagtgcat ataatgcatt     240
ctctagtgaa aaaccttgtt ggcataaaaa ggctaattga ttttcgagag tttcatactg     300
tttttctgta ggccgtgtac ctaaatgtac ttttgctcca tcgcgatgac ttagtaaagc     360
acatctaaaa cttttagcgt tattacgtaa aaaatcttgc cagctttccc cttctaaagg     420
gcaaaagtga gtatggtgcc tatctaacat tcaatggct aaggcgtcga gcaaagcccg     480 cttattttt acatgccaat acaatgtagg ctgctctaca cctagcttct gggcgagttt     540
acgggttgtt aaaccttcga ttccgacctc attaagcagc tctaatgcgc tgttaatcac     600 tttacttta tctaatctag acatattcgt ttaatatcat aaataattta ttttatttta     660
aaatgcgcgg gtgcaaaggt aagaggtttt attttaacta ccaaatgttt tcggaagttt     720
tttcgctttt cttttctat cgtttctcag actctcttag cgaaagggaa agaaggtaaa     780
gaagaaaaac aaaacgcctt ttctttttg cacccgcttt ccaagagaag aaagccttgt     840
taaattgact tagtgtaaaa gcgcagtact gcttgaccat aagaacaaaa aaatctctat     900
cactgatagg gataaagttt ggaagataaa gctaaagtt cttatctttg cagtctccct     960
atcagtgata gagacgaaat aaagacatat aaaagaaag acaccatg                  1008
```

<210> SEQ ID NO 32
<211> LENGTH: 20
<212> TYPE: DNA
<213> ORGANISM: Artificial sequence

```
<220> FEATURE:
<223> OTHER INFORMATION: 8F 16S rDNA sequencing primer

<400> SEQUENCE: 32
agagtttgat cctggctcag                                                 20

<210> SEQ ID NO 33
<211> LENGTH: 20
<212> TYPE: DNA
<213> ORGANISM: Artificial sequence
<220> FEATURE:
<223> OTHER INFORMATION: 1492Rm 16S rDNA sequencing primer

<400> SEQUENCE: 33
cggctacctt gttacgactt                                                 20

<210> SEQ ID NO 34
<211> LENGTH: 44
<212> TYPE: DNA
<213> ORGANISM: Artificial sequence
<220> FEATURE:
<223> OTHER INFORMATION: del_1754_A primer, Deletion of BT1754

<400> SEQUENCE: 34
cttgatatcg aattcctgca ctttttcgtc tgcggacatt aatg                      44

<210> SEQ ID NO 35
<211> LENGTH: 39
<212> TYPE: DNA
<213> ORGANISM: Artificial sequence
<220> FEATURE:
<223> OTHER INFORMATION: del_1754_B primer, Deletion of BT1754

<400> SEQUENCE: 35
atcaatgaaa ttcatagttc tttctgtaat ccaattaag                            39

<210> SEQ ID NO 36
<211> LENGTH: 40
<212> TYPE: DNA
<213> ORGANISM: Artificial sequence
<220> FEATURE:
<223> OTHER INFORMATION: del_1754_C primer, Deletion of BT1754

<400> SEQUENCE: 36
gaactatgaa tttcattgat atcgtaaaga gggatatatg                           40

<210> SEQ ID NO 37
<211> LENGTH: 41
<212> TYPE: DNA
<213> ORGANISM: Artificial sequence
<220> FEATURE:
<223> OTHER INFORMATION: del_1754_D primer, Deletion of BT1754

<400> SEQUENCE: 37
ttcccctcca ccgcggtggc tggcattgtt gctgtgctat c                         41

<210> SEQ ID NO 38
<211> LENGTH: 39
<212> TYPE: DNA
<213> ORGANISM: Artificial sequence
<220> FEATURE:
<223> OTHER INFORMATION: del_0455_A primer, Deletion of BT0455

<400> SEQUENCE: 38
cttgatatcg aattcctgca agaattcacc accctgaac                            39
```

<210> SEQ ID NO 39
<211> LENGTH: 35
<212> TYPE: DNA
<213> ORGANISM: Artificial sequence
<220> FEATURE:
<223> OTHER INFORMATION: del_0455_B primer, Deletion of BT0455

<400> SEQUENCE: 39
gacttttcat aaatgggggt attagttaat ttaac                      35

<210> SEQ ID NO 40
<211> LENGTH: 35
<212> TYPE: DNA
<213> ORGANISM: Artificial sequence
<220> FEATURE:
<223> OTHER INFORMATION: del_0455_C primer, Deletion of BT0455

<400> SEQUENCE: 40
acccccattt atgaaaagtc ttcgaatctt tttgg                      35

<210> SEQ ID NO 41
<211> LENGTH: 49
<212> TYPE: DNA
<213> ORGANISM: Artificial sequence
<220> FEATURE:
<223> OTHER INFORMATION: del_0455_D primer, Deletion of BT0455

<400> SEQUENCE: 41
ttcccctcca ccgcggtggc gccagcatat cgggtaaaa attattttc        49

<210> SEQ ID NO 42
<211> LENGTH: 39
<212> TYPE: DNA
<213> ORGANISM: Artificial sequence
<220> FEATURE:
<223> OTHER INFORMATION: del_BO_04598_A primer, Deletion of BACOVA_04598

<400> SEQUENCE: 42
cttgatatcg aattcctgca ttcatggacc cgaaaatag                  39

<210> SEQ ID NO 43
<211> LENGTH: 35
<212> TYPE: DNA
<213> ORGANISM: Artificial sequence
<220> FEATURE:
<223> OTHER INFORMATION: del_BO_04598_B primer, Deletion of BACOVA_04598

<400> SEQUENCE: 43
atgttgtgtt caggctttat tgatctattt taatg                      35

<210> SEQ ID NO 44
<211> LENGTH: 36
<212> TYPE: DNA
<213> ORGANISM: Artificial sequence
<220> FEATURE:
<223> OTHER INFORMATION: del_BO_04598_C primer, Deletion of BACOVA_04598

<400> SEQUENCE: 44
ataaagcctg aacacaacat atttcgaact aaaaag                     36

<210> SEQ ID NO 45
<211> LENGTH: 40
<212> TYPE: DNA
<213> ORGANISM: Artificial sequence
<220> FEATURE:
<223> OTHER INFORMATION: del_BO_04598_D primer, Deletion of BACOVA_04598

<400> SEQUENCE: 45
ttcccctcca ccgcggtggc aacaacttgc ccgaagaatg                                    40

<210> SEQ ID NO 46
<211> LENGTH: 39
<212> TYPE: DNA
<213> ORGANISM: Artificial sequence
<220> FEATURE:
<223> OTHER INFORMATION: P1T_DP-GH023-NanoLuc-A primer, Placement of
      NanoLuc into P1T_DP-GH023 vector

<400> SEQUENCE: 46
acatataaaa gaaaagacac atggtcttca cactcgaag                                     39

<210> SEQ ID NO 47
<211> LENGTH: 38
<212> TYPE: DNA
<213> ORGANISM: Artificial sequence
<220> FEATURE:
<223> OTHER INFORMATION: P1T_DP-GH023-NanoLuc-B primer, Placement of
      NanoLuc into P1T_DP-GH023 vector

<400> SEQUENCE: 47
actggaagat aggcaattag ttacgccaga atgcgttc                                      38

<210> SEQ ID NO 48
<211> LENGTH: 45
<212> TYPE: DNA
<213> ORGANISM: Artificial sequence
<220> FEATURE:
<223> OTHER INFORMATION: P1T_DP-GH023-BT1854-A primer, Placement of
      BT1854 into P1T_DP-GH023 vector

<400> SEQUENCE: 48
acatataaaa gaaaagacac atgatagaat tctttcgga tatag                               45

<210> SEQ ID NO 49
<211> LENGTH: 42
<212> TYPE: DNA
<213> ORGANISM: Artificial sequence
<220> FEATURE:
<223> OTHER INFORMATION: P1T_DP-GH023-BT1854-B primer, Placement of
      BT1854 into P1T_DP-GH023 vector

<400> SEQUENCE: 49
actggaagat aggcaattag ctaactttgc acgatggaat ag                                 42

<210> SEQ ID NO 50
<211> LENGTH: 47
<212> TYPE: DNA
<213> ORGANISM: Artificial sequence
<220> FEATURE:
<223> OTHER INFORMATION: P1T_DP-GH023-BT0455-A primer, Placement of
      BT0455 into P1T_DP-GH023 vector

<400> SEQUENCE: 50
acatataaaa gaaaagacac atgaaaagaa atcattattt atttacc                            47

<210> SEQ ID NO 51
<211> LENGTH: 41
<212> TYPE: DNA
<213> ORGANISM: Artificial sequence
<220> FEATURE:
<223> OTHER INFORMATION: P1T_DP-GH023-BT0455-B primer, Placement of
      BT0455 into P1T_DP-GH023 vector

<400> SEQUENCE: 51
actggaagat aggcaattag tcatcgaatc aaatctttca g                41

<210> SEQ ID NO 52
<211> LENGTH: 28
<212> TYPE: DNA
<213> ORGANISM: Artificial sequence
<220> FEATURE:
<223> OTHER INFORMATION: NanoLuc A primer for fusing to promoter
      regions - 5' primer

<400> SEQUENCE: 52
atggtcttca cactcgaaga tttcgttg                               28

<210> SEQ ID NO 53
<211> LENGTH: 40
<212> TYPE: DNA
<213> ORGANISM: Artificial sequence
<220> FEATURE:
<223> OTHER INFORMATION: NanoLuc B primer, for fusing to promoter
      regions - Gibson cloning into pNBU2-Erm digested with SalI - 3'
      primer

<400> SEQUENCE: 53
cttgatatcg aattcctgca ttacgccaga atgcgttcgc                  40

<210> SEQ ID NO 54
<211> LENGTH: 49
<212> TYPE: DNA
<213> ORGANISM: Artificial sequence
<220> FEATURE:
<223> OTHER INFORMATION: BT0408_US primer for promoter-NanoLuc fusions

<400> SEQUENCE: 54
ttcccctcca ccgcggtggc attcaaaatc aggttccatc cttccttag        49

<210> SEQ ID NO 55
<211> LENGTH: 69
<212> TYPE: DNA
<213> ORGANISM: Artificial sequence
<220> FEATURE:
<223> OTHER INFORMATION: BT0408_DS primer for promoter-NanoLuc fusions

<400> SEQUENCE: 55
tcttcgagtg tgaagaccat aatttatact gtttaaaatg attatgatac aacaaatata   60
acatttttc                                                    69

<210> SEQ ID NO 56
<211> LENGTH: 53
<212> TYPE: DNA
<213> ORGANISM: Artificial sequence
<220> FEATURE:
<223> OTHER INFORMATION: BT1974_US primer for promoter-NanoLuc fusions

<400> SEQUENCE: 56
ttcccctcca ccgcggtggc atgattcata gtacagtcta cttgacgttt acc   53

<210> SEQ ID NO 57
<211> LENGTH: 65
<212> TYPE: DNA
<213> ORGANISM: Artificial sequence
<220> FEATURE:
<223> OTHER INFORMATION: BT1974_DS primer for promoter-NanoLuc fusions

<400> SEQUENCE: 57
tcttcgagtg tgaagaccat gatatcatat tttaaaaggt tattctgata aaatgtaaac    60
tgctc                                                              65

<210> SEQ ID NO 58
<211> LENGTH: 46
<212> TYPE: DNA
<213> ORGANISM: Artificial sequence
<220> FEATURE:
<223> OTHER INFORMATION: BT0646_US primer for promoter-NanoLuc fusions

<400> SEQUENCE: 58
ttcccctcca ccgcggtggc gccaagtatg gtttcttggg atatcg                 46

<210> SEQ ID NO 59
<211> LENGTH: 75
<212> TYPE: DNA
<213> ORGANISM: Artificial sequence
<220> FEATURE:
<223> OTHER INFORMATION: BT0646_DS primer for promoter-NanoLuc fusions

<400> SEQUENCE: 59
tcttcgagtg tgaagaccat aattctaaag ttttaattaa tactatagtt aaatcatctg    60
tttaattaac aatgc                                                   75

<210> SEQ ID NO 60
<211> LENGTH: 46
<212> TYPE: DNA
<213> ORGANISM: Artificial sequence
<220> FEATURE:
<223> OTHER INFORMATION: BT1311_US primer for promoter-NanoLuc fusions

<400> SEQUENCE: 60
ttcccctcca ccgcggtggc tgatctggaa gaagcaatga aagctg                 46

<210> SEQ ID NO 61
<211> LENGTH: 53
<212> TYPE: DNA
<213> ORGANISM: Artificial sequence
<220> FEATURE:
<223> OTHER INFORMATION: BT1311_DS primer for promoter-NanoLuc fusions

<400> SEQUENCE: 61
tcttcgagtg tgaagaccat tctttaaaaa cagatttgga gtgcaaagtt acg         53

<210> SEQ ID NO 62
<211> LENGTH: 50
<212> TYPE: DNA
<213> ORGANISM: Artificial sequence
<220> FEATURE:
<223> OTHER INFORMATION: BT3895_US primer for promoter-NanoLuc fusions

<400> SEQUENCE: 62
ttcccctcca ccgcggtggc aagatttgta tcattcggat ttggtagacg             50

<210> SEQ ID NO 63
<211> LENGTH: 57
<212> TYPE: DNA
<213> ORGANISM: Artificial sequence
<220> FEATURE:
<223> OTHER INFORMATION: BT3895_DS primer for promoter-NanoLuc fusions

<400> SEQUENCE: 63
tcttcgagtg tgaagaccat aattagttca gaattgagag tggaaaattg atagttc     57

```
<210> SEQ ID NO 64
<211> LENGTH: 55
<212> TYPE: DNA
<213> ORGANISM: Artificial sequence
<220> FEATURE:
<223> OTHER INFORMATION: BT2500_US primer for promoter-NanoLuc fusions

<400> SEQUENCE: 64
ttcccctcca ccgcggtggc agttattggc tgcaaaggta gataatattc tgttc          55

<210> SEQ ID NO 65
<211> LENGTH: 66
<212> TYPE: DNA
<213> ORGANISM: Artificial sequence
<220> FEATURE:
<223> OTHER INFORMATION: BT2500_DS primer for promoter-NanoLuc fusions

<400> SEQUENCE: 65
tcttcgagtg tgaagaccat aattgtatat tttttattag ttcaactttc tttttttgtt     60
cttctg                                                                66

<210> SEQ ID NO 66
<211> LENGTH: 61
<212> TYPE: DNA
<213> ORGANISM: Artificial sequence
<220> FEATURE:
<223> OTHER INFORMATION: BT0539_US primer for promoter-NanoLuc fusions

<400> SEQUENCE: 66
ttcccctcca ccgcggtggc taattcacaa aggaaatttc tgaaatatat tgtttatcag     60
c                                                                     61

<210> SEQ ID NO 67
<211> LENGTH: 59
<212> TYPE: DNA
<213> ORGANISM: Artificial sequence
<220> FEATURE:
<223> OTHER INFORMATION: BT0539_DS primer for promoter-NanoLuc fusions

<400> SEQUENCE: 67
tcttcgagtg tgaagaccat aagctaaaaa taaaatgatt gttttatcct gaatgtatc      59

<210> SEQ ID NO 68
<211> LENGTH: 50
<212> TYPE: DNA
<213> ORGANISM: Artificial sequence
<220> FEATURE:
<223> OTHER INFORMATION: BT0455_US primer for promoter-NanoLuc fusions

<400> SEQUENCE: 68
ttcccctcca ccgcggtggc cagcagaata catagaacag gaagaaaacg                50

<210> SEQ ID NO 69
<211> LENGTH: 51
<212> TYPE: DNA
<213> ORGANISM: Artificial sequence
<220> FEATURE:
<223> OTHER INFORMATION: BT0455_DS primer for promoter-NanoLuc fusions

<400> SEQUENCE: 69
tcttcgagtg tgaagaccat aaatgggggt attagttaat ttaacgaagg c              51
```

```
<210> SEQ ID NO 70
<211> LENGTH: 56
<212> TYPE: DNA
<213> ORGANISM: Artificial sequence
<220> FEATURE:
<223> OTHER INFORMATION: BT4213_US primer for promoter-NanoLuc fusions

<400> SEQUENCE: 70
ttcccctcca ccgcggtggc catagattaa aactgttttc aggattagat taaggg         56

<210> SEQ ID NO 71
<211> LENGTH: 58
<212> TYPE: DNA
<213> ORGANISM: Artificial sequence
<220> FEATURE:
<223> OTHER INFORMATION: BT4213_DS primer for promoter-NanoLuc fusions

<400> SEQUENCE: 71
tcttcgagtg tgaagaccat ctcttttttaa tttatttat cgggttccta ttgataac       58

<210> SEQ ID NO 72
<211> LENGTH: 38
<212> TYPE: DNA
<213> ORGANISM: Artificial sequence
<220> FEATURE:
<223> OTHER INFORMATION: BT4719_US primer for promoter-NanoLuc fusions

<400> SEQUENCE: 72
ttcccctcca ccgcggtggc cacggtcgcc ggtatagc                              38

<210> SEQ ID NO 73
<211> LENGTH: 64
<212> TYPE: DNA
<213> ORGANISM: Artificial sequence
<220> FEATURE:
<223> OTHER INFORMATION: BT4719_DS primer for promoter-NanoLuc fusions

<400> SEQUENCE: 73
tcttcgagtg tgaagaccat atactataaa aatgtttttt aatgagtact atttacttgc     60
tttg                                                                   64

<210> SEQ ID NO 74
<211> LENGTH: 42
<212> TYPE: DNA
<213> ORGANISM: Artificial sequence
<220> FEATURE:
<223> OTHER INFORMATION: BT0633_US primer for promoter-NanoLuc fusions

<400> SEQUENCE: 74
ttcccctcca ccgcggtggc ggtggtgacg taagccgtaa ac                         42

<210> SEQ ID NO 75
<211> LENGTH: 44
<212> TYPE: DNA
<213> ORGANISM: Artificial sequence
<220> FEATURE:
<223> OTHER INFORMATION: BT0633_DS primer for promoter-NanoLuc fusions

<400> SEQUENCE: 75
tcttcgagtg tgaagaccat caggaagccc gaaaaagaca gaac                       44

<210> SEQ ID NO 76
<211> LENGTH: 40
<212> TYPE: DNA
<213> ORGANISM: Artificial sequence
```

```
<220> FEATURE:
<223> OTHER INFORMATION: BT1854_US primer for promoter-NanoLuc fusions

<400> SEQUENCE: 76
ttcccctcca ccgcggtggc attgccgcta cgctgctttc                                40

<210> SEQ ID NO 77
<211> LENGTH: 59
<212> TYPE: DNA
<213> ORGANISM: Artificial sequence
<220> FEATURE:
<223> OTHER INFORMATION: BT1854_DS primer for promoter-NanoLuc fusions

<400> SEQUENCE: 77
tcttcgagtg tgaagaccat aaaataaatc gtattattaa aaggtggatt tgtctgatc         59

<210> SEQ ID NO 78
<211> LENGTH: 42
<212> TYPE: DNA
<213> ORGANISM: Artificial sequence
<220> FEATURE:
<223> OTHER INFORMATION: BT0295_US primer for promoter-NanoLuc fusions

<400> SEQUENCE: 78
ttcccctcca ccgcggtggc ctcatagtgg tggtaagggt gg                            42

<210> SEQ ID NO 79
<211> LENGTH: 52
<212> TYPE: DNA
<213> ORGANISM: Artificial sequence
<220> FEATURE:
<223> OTHER INFORMATION: BT0295_DS primer for promoter-NanoLuc fusions

<400> SEQUENCE: 79
tcttcgagtg tgaagaccat gacattttat ttgtcctatg ttgtattggg tg                 52

<210> SEQ ID NO 80
<211> LENGTH: 44
<212> TYPE: DNA
<213> ORGANISM: Artificial sequence
<220> FEATURE:
<223> OTHER INFORMATION: BT3486_US primer for promoter-NanoLuc fusions

<400> SEQUENCE: 80
ttcccctcca ccgcggtggc tctttggctt tagagcgtca gatc                          44

<210> SEQ ID NO 81
<211> LENGTH: 55
<212> TYPE: DNA
<213> ORGANISM: Artificial sequence
<220> FEATURE:
<223> OTHER INFORMATION: BT3486_DS primer for promoter-NanoLuc fusions

<400> SEQUENCE: 81
tcttcgagtg tgaagaccat aattattccg atttaattaa caccattctc attgc             55

<210> SEQ ID NO 82
<211> LENGTH: 46
<212> TYPE: DNA
<213> ORGANISM: Artificial sequence
<220> FEATURE:
<223> OTHER INFORMATION: BT0481_US primer for promoter-NanoLuc fusions

<400> SEQUENCE: 82
ttcccctcca ccgcggtggc gctgaaacat acagaggaat atgccc                        46
```

<210> SEQ ID NO 83
<211> LENGTH: 61
<212> TYPE: DNA
<213> ORGANISM: Artificial sequence
<220> FEATURE:
<223> OTHER INFORMATION: BT0481_DS primer for promoter-NanoLuc fusions

<400> SEQUENCE: 83
tcttcgagtg tgaagaccat aactgtgatg aattagatat ctattctttt atactttgtt    60
g                                                                    61

<210> SEQ ID NO 84
<211> LENGTH: 56
<212> TYPE: DNA
<213> ORGANISM: Artificial sequence
<220> FEATURE:
<223> OTHER INFORMATION: BT2778_US primer for promoter-NanoLuc fusions

<400> SEQUENCE: 84
ttcccctcca ccgcggtggc gtttccactc tttcttctat aaatttgtat ttaccc         56

<210> SEQ ID NO 85
<211> LENGTH: 56
<212> TYPE: DNA
<213> ORGANISM: Artificial sequence
<220> FEATURE:
<223> OTHER INFORMATION: BT2778_DS primer for promoter-NanoLuc fusions

<400> SEQUENCE: 85
tcttcgagtg tgaagaccat gtgcgtgtat tattttaata tgatgaatag aaaccg         56

<210> SEQ ID NO 86
<211> LENGTH: 43
<212> TYPE: DNA
<213> ORGANISM: Artificial sequence
<220> FEATURE:
<223> OTHER INFORMATION: BT4618_US primer for promoter-NanoLuc fusions

<400> SEQUENCE: 86
ttcccctcca ccgcggtggc atccaccatt gagcaccaac gac                      43

<210> SEQ ID NO 87
<211> LENGTH: 59
<212> TYPE: DNA
<213> ORGANISM: Artificial sequence
<220> FEATURE:
<223> OTHER INFORMATION: BT4618_DS primer for promoter-NanoLuc fusions

<400> SEQUENCE: 87
tcttcgagtg tgaagaccat tttttcttcg tattaaaatt tatgccgcaa agtatagg       59

<210> SEQ ID NO 88
<211> LENGTH: 51
<212> TYPE: DNA
<213> ORGANISM: Artificial sequence
<220> FEATURE:
<223> OTHER INFORMATION: BT4227_US primer for promoter-NanoLuc fusions

<400> SEQUENCE: 88
ttcccctcca ccgcggtggc gtttcttgcg aaacaaacaa aagaacaaaa c              51

<210> SEQ ID NO 89
<211> LENGTH: 65
<212> TYPE: DNA
<213> ORGANISM: Artificial sequence
<220> FEATURE:
<223> OTHER INFORMATION: BT4227_DS primer for promoter-NanoLuc fusions

<400> SEQUENCE: 89
tcttcgagtg tgaagaccat tttagttttg attttaatgt gtgatgctat aattctttt       60 tttag                                                                  65

<210> SEQ ID NO 90
<211> LENGTH: 61
<212> TYPE: DNA
<213> ORGANISM: Artificial sequence
<220> FEATURE:
<223> OTHER INFORMATION: BT1709_US primer for promoter-NanoLuc fusions

<400> SEQUENCE: 90
ttcccctcca ccgcggtggc ttgcataaaa tctttattgg aaaagttaat aaaacaatag      60
c                                                                     61

<210> SEQ ID NO 91
<211> LENGTH: 61
<212> TYPE: DNA
<213> ORGANISM: Artificial sequence
<220> FEATURE:
<223> OTHER INFORMATION: BT1709_DS primer for promoter-NanoLuc fusions

<400> SEQUENCE: 91
tcttcgagtg tgaagaccat tttgataaat ttacatatgg atacaatatc caaagaaaca     60
g                                                                     61

<210> SEQ ID NO 92
<211> LENGTH: 52
<212> TYPE: DNA
<213> ORGANISM: Artificial sequence
<220> FEATURE:
<223> OTHER INFORMATION: BT3347_US primer for promoter-NanoLuc fusions

<400> SEQUENCE: 92
ttcccctcca ccgcggtggc tcatcatcac acctacataa agttatgcaa ac             52

<210> SEQ ID NO 93
<211> LENGTH: 57
<212> TYPE: DNA
<213> ORGANISM: Artificial sequence
<220> FEATURE:
<223> OTHER INFORMATION: BT3347_DS primer for promoter-NanoLuc fusions

<400> SEQUENCE: 93
tcttcgagtg tgaagaccat aaatataaat aataaaatgg ttaaagtgca tccgaac        57

<210> SEQ ID NO 94
<211> LENGTH: 56
<212> TYPE: DNA
<213> ORGANISM: Artificial sequence
<220> FEATURE:
<223> OTHER INFORMATION: BT4179_US primer for promoter-NanoLuc fusions

<400> SEQUENCE: 94
ttcccctcca ccgcggtggc ctttctaaat ggtagtttaa atcttctctg tagtgc         56

<210> SEQ ID NO 95
<211> LENGTH: 52
<212> TYPE: DNA
<213> ORGANISM: Artificial sequence

```
<220> FEATURE:
<223> OTHER INFORMATION: BT4179_DS primer for promoter-NanoLuc fusions

<400> SEQUENCE: 95
tcttcgagtg tgaagaccat tgcctttata taatccggta aacgattgtt ag            52

<210> SEQ ID NO 96
<211> LENGTH: 31
<212> TYPE: DNA
<213> ORGANISM: Artificial sequence
<220> FEATURE:
<223> OTHER INFORMATION: RNA polymerase recognition sequence
<220> FEATURE:
<221> NAME/KEY: misc_feature
<222> LOCATION: (5)..(23)
<223> OTHER INFORMATION: variable sequence region, can be 19-21 residues
      in length, n is any nucleotide
<220> FEATURE:
<221> NAME/KEY: misc_feature
<222> LOCATION: (26)..(27)
<223> OTHER INFORMATION: variable sequence region, n can be any
      nucleotide

<400> SEQUENCE: 96
tttgnnnnnn nnnnnnnnnn nnntannttt g                                   31

<210> SEQ ID NO 97
<211> LENGTH: 4
<212> TYPE: DNA
<213> ORGANISM: Artificial sequence
<220> FEATURE:
<223> OTHER INFORMATION: highly conserved -33 RNA binding site

<400> SEQUENCE: 97 tttg                                                                 4

<210> SEQ ID NO 98
<211> LENGTH: 8
<212> TYPE: DNA
<213> ORGANISM: Artificial sequence
<220> FEATURE:
<223> OTHER INFORMATION: highly conserved -7 RNA binding site
<220> FEATURE:
<221> NAME/KEY: misc_feature
<222> LOCATION: (3)..(4)
<223> OTHER INFORMATION: variable sequence region, n can be any
      nucleotide

<400> SEQUENCE: 98 tanntttg                                                             8

<210> SEQ ID NO 99
<211> LENGTH: 4944
<212> TYPE: DNA
<213> ORGANISM: Artificial sequence
<220> FEATURE:
<223> OTHER INFORMATION: pNAB1 plasmid sequence

<400> SEQUENCE: 99
acgcgttatg agtaaacttg gtctgacagt taccaatgct taatcagtga ggcacctatc    60
tcagcgatct gtctatttcg ttcatccata gttgcctgac tccccgtcgt gtagataact   120
acgatacggg agggcttacc atctggcccc agtgctgcaa tgataccgcg agacccacgc   180
tcaccggctc cagatttatc agcaataaac cagccagccg gaagggccga gcgcagaagt   240
ggtcctgcaa cttatccgc ctccatccag tctattaatt gttgccggga agctagagta    300
agtagttcgc cagttaatag tttgcgcaac gttgttgcca ttgctacagg catcgtggtg   360
```

-continued

```
tcacgctcgt cgtttggtat ggcttcattc agctccggtt cccaacgatc aaggcgagtt    420
acatgatccc ccatgttgtg caaaaaagcg gttagctcct tcggtcctcc gatcgttgtc    480
agaagtaagt tggccgcagt gttatcactc atggttatgg cagcactgca taattctctt    540
actgtcatgc catccgtaag atgcttttct gtgactggtg agtactcaac caagtcattc    600
tgagaatagt gtatgcggcg accgagttgc tcttgcccgg cgtcaatacg ggataatacc    660
gcgccacata gcagaacttt aaaagtgctc atcattggaa aacgttcttc ggggcgaaaa    720
ctctcaagga tcttaccgct gttgagatcc agttcgatgt aacccactcg tgcacccaac    780
tgatcttcag catcttttac tttcaccagc gtttctgggt gagcaaaaac aggaaggcaa    840
aatgccgcaa aaagggaat aagggcgaca cggaaatgtt gaatactcat actcttcctt    900
tttcaatcat ggccgcggga ttaaaagtcg gggattggtg aacaaaaagg tgtttctctc    960
tttaagagaa atatcgtttt gctaaacagt tgatattgag gtatcatttt atcgtaaaag   1020 acattttgc tcaacaattg cttgacggaa atcaacaaat tttagcattt tgtaaaaaag    1080
tcgctatata atttggtgaa ttggagttat tttcatattt ttgcatcccg aagagtttct   1140
cttaaagaga gaaacatctt ttgcatacct tttccgaccg aatttttatg tcgtaaagag   1200
gggctttgca gggggtggac tcagaaagat gagaatagat gactattgta gttgaaacac   1260
atagaaagtt gctgatatac agaccgatac gcatatcggg atgaaccatg agtacgttct   1320
tttctcaaaa aacataaata ttcgaaaaga gatgcaataa attaaggaga ggttataatg   1380
aacaaagtaa atataaaaga tagtcaaaat tttattactt caaaatatca catagaaaaa   1440
ataatgaatt gcataagttt agatgaaaaa gataacatct ttgaaatagg tgcagggaaa   1500
ggtcatttta ctgctggatt ggtaaagaga tgtaattttg taacggcgat agaaattgat   1560
tctaaattat gtgaggtaac tcgtaataag ctcttaaatt atcctaacta tcaaatagta   1620
aatgatgata tactgaaatt tacatttcct agccacaatc catataaaat atttggcagc   1680
ataccttaca acataagcac aaatataatt cgaaaaattg tttttgaaag ttcagccaca   1740
ataagttatt taatagtgga atatggtttt gctaaaatgt tattagatac aaacagatca   1800
ctagcattgc tgttaatggc agaggtagat atttctatat tagcaaaaat tcctaggtat   1860
tatttccatc caaaacctaa agtggatagc acattaattg tattaaaaag aaagccagca   1920
aaaatggcat ttaaagagag aaaaaaatat gaaactttg taatgaaatg ggttaacaaa    1980
gagtacgaaa aactgtttac aaaaaatcaa tttaataaag ctttaaaaca tgcgagaata   2040
tatgatataa acaatattag tttcgaacaa tttgtatcgc tatttaatag ttataaaata   2100
tttaacggct aaaaacaata ggccacatgc aactgtaaat gtttacgcgt cctcggtacc   2160
ttaagaccca ctttcacatt taagttgttt ttctaatccg catatgatca attcaaggcc   2220
gaataagaag gctggctctg caccttggtg atcaaataat tcgatagctt gtcgtaataa   2280
tggcggcata ctatcagtag taggtgtttc ccttttcttct ttagcgactt gatgctcttg   2340
atcttccaat acgcaaccta agtaaaatg ccccacagcg ctgagtgcat ataatgcatt    2400
ctctagtgaa aaaccttgtt ggcataaaaa ggctaattga ttttcgagag tttcatactg   2460
tttttctgta ggccgtgtac ctaaatgtac ttttgctcca tcgcgatgac ttagtaaagc   2520
acatctaaaa ctttagcgt tattacgtaa aaaatcttgc cagctttccc cttctaaagg    2580
gcaaaagtga gtatggtgcc tatctaacat ctcaatggct aaggcgtcga gcaaagcccg   2640
cttatttttt acatgccaat acaatgtagg ctgctctaca cctagcttct gggcgagttt   2700
acgggttgtt aaaccttcga ttccgacctc attaagcagc tctaatgcgc tgttaatcac   2760
```

```
tttacttttta tctaatctag acataatgtt attttttaaa tgttgtgtga tcagtcctac   2820
tttgtttctt tcgacactgc aaatataaga acattatttg aaagttcaag tgaaacttta   2880
aattttaaca atagattaac cattgcaaac aaaacaaaaa aaaggtagcc caattgtaaa   2940
acgaaaggcc cagtctttcg actgagcctt tcgttttagt cgactttttg cacccgcttt   3000
ccaagagaag aaagccttgt taaattgact tagtgtaaaa gcgcagtact gcttgaccat   3060
aagaacaaaa aaatctctat cactgatagg gataaagttt ggaagataaa gctaaaagtt   3120
cttatctttg cagtctccct atcagtgata gagacgaaat aaagacatat aaaagaaaag   3180
acaccatgaa gaaaatttta tctttgcttg tgatggctat tgtagctata cagttctcat   3240
ttgccggcgg taaggaaata gaaataaaga aattgccaga gttcgaggct atggtgaatg   3300
ccggtaatac gacctatacg ggattggtag aaggcatcgg gtatgtgtat tggacaacag   3360
aaaccctata ttttatccgc actaatccag aacaattatg ggcgattcca aaatatcagc   3420
aaataccttt cccctatttt caaaggaaag atgcaatcat tgagaccaaa acattacata   3480
cactccatgt cttgtcaaaa gatgaactgt tgaaattgga ttacgatgcc tattatgcat   3540
tttatggtat cgtggaggag atgctaaaat ttattcatcg ggcggatgct attaaaagtt   3600
attgtgaaat acctcttccc ataataaaat ccaaaggagc actaaaggga aatgacgcaa   3660
gaaatgggat actatcatta ggtagtcaaa taaatgacca aatcggagct ccccttgatg   3720
cagcgaatat gctaatggat aataaacata taggcaaaat tggagatgga ttgtcgctta   3780
tttctattat agatgaggta ggtaatggtg aatattggtc agctgccgga gacattttac   3840
tgtttgcagc cggaaaaaca aaattaagtc cctatatgac tgtcataagt ttaggcacat   3900
ggatgtatga gacggacttg atgcaatgga gattagcatg tataaattat agcgattaca   3960
aaaaaacact aataaaatat cgagaattac aaaaaaaatt tgaaagtgga gacaaatctg   4020
tagaggaaaa gatgaatgaa tgtcacaaaa tactgaattc acattatata gagatgcaaa   4080
aaaatttagg taatctagga gttaaattct aactgcagcc cggggggatcc actagttcta   4140 gagcggccgc caccgcggtg gagggggaatt cccatgtcag ccgttaagtg ttcctgtgtc   4200
actcaaaatt gctttgagag gctctaaggg gcttctcagtg cgttacatcc ctggcttgtt   4260
gtccacaacc gttaaacctt aaaagcttta aaagccttat atattctttt ttttcttata   4320
aaacttaaaa ccttagaggc tatttaagtt gctgatttat attaatttta ttgttcaaac   4380
atgagagctt agtacgtgaa acatgagagc ttagtacgtt agccatgaga gcttagtacg   4440
ttagccatga gggtttagtt cgttaaacat gagagcttag tacgttaaac atgagagctt   4500
agtacgtgaa acatgagagc ttagtacgta ctatcaacag gttgaactgc tgatcttcag   4560
atcctctacg ccgacgcat cgtggccgga tcaattccgt tttccgctgc ataaccctgc   4620
ttcggggtca ttatagcgat ttttttcggta tatccatcct ttttcgcacg atatacagga   4680
ttttgccaaa gggttcgtgt agactttcct tggtgtatcc aacggcgtca gccgggcagg   4740
ataggtgaag taggcccacc cgcgagcggg tgttccttct tcactgtccc ttattcgcac   4800
ctggcggtgc tcaacgggaa tcctgctctg cgaggctggc cggctaccgc cggcgtaaca   4860
gatgagggca agcggatggc tgatgaaacc aagccaacca ggaagggcag cccacctatc   4920
acggaattga tccccctcga attg                                           4944
```

<210> SEQ ID NO 100
<211> LENGTH: 6195
<212> TYPE: DNA
<213> ORGANISM: Artificial sequence
<220> FEATURE:
<223> OTHER INFORMATION: pNAB2 plasmid sequence

<400> SEQUENCE: 100

```
acgcgttatg agtaaacttg gtctgacagt taccaatgct taatcagtga ggcacctatc      60
tcagcgatct gtctatttcg ttcatccata gttgcctgac tccccgtcgt gtagataact    120
acgatacggg agggcttacc atctggcccc agtgctgcaa tgataccgcg agacccacgc    180
tcaccggctc cagatttatc agcaataaac cagccagccg aagggccga gcgcagaagt     240
ggtcctgcaa cttatccgc ctccatccag tctattaatt gttgccggga agctagagta      300
agtagttcgc cagttaatag tttgcgcaac gttgttgcca ttgctacagg catcgtggtg    360
tcacgctcgt cgtttggtat ggcttcattc agctccggtt cccaacgatc aaggcgagtt    420
acatgatccc ccatgttgtg caaaaaagcg gttagctcct tcggtcctcc gatcgttgtc    480
agaagtaagt tggccgcagt gttatcactc atggttatgg cagcactgca taattctctt    540
actgtcatgc catccgtaag atgcttttct gtgactggtg agtactcaac caagtcattc    600
tgagaatagt gtatgcggcg accgagttgc tcttgcccgg cgtcaatacg ggataatacc    660
gcgccacata gcagaacttt aaaagtgctc atcattggaa aacgttcttc ggggcgaaaa    720
ctctcaagga tcttaccgct gttgagatcc agttcgatgt aacccactcg tgcacccaac    780
tgatcttcag catcttttac tttcaccagc gtttctgggt gagcaaaaac aggaaggcaa    840
aatgccgcaa aaaagggaat aagggcgaca cggaaatgtt gaatactcat actcttcctt    900
tttcaatcat ggccgcggga ttaaaagtcg gggattggtg aacaaaaagg tgtttctctc    960
tttaagagaa atatcgtttt gctaaacagt tgatattgag gtatcatttt atcgtaaaag   1020
acatttttgc tcaacaattg cttgacggaa atcaacaaat tttagcattt tgtaaaaaag   1080
tcgctatata atttggtgaa ttggagttat tttcatattt ttgcatcccg aagagtttct   1140
cttaaagaga gaaacatctt ttgcatacct tttccgaccg aattttatg tcgtaaagag    1200
gggctttgca gggggtggac tcagaaagat gagaatagat gactattgta gttgaaacac    1260
atagaaagtt gctgatatac agaccgatac gcatatcggg atgaaccatg agtacgttct   1320
tttctcaaaa aacataaata ttcgaaaaga gatgcaataa attaaggaga ggttataatg    1380
aacaaagtaa atataaaaga tagtcaaaat tttattactt caaaatatca catagaaaaa    1440
ataatgaatt gcataagttt agatgaaaaa gataacatct ttgaaatagg tgcagggaaa    1500
ggtcatttta ctgctggatt ggtaaagaga tgtaattttg taacggcgat agaaattgat    1560
tctaaattat gtgaggtaac tcgtaataag ctcttaaatt atcctaacta tcaaatagta    1620
aatgatgata tactgaaatt tacatttcct agccacaatc catataaaat atttggcagc   1680
ataccttaca acataagcac aaatataatt cgaaaaattg ttttttgaaag ttcagccaca   1740
ataagttatt taatagtgga atatggtttt gctaaaatgt tattagatac aaacagatca   1800
ctagcattgc tgttaatggc agaggtagat atttctatat tagcaaaaat tcctaggtat    1860
tatttccatc caaaacctaa agtggatagc acattaattg tattaaaaag aaagccagca    1920
aaaatggcat ttaaagagag aaaaaaatat gaaactttg taatgaaatg ggttaacaaa    1980
gagtacgaaa aactgtttac aaaaaaatcaa tttaataaag ctttaaaaca tgcgagaata   2040
tatgatataa acaatattag tttcgaacaa tttgtatcgc tatttaatag ttataaaata    2100
tttaacggct aaaaacaata ggccacatgc aactgtaaat gttacgcgt cctcggtacc     2160
ttaagaccca cttctcacatt taagttgttt ttctaatccg catatgatca attcaaggcc   2220
```

```
gaataagaag gctggctctg caccttggtg atcaaataat tcgatagctt gtcgtaataa    2280
tggcggcata ctatcagtag taggtgtttc cctttcttct ttagcgactt gatgctcttg    2340
atcttccaat acgcaaccta agtaaaatg ccccacagcg ctgagtgcat ataatgcatt     2400
ctctagtgaa aaaccttgtt ggcataaaaa ggctaattga ttttcgagag tttcatactg    2460
tttttctgta ggccgtgtac ctaaatgtac ttttgctcca tcgcgatgac ttagtaaagc    2520
acatctaaaa cttttagcgt tattacgtaa aaaatcttgc cagctttccc cttcaaagg     2580 gcaaaagtga gtatggtgcc tatctaacat ctcaatggct aaggcgtcga gcaaagcccg    2640 cttattttt acatgccaat acaatgtagg ctgctctaca cctagcttct gggcgagttt     2700
acgggttgtt aaaccttcga ttccgacctc attaagcagc tctaatgcgc tgttaatcac    2760 tttacttta tctaatctag acataatgtt atttttaaa tgttgtgtga tcagtcctac      2820
tttgtttctt tcgacactgc aaatataaga acattatttg aaagttcaag tgaaacttta    2880
aattttaaca atagattaac cattgcaaac aaaacaaaaa aaggtagcc caattgtaaa     2940 acgaaaggcc cagtctttcg actgagcctt tcgttttagt cgacttttg cacccgcttt     3000 ccaagagaag aaagccttgt taaattgact tagtgtaaaa gcgcagtact gcttgaccat    3060
aagaacaaaa aaatctctat cactgatagg gataaagttt ggaagataaa gctaaaagtt    3120
cttatctttg cagtctccct atcagtgata gagacgaaat aaagacatat aaaagaaaag    3180
acaccatgaa gaaatttta tctttgcttg tgatggctat tgtagctata cagttctcat    3240
ttgccggcgg taaggaaata gaaataaaga aattgccaga gttcgaggct atggtgaatg    3300
ccggtaatac gacctatacg ggattggtag aaggcatcgg gtatgtgtat tggacaacag    3360
aaaccctata ttttatccgc actaatccag aacaattatg ggcgattcca aaatatcagc    3420
aaataccttt cccctatttt caaggaaag atgcaatcat tgagaccaaa acattacata     3480
cactccatgt cttgtcaaaa gatgaactgt tgaaattgga ttacgatgcc tattatgcat    3540
tttatggtat cgtggaggag atgctaaaat ttattcatcg gcggatgct attaaaagtt     3600 attgtgaaat acctcttccc ataataaaat ccaaggagc actaagggaa atgacgcaa      3660 gaaatgggat actatcatta ggtagtcaaa taaatgacca atcggagct cccttgatg      3720 cagcgaatat gctaatggat aataaacata taggcaaaat tggagatgga ttgtcgctta    3780
tttctattat agatgaggta ggtaatggtg aatattggtc agctgccgga gacatttac     3840 tgtttgcagc cggaaaaaca aaattaagtc cctatatgac tgtcataagt ttaggcacat    3900
ggatgtatga gacggacttg atgcaatgga gattagcatg tataaattat agcgattaca    3960
aaaaaacact aataaaatat cgagaattac aaaaaaaatt tgaaagtgga gacaaatctg    4020
tagaggaaaa gatgaatgaa tgtcacaaaa tactgaattc acattatata gagatgcaaa    4080
aaaatttagg taatctagga gttaaattct aactgcagtt tttgcacccg ctttccaaga    4140
gaagaaagcc ttgttaaatt gacttagtgt aaaagcgcag tactgcttga ccataagaac    4200
aaaaaaatct ctatcactga tagggataaa gtttggaaga taaagctaaa agttcttatc    4260
tttgcagtct ccctatcagt gatagagacg aaataaagac atataaaaga aagacacca    4320 tgaagaaaat tttatctttg cttgtgatgg ctattgtagc tatacagttc tcatttgccg    4380
gcgcttatag aaatgaatat aaaacgcaaa gtgaatttaa tgtcatcttg aacggggggg    4440
atgactatga aggatttgta gttggcttgg gatatacttg gatgagtagc aaggtaattc    4500
taccggtaaa tcaaaacgga tggagtccaa tatctcggaa tgtttcggtg gacgagagtt    4560
ttcatacgat agtctcagaa aggaaatacg ataccctcca atatgcctat gaaaaaagtc    4620
```

```
tgatgcaaga tccaacaaaa gtttccgaaa aggtccgtga cttaatagtt aaaaacaaag    4680
gtaataatat cactgagata aatttaggcc aagaaaagca atatttgccc acggataata    4740
gtcagataag tattgtaatt actgacactg gcagtcggta cgaaattgtg attagtgcca    4800
cggataactc aaatggaaag acttatgagg caaagtatga gagtttgacg gacttggtgt    4860
cagcggtacg cgattctggt agcctgcctg ctgtaaataa ggaaggaccc aatctggaag    4920
gactggcagg gttaggattc ggaattgctg aaacagccgg aaattgggct gagaagatta    4980
tggataatcg aggtgcgtac ttacctaagc agatgcgttt ctcgcccaaa acgcttccgc    5040
cgattataag attgccttta gggaactatc aagtccccgc taaaggtatg agtagagtgc    5100
gtggagtagg taaagctttg ggatgggcag gaatggtgct tactggctat caagttgtgc    5160
gtgatgtgca aaatggtcga tttgccgtgg caggtacaag aattgccgta gcaggtttag    5220
cttatggcgt tacttttatt ccctatgtcg gttgggtctt agctatcggt atcggagtgg    5280
ctgattatac ttggggtgac gagttctatg actggataga caatagagct tctgaattgg    5340
aaatgtggtg ggacggtgta agattagcat tatgaggatc cactagttct agagcggccg    5400
ccaccgcggt ggagggggaat tcccatgtca gccgttaagt gttcctgtgt cactcaaaat    5460
tgctttgaga ggctctaagg gcttctcagt gcgttacatc cctggcttgt tgtccacaac    5520
cgttaaacct taaaagcttt aaaagccttta tatattcttt tttttcttat aaaacttaaa    5580
accttagagg ctatttaagt tgctgattta tattaatttt attgttcaaa catgagagct    5640
tagtacgtga aacatgagag cttagtacgt tagccatgag agcttagtac gttagccatg    5700
agggtttagt tcgttaaaca tgagagctta gtacgttaaa catgagagct tagtacgtga    5760
aacatgagag cttagtacgt actatcaaca ggttgaactg ctgatcttca gatcctctac    5820
gccggacgca tcgtggccgg atcaattccg ttttccgctg cataaccctg cttcggggtc    5880
attatagcga ttttttcggt atatccatcc tttttcgcac gatatacagg attttgccaa    5940
agggttcgtg tagactttcc ttggtgtatc caacggcgtc agccgggcag gataggtgaa    6000
gtaggcccac ccgcgagcgg gtgttccttc ttcactgtcc cttattcgca cctggcggtg    6060
ctcaacggga atcctgctct gcgaggctgg ccggctaccg ccggcgtaac agatgagggc    6120
aagcggatgg ctgatgaaac caagccaacc aggaagggca gcccacctat cacggaattg    6180
atccccctcg aattg                                                      6195
```

<210> SEQ ID NO 101
<211> LENGTH: 19
<212> TYPE: DNA
<213> ORGANISM: Artificial sequence
<220> FEATURE:
<223> OTHER INFORMATION: Distal tetO2 sequence

<400> SEQUENCE: 101

```
tctctatcac tgataggga                                                    19
```

US 11,549,115 B2

COMPOSITIONS AND METHODS FOR REGULATED GENE EXPRESSION

CROSS-REFERENCE TO RELATED APPLICATIONS

This application is a U.S. national phase application filed under 35 U.S.C. § 371 claiming benefit to International Patent Application No. PCT/US18/28056, filed Apr. 18, 2018, which is entitled to priority under 35 U.S.C. § 119(e) to U.S. Provisional Patent Application No. 62/486,526, filed Apr. 18, 2017, each of which application is hereby incorporated herein by reference in its entirety.

This application claims priority to U.S. Provisional Application No. 62/486,526, filed Apr. 18, 2017 which is hereby incorporated by reference herein in its entirety.

STATEMENT REGARDING FEDERALLY SPONSORED RESEARCH OR DEVELOPMENT

This invention was made with government support under GM105456 and GM118159 awarded by National Institutes of Health. The government has certain rights in the invention.

BACKGROUND OF THE INVENTION

The human gut is populated with enormous bacterial populations that impact many aspects of host physiology. While the ability to describe these communities by high-throughput sequencing has expanded dramatically, parallel tools to manipulate or engineer the microbiota have significantly lagged behind. Such tools are critical for experimental dissection of these poorly understood microbial consortia in the short term, and for future efforts to leverage the microbiota to predict, report on, and ameliorate disease.

Synthetic biology approaches provide an attractive means to address these obstacles, but genetic parts developed and validated in model organisms such as *Escherichia coli* are typically nonfunctional in *Bacteroidetes* or *Firmicutes*, which together account for ~90% of the microbiota in most individuals (The Human Microbiome Project Consortium, 2012, Nature, 486:207-214). Members of the most abundant and stable genus in healthy U.S. humans, *Bacteroides* (The Human Microbiome Project Consortium, 2012, Nature, 486: 207-214; Faith, J. J., et al., 2013, Science, 341:1237439-1237439), are typical in this regard. These gram-negative, obligate anaerobes are associated with a range of host phenotypes in mouse models, from modulating normal physiological processes (mucus production, villus development, immune maturation) to shaping interactions with invading pathogens and even behavior (Hsiao, E. Y., et al., 2013, Cell, 155:1451-1463; Ng, K. M., et al., 2013, Nature, 502:96-99; Wexler, H. M., 2007, Clinical Microbiology Reviews, 20:593-621). However, several features of *Bacteroides* preclude the use of standard synthetic biology tools. First, the RNA polymerase (RNAP) $\sigma^{70}$ holoenzyme recognizes a unique −33/−7 consensus sequence, TTTG ($N_{19-21}$) TANNTTTG (SEQ ID NO: 96), in promoter DNA (Bayley, D. P. et al., 2000, FEMS Microbiol. Lett., 193:149-154; Mastropaolo, M. D. et al., 2009, Microbiology, 155:2683-2693). Second, standard reporters of gene expression such as green fluorescent protein or ß-galactosides do not work well due to the oxygen requirement or high background from native enzymes. Third, ribosome binding site (RBS) strength is correlated with a complex set of features and not with the presence of a canonical Shine-Dalgarno sequence (Wegmann, U. et al., 2013, Appl. Environ. Microbiol., 79:1980-1989).

Native *Bacteroides* promoters that respond to plant-, fungal-, or mammal-derived polysaccharides or sugars can provide approximately $10^2$-fold range of activity and have been employed for regulated gene expression in *B. thetaiotaomicron*, *B. fragilis*, and *B. ovatus* (Hamady, Z. Z. R. et al., 2008, Microbiology, 154:3165-3174; Horn, N. et al., 2016, Front Microbiol., 7:207-209; Mimee, M. et al., 2015, Cell Syst., 1:62-71; Parker, A. C. et al., 2012, Plasmid, 68:86-92). However, even in the absence of inducer, these promoters are significantly activated in mouse models, possibly because of background from the host or its diet (Horn, N. et al., 2016, Front Microbiol., 7:207-209; Mimee, M. et al., 2015, Cell Syst., 1:62-71). Further, plant-, fungal- and mammal-derived polysaccharides are known to be actively consumed by the microbiota and have a large impact on microbiome composition and gene expression (Sonnenburg, J. L. et al., 2005, Science, 307:1955-1959). Lastly, the performance of these native promoters in heterologous species is not known.

Therefore, there is a need in the art for improved, functional synthetic biology components that are operable within the microbiota. The present invention addresses this unmet need.

SUMMARY OF THE INVENTION

In one aspect, the present invention provides an isolated nucleic acid molecule comprising an inducible synthetic promoter variant of the *Bacteroides* 16S rDNA promoter. In one embodiment, the inducible synthetic promoter comprises one or more repressor response elements. In one embodiment, the repressor response element comprises tetO2. In one embodiment, the inducible synthetic promoter comprises a ribosomal binding site (RBS). In some embodiments, the RBS is selected from the group consisting of GH023, A21, B1, rpiL, B41, B40, and C56.

In some embodiments, the inducible synthetic promoter comprises a nucleic acid sequence selected from the group consisting of SEQ ID NO: 12, SEQ ID NO: 13, SEQ ID NO: 14, SEQ ID NO: 15, SEQ ID NO: 24, SEQ ID NO: 25, SEQ ID NO: 26, SEQ ID NO: 27, SEQ ID NO: 28, and SEQ ID NO: 29.

In one embodiment, the inducible synthetic promoter is operably linked to a coding region. In one embodiment, the coding region encodes a therapeutic RNA or peptide. In one embodiment, the coding region encodes a toxic protein or peptide.

In one aspect, the present invention provides an expression cassette comprising an inducible synthetic promoter variant of the *Bacteroides* 16S rDNA promoter. In one embodiment, the inducible synthetic promoter comprises one or more repressor response elements. In one embodiment, the repressor response element comprises tetO2. In one embodiment, the inducible synthetic promoter comprises a ribosomal binding site (RBS). In some embodiments, the RBS is selected from the group consisting of GH023, A21, B1, rpiL, B41, B40, and C56. In some embodiments, the inducible synthetic promoter comprises a nucleic acid sequence selected from the group consisting of SEQ ID NO: 12, SEQ ID NO: 13, SEQ ID NO: 14, SEQ ID NO: 15, SEQ ID NO: 24, SEQ ID NO: 25, SEQ ID NO: 26, SEQ ID NO: 27, SEQ ID NO: 28, and SEQ ID NO: 29. In one embodiment, the inducible synthetic promoter is operably linked to a coding region. In one embodiment, the coding region encodes a therapeutic RNA or peptide.

In one embodiment, the expression cassette further comprises a nucleotide sequence encoding a repressor. In one embodiment, the repressor comprises tetR or a variant thereof.

In one aspect, the present invention provides a cell modified for inducible gene expression comprising a nucleic acid molecule comprising an inducible synthetic promoter variant of the *Bacteroides* 16S rDNA promoter. In one embodiment, the inducible synthetic promoter comprises one or more repressor response elements. In one embodiment, the repressor response element comprises tetO2. In one embodiment, the inducible synthetic promoter comprises a ribosomal binding site (RBS). In some embodiments, the RBS is selected from the group consisting of GH023, A21, B1, rpiL, B41, B40, and C56. In some embodiments, the inducible synthetic promoter comprises a nucleic acid sequence selected from the group consisting of SEQ ID NO: 12, SEQ ID NO: 13, SEQ ID NO: 14, SEQ ID NO: 15, SEQ ID NO: 24, SEQ ID NO: 25, SEQ ID NO: 26, SEQ ID NO: 27, SEQ ID NO: 28, and SEQ ID NO: 29. In one embodiment, the inducible synthetic promoter is operably linked to a coding region. In one embodiment, the coding region encodes a therapeutic RNA or peptide.

In one embodiment, the cell is modified to express a repressor. In one embodiment, the repressor comprises tetR.

In one embodiment, the cell is a bacterial cell. In one embodiment, the cell is of the genus *Bacteroides*.

In one aspect, the present invention provides a method of inducing gene expression in a cell comprising: providing a cell comprising a nucleic acid molecule comprising an inducible synthetic promoter variant of the *Bacteroides* 16S rDNA promoter operably linked to a coding region; and contacting the cell with an inducer.

In one embodiment, the inducible synthetic promoter comprises one or more repressor response elements. In one embodiment, the cell is modified to express a repressor, thereby inhibiting expression of the coding region. In one embodiment, the inducer inhibits the activity of the repressor, thereby inducing expression of the coding region.

In some embodiments, the inducible synthetic promoter comprises a nucleic acid sequence selected from the group consisting of SEQ ID NO: 12, SEQ ID NO: 13, SEQ ID NO: 14, SEQ ID NO: 15, SEQ ID NO: 24, SEQ ID NO: 25, SEQ ID NO: 26, SEQ ID NO: 27, SEQ ID NO: 28, and SEQ ID NO: 29.

In one aspect, the present invention provides a method of inducing gene expression in a cell comprising: providing a cell comprising a nucleic acid molecule comprising an inducible synthetic promoter variant of the *Bacteroides* 16S rDNA promoter operably linked to a coding region encoding at least one protein or peptide that is toxic to the cell; and contacting the cell with an inducer.

In one embodiment, the inducible synthetic promoter comprises one or more repressor response elements. In one embodiment, the nucleic acid molecule further comprises a nucleotide sequence for expression of a repressor protein under the control of a constitutive promoter, thereby inhibiting expression of the at least one protein or peptide that is toxic to the cell. In one embodiment, the inducer inhibits the activity of the repressor, thereby inducing expression of the at least one protein or peptide that is toxic to the cell.

In some embodiments, the inducible synthetic promoter comprises a nucleic acid sequence of SEQ ID NO: 12, SEQ ID NO: 13, SEQ ID NO: 14, SEQ ID NO: 15, SEQ ID NO: 24, SEQ ID NO: 25, SEQ ID NO: 26, SEQ ID NO: 27, SEQ ID NO: 28, or SEQ ID NO: 29. In one embodiment, the inducible synthetic promoter is operably linked to at least one nucleotide sequence encoding Bte1 or Bfe1. In one embodiment, the nucleic acid molecule comprises a nucleotide sequence of SEQ ID NO:99 or SEQ ID NO:100. In one embodiment, the nucleic acid molecule further comprises at least one nucleotide sequence homologous to a target nucleotide sequence.

BRIEF DESCRIPTION OF THE DRAWINGS

The following detailed description of embodiments of the invention will be better understood when read in conjunction with the appended drawings. It should be understood that the invention is not limited to the precise arrangements and instrumentalities of the embodiments shown in the drawings.

FIG. 1, comprising (FIG. 1A) Sequence conservation across 182 RNAP binding sites from 16S rRNA promoter regions from 19 *Bacteroides* genomes. Areas of conservation reflecting −33 and −7 RNAP binding sites (black bars) and the transcription-activating UP-element (blue bar) are indicated above the sequence logo. TetO2 sequences were placed and oriented as shown below the sequence logo. (FIG. 1B) Schematic of the P1 and P2 constitutive promoters and engineered P1 promoters containing tetO2 elements. The predicted UP-element, −33/−7 sites, and tetO2 operator sequences are designated as blue, black, and red boxes, respectively. The dashed line designates the transcription start site (+1), and the green semicircle indicates the GH023 RBS. (FIG. 1C) Activity of native P1, native P2, and tetO2-containing P1 promoters in *B. thetaiotaomicron* measured using the NanoLuc luciferase reporter and expressed as relative light units/colony forming unit (RLU/CFU). Luminescence from *B. thetaiotaomicron* carrying NanoLuc with no promoter is marked as "Vector". (FIG. 1D) Polymixin B minimal inhibitory concentrations (MIC) for *B. thetaiotaomicron* lpxF strains expressing lpxF from each promoter. The dashed line indicates the MIC for polymixin B in wildtype *B. thetaiotaomicron*. In FIG. 1C and FIG. 1D, values represent three biological replicates performed on separate days; letters indicate significantly different groups ($p < 1 \times 10^{-6}$).

FIG. 2, comprising FIG. 2A through FIG. 2C, depicts results from example experiments showing the regulation of *Bacteroides* gene expression via a synthetic inducer. (FIG. 2A) Strain design. (FIG. 2B) Activity of engineered, tetO2-containing promoters measured by luminescence (RLU/CFU) of NanoLuc-promoter fusions. (FIG. 2C) Addition of aTC restores lpxF-dependent polymixin B resistance to Bt::tetR lpxF carrying lpxF-promoter fusions. The dashed line indicates the PMB MIC for wildtype *B. thetaiotaomicron* (>1024 µg/mL). In FIG. 2B and FIG. 2C, asterisks indicate significant differences in gene expression in response to aTC ($p < 0.0001$). § indicates no significant difference as compared to vector control ($p > 0.1$).

FIG. 3, comprising (FIG. 3A and FIG. 3B) Promoter design and aTC-dependent growth of Bt::tetR P1T$_{DP}$$^{GH023}$-BT1754 in fructose and glucose. Error bars (for FIG. 3A and FIG. 3B) represent the standard deviation of three biological replicates on separate days. (FIG. 3C) Bt::tetR encoding either of two highly toxic antibacterial effectors from *B. fragilis* under the control of $P1T_{DP}^{GH023}$ grow at wildtype rates unless expression is induced with aTC. Error bars represent the standard deviation of two biological replicates on separate days; asterisks indicate the earliest timepoint with significant (p<0.001) differences compared to uninduced controls.

FIG. 4, comprising (FIG. 4A) Promoter activity of the $P1T_{DP}$ promoter fused to various RBSs (Mimee, M. et al., 2015, Cell Systems, 1:62-71) was measured using the NanoLuc reporter in wildtype *B. thetaiotaomicron* (grey) and Bt::tetR in the absence (red) or presence (green) of aTC. Luminescence from *B. thetaiotaomicron* carrying NanoLuc with no promoter is marked as "Vector". Error bars represent the standard deviation of three biological replicates on separate days. Asterisks above red bars indicate significant (p<0.02) reduction in activity compared to $P1T_{DP}^{GH023}$ in the OFF state; asterisks above green bars indicate significant (p<1×10$^{-5}$) increase in activity compared to $P1T_{DP}^{GH023}$ in the ON state. (FIG. 4B) *B. thetaiotaomicron* gene expression levels as previously measured by genome-wide transcriptional profiling (Sonnenburg, J. L. et al., 2005, Science, 307:1955-1959) are marked with grey lines. Promoters tested were selected from the designated genes labeled as black lines. (FIG. 4C) Luminescence from NanoLuc fusions to three engineered promoters can be modulated by aTC to span the entire expression range of the 18 native promoters selected to span the *B. thetaiotaomicron* transcriptome.

FIG. 6, comprising (FIG. 6A) Groups of germfree mice were colonized with Bt::tetR carrying the $P1T_{DP}^{GH023}$-NanoLuc, and promoter activity measured in feces over time. Mice were provided aTC as indicated. The grey dashed line and shading represent the average and standard deviation of fecal luminescence measured over time from mice colonized with wildtype *B. thetaiotaomicron* under the same regime of aTC exposure (n=6 mice for groups treated with 100 µg/mL aTC; n=2 mice for groups administered lower aTC concentrations). (FIG. 6B) Dose response of the $P1T_{DP}^{GH023}$ promoter to varying aTC concentrations in mice. (FIG. 6C) Luminescence production from Bt::tetR $P1T_{DP}^{GH023}$-NanoLuc in mice co-colonized with 13 other prominent human gut microbes (FIG. 12D). Mice (n=6) were given aTC as indicated. The grey dashed line and shading represents the average and standard deviation of fecal luminescence measured over time from mice colonized with wildtype *B. thetaiotaomicron* from FIG. 6A. (FIG. 6D) Inducer-dependent fecal luminescence production by Bt::tetR $P1T_{DP}^{GH023}$-NanoLuc in specific pathogen-free Rag$^{-/-}$ mice carrying a complete microbiota. The grey dashed line and shading represents the average and standard deviation of fecal luminescence on day -1; n=7 mice.

FIG. 7, comprising (FIG. 7A) aTC concentrations, (FIG. 7B) sialidase activity, and (FIG. 7C) free sialic acid levels in fecal samples collected over time from gnotobiotic mice monocolonized with Bt::3xtetR (green line), Bt::3xtetR BT0455 (red line), or Bt$^{RS}$ (black line). Mice were given aTC as indicated (n=6 mice per group in panels FIG. 7A and FIG. 7C; n=4 per group in panel FIG. 7B). In FIG. 7B and FIG. 7C, green and red dashed lines and shadings represent the average and standard deviation of sialidase activity (from the first 4 days; shown in FIG. 13D) and free sialic acid (from the full experiment; shown in FIG. 13E) in mice carrying Bt::3xtetR and Bt::3xtetR BT0455, respectively. The grey shading represents the time window when sialidase activity is no longer detected in mice carrying Bt$^{RS}$ yet free sialic acid remains. (FIG. 7D) Sialic acid levels are positively correlated with sialidase activity at low levels of enzyme activity but remain constant at higher levels of enzyme activity, suggesting that the reaction is substrate-limited. A best fit line based on Michaelis-Menten kinetics is shown in black. Conventional mice are shown in blue (n=4 mice).

FIG. 8, comprising FIG. 8A though (FIG. 8D) Expression of ss-Bte1 or ss-Bfe1 in *B. thetaiotaomicron* is highly toxic, because addition of aTC results in immediate decreases in viability and culture density; In the OFF state (without aTC), growth of strains carrying $P1T_{DP}$-ss-bte1, $P1T_{DP}$-ss-bfe1, and the Bt::tetR parental strain is equivalent.

FIG. 9, comprising (FIG. 9A and FIG. 9B) The 6 RBSs modulate $P1T_{DP}$ promoter expression by three orders of magnitude, in a pattern generally similar to that previously reported for a native *B. thetaiotaomicron* promoter (Mimee, M. et al., 2015, Cell Systems, 1:62-71). (FIG. 9C) Luminescence production from these 18 promoter fusions is largely proportional to the previously reported mRNA levels of the corresponding ORFs.

FIG. 10, comprising (FIG. 10A) The lpxF homolog in *B. ovatus* (BACOVA_04598) was identified, and the 62 base pairs upstream of this gene were replaced with the TetR-$P1T_{DP}^{B1}$ cassette. (FIG. 10B) With this one-step promoter replacement, PMB resistance becomes entirely dependent on aTC.

FIG. 12, comprising FIG. 12A though (FIG. 12A) This engineered system and aTC exposure do not impact *B. thetaiotaomicron* stability in the gut, and additionally, CFU measurements of Bt::tetR P1T$_{DP}^{GH023}$-NanoLuc were unchanged throughout the experiment. (FIG. 12B, and FIG. 12C) Modulation of gene expression by varying aTC concentrations is recapitulated in the distal small intestine, cecum and throughout the large intestine. (FIG. 12A, and FIG. 12D) To test the function of P1T$_{DP}$ platform in the context of a complex microbiota, germ-free mice were first colonized with a community consisting of Bt::tetR P1T$_{DP}^{GH023}$-NanoLuc and 13 additional microbial species representative of the 3 dominant phyla found in the human gut. In this community context, Bt::tetR P1T$_{DP}^{GH023}$-NanoLuc represented ~11% of the total community (~3×10$^{11}$ CFU/mL) based on strain- and species-specific qPCR analysis on DNA isolated from fecal pellets and selective culturing. (FIG. 12D, FIG. 12E, FIG. 12F) Fecal luminescence returned to baseline levels after removing the inducer, with complete repression 7-9 days after removal. Alpha and beta diversity analyses of these communities over the 19-day experiment indicate that the presence of aTC did not impact community structure.

FIG. 13, comprising (FIG. 13A) As previously reported (Ng, K. M., et al., 2013, Nature, 502: 96-99), *B. thetaiotaomicron* efficiently liberates sialic acid from the gut mucosa of monoassociated gnotobiotic mice; this activity is dependent on the *B. thetaiotaomicron* sialidase BT0455. (FIG. 13B) To understand how commensal sialidase activity modifies the gut environment, BT0455 was placed under the control of the P1T$_{DP}^{GH023}$ promoter (Bt:: 3xtetR BT0455 P1T$_{DP}^{GH023}$-BT0455, abbreviated Bt$^{RS}$ for regulated sialidase). (FIG. 13C) To measure sialidase enzyme activity, cell-free lysates from fecal samples were incubated with the artificial substrate 2-O-(p-Nitrophenyl)-tropheacetylneuraminic acid (pNP-SA), which is hydrolyzed by sialidases, and the subsequent release of the pNP moiety was monitored over time by LC-MS. pNP-SA was provided in 10-fold molar excess to its $K_m$ ($K_m$=0.11 mM) (Park, K. H. et al., 2013, BBA—Proteins and Proteomics, 1834:1510-1519) in order to ensure direct proportionality between the calculated initial reaction velocity and the sialidase concentration in each sample. (FIG. 13D) Fecal samples from control mice monocolonized with wildtype or BT0455 *B. thetaiotaomicron* strains exhibit constitutive or no sialidase activity, respectively. (FIG. 13E) Prior to aTC administration, fecal samples from mice carrying Bt$^{RS}$ show no detectable sialidase activity, indicating tight repression of the enzyme and the absence of pNP in the gut. (FIG. 13F) Exogenous sialic acid delivered by oral gavage to gnotobiotic mice monocolonized with *B. thetaiotaomicron* BT0455 exhibits a half-life of ~9 hours.

DETAILED DESCRIPTION

Figures 1A, 1B, 1C, 1D:
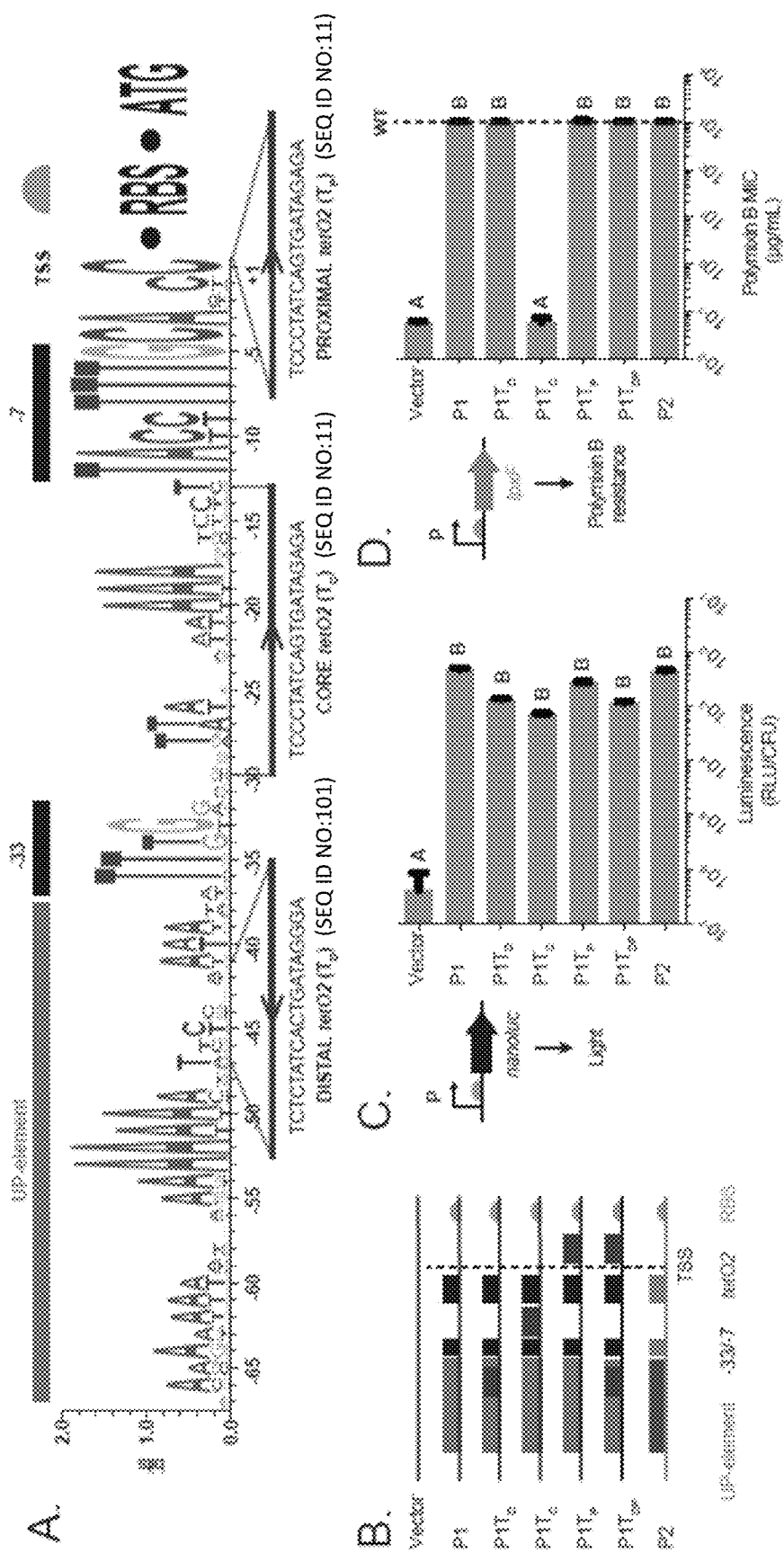
FIG. 1A through FIG. 1D, depicts results from example experiments showing the genetic architecture and construction of regulatable expression platforms in *Bacteroides*.

The present invention relates to compositions and methods for regulated gene expression of one or more proteins of interest. In certain aspects, the present invention provides for regulated gene expression in a bacterial cell. The invention is based in part upon the development of several synthetic promoters that couple gene expression to a synthetic inducer. In various embodiments, the invention provides compositions comprising an inducible synthetic promoter variant of the *Bacteroides* 16S rDNA promoter. For example, in various embodiments, the synthetic promoters described herein demonstrate over 10$^5$ fold dynamic range in protein expression.

In some aspects, the present invention provides for regulated gene expression in bacterial cells of the gut microbiome. The gut microbiota is implicated in numerous aspects of health and disease, but tools for dissecting the relationship between microbial activities and host physiology are limited. In certain aspects, the synthetic promoters described herein may be used for controlled gene expression in bacteria of the gut microbiota to investigate the molecular and temporal features of the host-microbiome interaction.

While many genetic parts will likely contribute to understanding the interactions between *Bacteroides* and their host, highly inducible yet tightly controlled gene expression systems are among the most useful. These regulated platforms provide several features absent from constitutive expression systems. First, gene expression can be modulated with time in the same strain or experiment, permitting kinetic studies of the bacterial or host response to production, depletion, or repeated exposures of a gene product. Second, inducible systems allow mechanistic study of essential or toxic gene products. Third, precise modulation of gene expression is the foundation for many more complex devices in synthetic biology.

Herein, a panel of tunable gene expression platforms for diverse human gut bacteria of the genus *Bacteroides* are described. In the OFF state, these systems recapitulate the phenotypes of mutants that lack the target gene entirely. Upon aTC induction, these engineered promoters can individually modulate gene expression up to 9,000-fold, spanning 5 orders of magnitude across the panel. By varying the aTC concentrations provided to mice carrying responsive strains, commensal gene expression inside the gut can be modulated across 3 orders of magnitude and can be fully repressed in vivo. This system may be used to measure the dynamic relationship between commensal sialidase expression and liberation of mucosal sialic acid, which serves as a receptor and nutrient for numerous viral and bacterial pathogens. These engineered systems function across diverse human gut *Bacteroides* and provide general design principles that are applicable across the microbiome.

In one embodiment, the invention relates to the use of the regulated gene expression system for genetic engineering of human gut commensal and other bacteria. This new method allows for direct modification of wildtype strains without working in a genetic mutant background. This has broad implications for genetic modification of human gut microbes that are directly isolated from humans or other animals.

Definitions

Unless defined otherwise, all technical and scientific terms used herein have the same meaning as commonly understood by one of ordinary skill in the art to which this invention belongs.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The terms "cells" and "population of cells" are used interchangeably and refer to a plurality of cells, i.e., more than one cell. The population may be a pure population comprising one cell type. Alternatively, the population may comprise more than one cell type. In the present invention, there is no limit on the number of cell types that a cell population may comprise.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system.

The term "microbiota," as used herein, refers to the population of microorganisms present within or upon a subject. The microbiota of a subject includes commensal microorganisms found in the absence of disease and may also include pathobionts and disease-causing microorganisms found in subjects with or without a disease or disorder.

As used herein, an "instructional material" includes a publication, a recording, a diagram, or any other medium of expression which can be used to communicate the usefulness of a compound, composition, or method of the invention in a kit. The instructional material of the kit of the invention can, for example, be affixed to a container which contains the identified compound, composition, or method of the invention or be shipped together with a container which contains the identified compound, composition, or method of the invention. Alternatively, the instructional material can be shipped separately from the container with the intention that the instructional material and the compound, composition, or method of the invention be used cooperatively by the recipient.

The terms "patient," "subject," "individual," and the like are used interchangeably herein, and refer to any animal, or cells thereof whether in vitro or in vivo, amenable to the methods described herein. In some non-limiting embodiments, the patient, subject or individual is, by way of non-limiting examples, a human, a dog, a cat, a cow, a pig, a chicken, a horse, or other domestic mammal.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of a mRNA molecule also consists of the nucleotide residues of the mRNA molecule which are matched with an anti-codon region of a transfer RNA molecule during translation of the mRNA molecule or which encode a stop codon. The coding region may thus include nucleotide residues comprising codons for amino acid residues which are not present in the mature protein encoded by the mRNA molecule (e.g., amino acid residues in a protein export signal sequence).

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "probiotic" refers to one or more bacteria that can be administered to a subject.

The term "promoter" as used herein is defined as a DNA sequence recognized by the machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

"Variant" as the term is used herein, is a nucleic acid sequence or a peptide sequence that differs in sequence from a reference nucleic acid sequence or peptide sequence respectively. Changes in the sequence of a nucleic acid variant may not alter the amino acid sequence of a peptide encoded by the reference nucleic acid, or may result in amino acid substitutions, additions, deletions, fusions and truncations. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

A "vector," as used herein, comprises an isolated nucleic acid and which can be used to deliver a nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention relates to compositions and methods for regulated gene expression of one or more proteins of interest. In some aspects, the present invention provides for regulated gene expression in a bacterial cell. In various embodiments, the invention provides compositions comprising an inducible synthetic promoter variant of the *Bacteroides* 16S rDNA promoter. In one embodiment, the synthetic promoter comprises a repressor response element. In one embodiment, the composition comprises the synthetic promoter operably linked to a coding region of interest.

In one embodiment, the composition comprises a bacterial cell comprising a nucleic acid molecule comprising the synthetic promoter operably linked to a coding region of interest. In some embodiments, the bacterial cell further comprises a nucleic acid molecule that expresses the repressor, which binds to the repressor binding element and thereby inhibits protein expression from the coding region of interest. In some embodiments, inducible expression from the coding region of interest is provided by administering an inducer to the bacterial cell. In one embodiment, the inducer inhibits repressor activity, thereby inducing protein expression from the coding region of interest.

In one aspect, the present invention provides a method for inducible expression of a RNA or protein of interest. In some embodiments, the method provides for inducible expression of a bacterial protein of interest in a bacterial cell. In one embodiment, the method comprises providing a cell comprising a nucleic acid molecule comprising a synthetic promoter operably linked to a coding region of interest, where the synthetic promoter comprises a repressor response element. In one embodiment, the cell comprises a repressor that binds to the repressor response element and thereby prevents protein expression from the coding region of interest. In one embodiment, the method comprises administering an inducer to the cell, thereby inducing RNA or protein expression from the coding region of interest. In some embodiments, the method provides for in vivo inducible expression of the RNA or protein, by inoculating a subject with the cell and administering to the cell a repressor inhibitor. In some embodiments, the level of gene expression is a function of the concentration of inducer administered, thereby providing further control over gene expression.

The synthetic promoters described herein may also be used for controlled expression of a therapeutic molecule, produced and secreted by the gut microbiota. For example, in some embodiments, a bacterial cell is modified to comprise a nucleic acid molecule comprising a synthetic promoter operably linked to a nucleotide sequence encoding a therapeutic RNA, peptide or polypeptide. In one embodiment, the invention provides a method comprising administering to a subject a bacterial cell comprising a nucleic acid molecule comprising a synthetic promoter operably linked to a nucleotide sequence encoding a therapeutic RNA, peptide or polypeptide, and administering an inducer to the cell to induce expression of the therapeutic RNA or peptide.

In one embodiment, the synthetic promoters described herein may also be used for genetic engineering including, in methods of generating mutations in a target nucleic acid molecule, or for methods of selecting or counter-selecting cells. For example, in some embodiments, a bacterial cell is modified to comprise a nucleic acid molecule comprising a synthetic promoter operably linked to a nucleotide sequence encoding a molecule that is toxic to the cell, and administering an inducer to the cell to induce expression of the toxic molecule. In such an embodiment, expression of the toxic molecule results in loss of viability of a cell that does not generate an additional mutation that results in disruption or deletion of the sequence encoding the toxic protein, however cells that generate an additional mutation that results in disruption or deletion of the sequence encoding the toxic protein remain viable. In some embodiments, an expression cassette comprising a synthetic promoter operably linked to a nucleotide sequence encoding a molecule that is toxic to the cell is integrated into a target nucleic acid molecule at a target locus. In some embodiments, an additional mutation that results in disruption or deletion of the sequence encoding the toxic protein also results in disruption or deletion of one or more proximal nucleotide sequences. Therefore, in one embodiment, the methods of the invention can be used to generate cells having a disruption or deletion of one or more target genes.

In some embodiments, the synthetic promoters of the invention can be used in a method of generating a mutation or deletion of an essential gene in a cell. In various embodiments, the coding synthetic promoter of the invention is operably linked to a coding region that encodes an essential gene. In such an embodiment, induction of expression of the coding region from the synthetic promoter of the invention can provide expression of the essential gene, allowing for the endogenous copy of the gene to be mutated or deleted.
Synthetic Promoter In some embodiments, the composition comprises a nucleic acid molecule comprising a synthetic promoter. As described herein, the synthetic promoters of the invention provide for an inducible gene expression of one or more genes of interest. For example, in some embodiments, the synthetic promoter is operably linked to a coding region of interest, and provides for inducing gene expression of the coding region of interest.

In one embodiment, the synthetic promoter comprises one or more repressor response elements. The one or more repressor response elements comprise a nucleotide sequence that binds to a repressor, and inhibits or prevents gene expression. Exemplary repressor response elements include, but are not limited to, tetracycline response elements and lactose response elements. Exemplary tetracycline response elements include, but are not limited to, tetO1 and tetO2, and variants thereof. Exemplary lactose response elements include lacO2 and variants thereof.

In some embodiments, the synthetic promoter comprises one or more copies of tetO2. In one embodiment, the synthetic promoter comprises at least one copy of tetO2 comprising the nucleotide sequence of SEQ ID NO: 11. In one embodiment, the synthetic promoter comprises at least two copies of tetO2. In one embodiment, the synthetic promoter comprises at least two copies of tetO2 comprising the nucleotide sequence of SEQ ID NO: 11.

In some embodiments, the synthetic promoter comprises variant P1 or P2 promoters of Bacteroides 16S rDNA. The native P1 promoter comprises the nucleotide sequence of SEQ ID NO: 8. The native P2 promoter comprises the nucleotide sequence of SEQ ID NO: 16. In one embodiment, the synthetic promoter of the invention comprises the highly conserved −33 (TTTG (SEQ ID NO: 97)) and −7 (TAnnTTTG (SEQ ID NO: 98)) RNA binding sites of the native P1 promoter and the native P2 promoter.

In some promoters of the invention, the synthetic promoter comprises a ribosomal binding site (RBS). Exemplary RBSs include, but are not limited to GH023, A21, B1, rpiL, B41, B40, and C56. Other RBSs that may be used in the present invention include those listed in Mimee et al. (2015, Cell Systems, 1: 62-71). In some embodiments, the promoter comprises a variant of an RBS described herein, or RBSs discovered the future. In one embodiment, the synthetic promoter comprises an RBS GH023 comprising the nucleotide sequence of SEQ ID NO: 9. In one embodiment, the synthetic promoter comprises an RBS A21 comprising the nucleotide sequence of SEQ ID NO: 18. In one embodiment, the synthetic promoter comprises an RBS B1 comprising the nucleotide sequence of SEQ ID NO: 19. In one embodiment, the synthetic promoter comprises an RBS rpiL comprising the nucleotide sequence of SEQ ID NO: 20. In one embodiment, the synthetic promoter comprises an RBS B41 comprising the nucleotide sequence of SEQ ID NO: 21. In one embodiment, the synthetic promoter comprises an RBS B40 comprising the nucleotide sequence of SEQ ID NO: 22. In one embodiment, the synthetic promoter comprises an RBS C56 comprising the nucleotide sequence of SEQ ID NO: 23.

In one embodiment, the synthetic promoter comprises the nucleotide sequence of SEQ ID NO: 12, which is referred to herein as P1TD. In one embodiment, the synthetic promoter comprises the nucleotide sequence of SEQ ID NO: 13, which is referred to herein as P1TC. In one embodiment, the synthetic promoter comprises the nucleotide sequence of SEQ ID NO: 14, which is referred to herein as P1TP. In one embodiment, the synthetic promoter comprises the nucleotide sequence of SEQ ID NO: 15, which is referred to herein as $P1T_{DP}$. In one embodiment, the synthetic promoter comprises the nucleotide sequence of SEQ ID NO: 24, which is referred to herein as $P1T_{DP}$-A21. In one embodiment, the synthetic promoter comprises the nucleotide sequence of SEQ ID NO: 25, which is referred to herein as $P1T_{DP}$-B1. In one embodiment, the synthetic promoter comprises the nucleotide sequence of SEQ ID NO: 26, which is referred to herein as $P1T_{DP}$-rpiL. In one embodiment, the synthetic promoter comprises the nucleotide sequence of SEQ ID NO: 27, which is referred to herein as $P1T_{DP}$-B41. In one embodiment, the synthetic promoter comprises the nucleotide sequence of SEQ ID NO: 28, which is referred to herein as $P1T_{DP}$-B40. In one embodiment, the synthetic promoter comprises the nucleotide sequence of SEQ ID NO: 29, which is referred to herein as $P1T_{DP}$-056.

The present synthetic promoters can be used to construct chimeric genes, expression cassettes, and expression vectors as well as host cells comprising the constructs. For example, in one embodiment, the composition comprises a nucleic acid molecule comprising: i) a synthetic promoter described herein and ii) a coding region of interest operably linked to the synthetic promoter.

In one embodiment, the composition comprises an expression cassette comprising the nucleic acid molecule of the invention. For example, in one embodiment, the expression cassette comprises a nucleic acid sequence comprising: i) a synthetic promoter described herein and ii) a coding region of interest operably linked to the synthetic promoter. In one embodiment, the expression cassette further comprises a second nucleic acid sequence encoding a repressor that binds to the synthetic promoter and inhibits expression of the coding region of interest. In one embodiment, the expression cassette comprises a second nucleic acid sequence comprising a constitutive promoter linked to a nucleic acid sequence encoding the repressor. Exemplary constitutive promoters include, but is not limited to, P1, P2, and P2-A21. In one embodiment, the expression cassette comprises a nucleic acid sequence encoding the repressor operably linked to the P1 constitutive promoter comprising the nucleotide sequence of SEQ ID NO: 8. In one embodiment, the expression cassette comprises a nucleic acid sequence encoding the repressor operably linked to the P2 constitutive promoter comprising the nucleotide sequence of SEQ ID NO: 10. In one embodiment, the expression cassette comprises a nucleic acid sequence encoding the repressor operably linked to the P2-A21 constitutive promoter comprising the nucleotide sequence of SEQ ID NO: 30. In some embodiments, the repressor encoded by the expression cassette is tetR. In one embodiment, the expression cassette comprises a nucleic acid sequence encoding tetR operably linked to the P2-A21 constitutive promoter.

In one embodiment, the expression cassette comprises a) a nucleic acid sequence encoding tetR operably linked to the P2-A21 constitutive promoter; and b) the P1T$_{DP}$ synthetic promoter operably linked to a coding region of interest. In one embodiment, the P2-A21-tetR; P1T$_{DP}$ expression cassette comprises the nucleotide sequence of SEQ ID NO: 31.

In one embodiment, the expression cassette comprises a) a nucleic acid molecule encoding a repressor molecule operably linked to a constitutive promoter; and b) at least one synthetic or engineered promoter of the invention operably linked to a nucleic acid molecule encoding at least one protein or peptide that can be used in a method of selection or counter-selection of cells. In one embodiment, the expression cassette comprises a) a nucleic acid molecule encoding tetR operably linked to a constitutive promoter; and b) one synthetic or engineered promoter of the invention operably linked to a nucleic acid molecule encoding at least one protein or peptide that can be used in a method of selection or counter-selection of bacterial cells. In one embodiment, the expression cassette comprises a) a nucleic acid molecule encoding tetR operably linked to a constitutive promoter; and b) two synthetic or engineered promoters of the invention, each independently operably linked to a nucleic acid molecule encoding at least one protein or peptide that can be used in a method of selection or counter-selection of bacterial cells. In one embodiment, the at least two synthetic or engineered promoters are inducible by the same inducer. In one embodiment, the at least two synthetic or engineered promoters are inducible by different inducers.

In addition, a vector comprising the nucleic acid molecule or expression cassette may be provided. Vectors useful for the transformation of a bacterial cell are common and described in the literature. Typically the vector contains a selectable marker and sequences allowing autonomous replication or chromosomal integration in the desired cell. In addition, suitable vectors may comprise a promoter region, including a synthetic promoter described herein, which harbors transcriptional initiation controls and a transcriptional termination control region, between which a coding region DNA fragment may be inserted, to provide expression of the inserted coding region. Both control regions may be derived from genes homologous to the transformed cell, although it is to be understood that such control regions may also be derived from genes that are not native to the specific cell. Termination control regions may also be derived from various genes, typically from genes native to the cell.

Non-limiting examples of suitable vectors include pAMβ1 and derivatives thereof (Renault et al., Gene 183: 175-182 (1996); and O'Sullivan et al., Gene 137:227-231 (1993)); pMBB1 and pHW800, a derivative of pMBB1 (Wyckoff et al. Appl. Environ. Microbiol. 62:1481-1486 (1996)); pMG1, a conjugative plasmid (Tanimoto et al., J. Bacteriol. 184:5800-5804 (2002)); pNZ9520 (Kleerebezem et al., Appl. Environ. Microbiol. 63:4581-4584 (1997)); pAM401 (Fujimoto et al., Appl. Environ. Microbiol. 67:1262-1267 (2001)); and pAT392 (Arthur et al., Antimicrob. Agents Chemother. 38:1899-1903 (1994)).

Vectors may be introduced into a host cell using methods known in the art, such as electroporation (Cruz-Rodz et al. Molecular Genetics and Genomics 224:1252-154 (1990), Bringel, et al. Appl. Microbiol. Biotechnol. 33: 664-670 (1990), Alegre et al., FEMS Microbiology letters 241:73-77 (2004)), and conjugation (Shrago et al., Appl. Environ. Microbiol. 52:574-576 (1986)). The nucleic acid molecule comprising the synthetic promoter can also be integrated into the chromosome of a cell using integration vectors (Hols et al., Appl. Environ. Microbiol. 60:1401-1403 (1990), Jang et al., Micro. Lett. 24:191-195 (2003). An exemplary integration vector is pNBU2 (Koropatkin, N. M. et al., 2008, Structure, 16:1105-1115; Larsbrink, J. et al., 2014, Nature, 506:498-502; Martens, E. C. et al., 2008, Cell Host and Microbe, 4:447-457). Other exemplary vectors that may be used include pLYL01 (Li et al. 1995, Journal of Bacteriology, 177(17): 4992-4999) and pFD340 (Smith et al. 1992, Plasmid, 27: 141-154).

In one embodiment, the vector comprises an expression cassette comprising a) a nucleic acid molecule encoding a repressor operably linked to a constitutive promoter; and b) at least one synthetic or engineered promoter of the invention operably linked to a nucleotide sequence encoding at least one protein or peptide that can be used in a method of selection or counter-selection of a cell. In one embodiment, the vector comprises an expression cassette comprising a) a nucleic acid molecule encoding tetR operably linked to a constitutive promoter; and b) one synthetic or engineered promoter of the invention operably linked to a nucleotide sequence encoding at least one protein or peptide that can be used in a method of selection or counter-selection of a cell. In one embodiment, the vector comprises pNAB1, having a nucleotide sequence of SEQ ID NO:99, comprising an engineered promoter operably linked to Bte1. In one embodiment, the vector comprises an expression cassette comprising a) a nucleic acid molecule encoding tetR operably linked to a constitutive promoter; and b) two synthetic or engineered promoters of the invention each independently operably linked to a nucleotide sequence encoding at least one protein or peptide that can be used in a method of selection or counter-selection of bacterial cells. In one embodiment, the at least two synthetic or engineered promoters are inducible by the same inducer. In one embodiment, the at least two synthetic or engineered promoters are inducible by different inducers. In one embodiment, the vector comprises pNAB2, having a nucleotide sequence of SEQ ID NO:100, comprising a first engineered promoter operably linked to Bte1 and a second engineered promoter operably linked to Bfe1.

In various embodiments, the vector comprising an expression cassette of the invention further comprises a nucleotide sequence having at least 80%, at least 85%, at least 90%, at least 91%, at least 92%, at least 93%, at least 94%, at least 95%, at least 96%, at least 97%, at least 98%, at least 99%, or 100% homology to a target nucleotide sequence of a host cell. In one embodiment, the nucleotide sequence having homology to a target nucleotide sequence of a host cell allows recombination between the vector of the invention and the target nucleotide sequence such that the expression cassette of the invention is integrated into a nucleic acid molecule comprising the target nucleotide sequence. In one embodiment, a nucleic acid molecule comprising the target nucleotide sequence is a genomic nucleic acid molecule of the host cell.

Cells

In one embodiment, the composition comprises a cell comprising a nucleic acid molecule comprising a synthetic promoter described herein. For example, in one embodiment, the composition comprises a cell that is modified to comprise a nucleic acid molecule comprising a synthetic promoter described herein operably linked to a coding region of interest. The coding region of interest may be a coding region endogenous to the cell, or alternatively may be any exogenous coding region of interest expressing a desired peptide or polypeptide. In one embodiment, the cell is further modified to comprise a nucleic acid molecule encoding a repressor. For example, in some embodiments, the cell is modified with one or more expression vectors comprising a) a synthetic promoter described herein operably linked to a coding region of interest; and b) a nucleic acid sequence encoding a repressor.

The cell may be of any suitable cell type. In one embodiment, the cell is a bacterial cell. In some embodiments, the cell is of phylum *Bacteroidetes*. In some embodiments, the cell is of a bacterial genus including but not limited to, *Bacteroides*, *Parabacteroides*, and *Flavobacteria*.

In one embodiment, the cell is of a *Bacteroides* species including but not limited to, *Bacteroides caccae, Bacteroides cellulosilyticus, Bacteroides dorei, Bacteroides eggerthii, Bacteroides faecis, Bacteroides finegoldii, Bacteroides fragilis, Bacteroides intestinalis, Bacteroides oleiciplenus. Bacteroides ovatus, Bacteroides plebeius, Bacteroides salanitronis. Bacteroides salyersiae, Bacteroides stercoris, Bacteroides thetaiotaomicron, Bacteroides uniformis, Bacteroides vulgatus, Bacteroides xylanisolvens, Bacteroides acidifaciens, Bacteroides gracilis, Bacteroides oris, Bacteroides putredinis, Bacteroides pyrogenes*, and *Bacteroides suis*.

In various embodiments, the cell comprising the present expression system uses an effective amount of intracellular repressor to act as a transcriptional regulator. Exemplary repressors include, but is not limited to, tetR, lacR, or variants thereof. For example, in some embodiments, the cell expresses a TetR variants that bind to DNA only when tetracycline is present. In some embodiments, the cell expresses a tetR variant that binds to DNA only when tetracycline is absent. Variations in TetR-regulated promoters expand the versatility, range, and regulatory properties of this system (Bertram and Hillen, 2008, Microb Biotechnol, 1: 2016; Hillen and Berens, 1994, Annu Rev Microbiol, 48: 345-369). For example, modifications of TetR have been identified that alter its specificity for tetracycline analogs (Henssler et al., 2004, Biochemistry, 43: 9512-9518; Scholz et al., 2003, Journal of Microbiology, 329: 217-227), change its allosteric interactions so that aTC acts as a corepressor (Kamionka et al., 2004, Nucleic Acids Research, 32: 842-847; Scholz et al., 2004, Mol Microbiol, 53: 777-789), or change its operator specificity to selectively recognize distinct tetO variants (Helbl and Hillen, 1998, Journal of Molecular Biology, 276: 313-318; Helbl et al., 1998, Journal of Microbiology, 276: 319-324; Krueger et al., 2007, Gene, 404: 93-100). These modifications considerably expand the range of conceivable applications of TetR-regulated systems and increase the possibilities for multi-gene regulation within *Bacteroides*. In some embodiments, the cell expresses a tetR variant that specifically bind to a modified tetO2 or tetO1 sequences. Therefore, multiple different tetR proteins in the cell can carry out regulation differently based on the repressor elements and the presence of tetracycline. In some embodiments, the cell expresses a tetR variant that binds to tetracycline analogs at different affinities.

The repressor can be provided by an expressible copy of the repressor anywhere within the cell. In one embodiment, the cell comprises an expressible copy of the repressor gene as part of a vector. In one embodiment, the expressible copy of the repressor gene is located on the same vector as the nucleic acid sequence comprising the synthetic promoter operably linked to the coding region of interest. In some embodiments, the repressor gene may be located on the same expression vector and transcribed in opposite orientation relative to the nucleic acid sequence comprising the synthetic promoter operably linked to the coding region of interest.

In some embodiments, the cell is a member of bacterial family able to grows over a wide range of temperatures, pH values, and solvent tolerances. It is contemplated that any bacteria can be modified for expression of the present nucleic acid molecules comprising the synthetic promoter. Transcription, translation, and the protein biosynthetic apparatus are universal genetic processes. Because of this, large-scale microbial growth and functional gene expression may utilize a wide range of simple or complex carbohydrates, organic acids and alcohols, i.e., methanol, saturated hydrocarbons such as methane or carbon dioxide in the case of photosynthetic or chemoautotrophic hosts. However, the functional gene expression may be regulated, repressed or depressed by specific growth conditions, which may include the form and amount of nitrogen, phosphorous, sulfur, oxygen, carbon or any trace mineral or nutrient including small inorganic ions. In addition, the regulation of functional gene expression may be achieved by the presence or absence of specific regulatory molecules added to the culture and not typically considered a nutrient or energy source. In some embodiments, growth rate is also an important regulatory factor in functional gene expression and can be modified to alter functional gene expression.

Fermentation media must contain suitable carbon substrates. In various embodiments, suitable substrates include, but are not limited to, monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. It is contemplated that the source of carbon utilized in the present invention may encompass a wide variety of carbon containing substrates and will only be limited by the choice of organism. Preferred carbon substrates include glucose, fructose, and sucrose.

In various embodiments, in addition to a carbon source, fermentation media contains other components suitable and/ or necessary for the growth of the cultures and promotion of the expression of the present fusion peptides. These are known to those skilled in the art and include minerals, salts, cofactors, buffers, etc.

In some embodiments, the inducer is added to the fermentation media to induce gene expression from the coding region of interest.

In various embodiments, suitable culture conditions vary and depend on the chosen production host and are generally known in the art. Typically, cells are grown at a temperature in the range of about 25° C. to about 40° C. in an appropriate medium. Suitable growth media in the present invention include common commercially prepared media such as Luria Bertani (LB) broth, Sabouraud Dextrose (SD) broth or Yeast medium (YM) broth. Other defined or synthetic growth media may also be used and the appropriate medium for growth of the particular microorganism will be known by one skilled in the art of microbiology or fermentation science. The use of agents known to modulate catabolite repression directly or indirectly, e.g., cyclic adenosine 2':3'-monophosphate, may also be incorporated into the fermentation medium.

Suitable pH ranges for the fermentation are typically between pH 5.0 to pH 9.0, where pH 6.0 to pH 8.0 is preferred. Fermentation may be performed under either aerobic or anaerobic conditions whereas aerobic conditions are generally preferred.

Coding Region

In some embodiments, the nucleic acid molecule comprises a coding region of interest which encodes for an RNA, peptide or polypeptide of interest. In some embodiments, the encoded RNA is a non-coding RNA, coding RNA, mRNA, miRNA, siRNA, and the like. In some embodiments, the encoded peptide or polypeptide of interest may be any peptide, protein, enzyme, fusion protein, chimeric protein, or the like. In some embodiments, the encoded peptide or polypeptide of interest is an endogenous protein of the cell to which the nucleic acid molecule is administered. In some embodiments, the endogenous gene encoding the endogenous protein in the cell is replaced by the nucleic acid molecule described herein by integrating the nucleic acid molecule into the genome of the cell. In some embodiments, the encoded RNA or peptide of interest is foreign to the cell to which the nucleic acid molecule is administered, thereby providing for regulated expression of an exogenous gene.

In some embodiments, the coding region expresses a bacterial protein, thereby providing regulated or controlled expression of the bacterial protein. In one embodiment, regulated expression of a bacterial protein allows for investigation of the role of the bacterial protein in bacterial growth, bacterial-host interaction, host health or host pathology. In one embodiment, regulated expression of a bacterial protein allows for genetic modification of a cell.

In some embodiments, the coding region expresses a therapeutic RNA, peptide or polypeptide. The therapeutic RNA, peptide or polypeptide may be any suitable RNA, peptide or polypeptide that can be expressed by the cell and delivered to the host organism harboring the cell. An exemplary therapeutic peptide includes Amuc100, an outer membrane protein from *Akkermansia muciniphila*, which interacts with the Toll-like receptor 2, and has been shown to improve the gut barrier and metabolism in obese and diabetic mice (Plovier et al., 2017, Nature Medicine, 23: 107-113). Another exemplary therapeutic peptide is indole-3-propionic acid (IPA), which is a neuroprotective antioxidant that might have therapeutic use in Alzheimer's disease. IPA is produced by intestinal microbes, one of them being *Clostridium sporogenes*.

In some embodiments, the coding region expresses at least one protein or peptide that can be used in a method of selection or counter-selection of bacterial cells. In various embodiments, a protein or peptide that can be used in a method of selection or counter-selection of bacterial cells is a bacterial toxin of a toxin/anti-toxin system, a bacterial effector protein, a contact dependent growth inhibitor, a ribonuclease (e.g., Barnase from *Bacillus amyloliquefaciens*), a bacteriocin or a bacteriocin-like effector peptide. In one embodiment, the coding region expresses an effector protein from a bacterial secretion system. Exemplary bacterial secretion systems include, but are not limited to, type I (T1SS), type II (T2SS), type III (T3SS), type IV (T4SS), type V (T5SS), type VI (T6SS), and type VII (T7SS). In one embodiment, the coding region expresses at least one of Bte1 and Bfe1.

In some embodiments, the synthetic promoters of the invention can be used in a method of generating a mutation or deletion of an essential gene in a cell. In various embodiments, the coding synthetic promoter of the invention is operably linked to a coding region that encodes an essential gene. In such an embodiment, induction of expression of the coding region from the synthetic promoter of the invention can provide expression of the essential gene, allowing for the endogenous copy of the gene to be mutated or deleted.

Methods

In one embodiment, the present invention provides for regulated gene expression in a cell through the use of a synthetic promoter described herein. In some embodiments, the method comprises administering to a cell a nucleic acid molecule comprising a synthetic promoter described herein operably linked to a coding region of interest. In one embodiment, the method comprises administering to the cell a repressor, which prevents expression from the coding region of interest. In one embodiment, the cell expresses a repressor, which prevents expression from the coding region of interest. In one embodiment, the method comprises administering to the cell a nucleic acid molecule that expresses the repressor. For example, in one embodiment, the method comprises administering to the cell a vector comprising a) a synthetic promoter operably linked to a coding region of interest; and b) a nucleic acid encoding a repressor. In some embodiments, the synthetic promoter operably linked to the coding region of interest and the nucleic acid encoding the repressor are on the same nucleic acid molecule. In other embodiments, the synthetic promoter operably linked to the coding region of interest and the nucleic acid encoding the repressor are on different nucleic acid molecules.

In some embodiments, the method comprises administering an inducer to the cell to induce expression from the coding region of interest. In some embodiments, the inducer is an inhibitor of the repressor. In various embodiments, the inducer is any suitable inhibitor of the repressor, including but not limited to, a nucleic acid molecule, siRNA, protein, antibody, small molecule, or the like, which inhibits the expression or activity of the repressor. In some embodiments, the inducer binds to the repressor and prevents the repressor from binding the repressor response element of the synthetic promoter.

In one embodiment, the inducer is anhydrotetracycline (aTC), which binds to tetR and decreases tetR affinity for the tetO2 response element. In certain aspects, the level of expression of the coding region of interest is dependent upon the amount or concentration of the inducer that is administered to the cell. For example, as described elsewhere herein, about a 3-fold range in expression of the coding region can be achieved by varying the amount or concentration of the inducer.

In some embodiments, the method provides for in vitro or ex vivo expression of the coding region of interest. For example, in some embodiments, the cell is induced to express an RNA, peptide or polypeptide from the coding region of interest in an in vitro or ex vivo environment. Induced expression can be used to investigate the role of the encoded RNA, peptide or polypeptide in cell function, including but not limited to cell growth, cell differentiation, host health, host pathology, or interaction of the cell with another cell or type of cell. For example, in some embodiments, the cell is cultured together with intestinal epithelial cells to investigate the role of the encoded RNA, peptide or polypeptide in the interaction between the cell and intestinal epithelial cells.

In some embodiments, the cell which has been induced to express a RNA, peptide or polypeptide from the coding region of interest is administered to a subject.

In some embodiments, the method provides for in vivo expression of the coding region of interest. In some embodiments a cell can be modified in vitro and then administered to a subject, where expression of an RNA, peptide or polypeptide from the coding region of interest is then induced in vivo. In one embodiment, the cell is modified in vivo and expression of an RNA, peptide or polypeptide from the coding region of interest is induced in vivo.

In some embodiments, the intestinal mucosal surface of a subject is contacted with the cell. In some embodiments, the cell is administered to a subject so that the cell contacts the intestinal mucosal surface of the subject. The cell may be administered to the subject via any suitable route, including, but not limited to, oral, rectal, or topical administration.

The cell may administered to any subject, including but not limited to a mammal, such as a mouse, rat, hamster, guinea pig, rabbit, cat, sheep, dog, pig, horse, cattle, primate, and human. In some embodiments, the controlled gene expression of the present invention allows for the in vitro, ex vivo, or in vivo investigation of the biological activity of the encoded RNA or peptide. For example, in one embodiment the method allows for controlled expression of an RNA, peptide or polypeptide in the gastrointestinal tract of the subject, including the intestine of the subject, to investigate the role of the RNA, peptide or polypeptide in bacterial growth and activity, bacteria-host interaction, host health, host inflammation, and the like. In some embodiments, the controlled gene expression of the present invention allows for the in vivo delivery of a therapeutic RNA, peptide or polypeptide to a subject to which the cell was administered. For example, in one embodiment, the method provides for in vivo production and delivery of a therapeutic RNA or peptide from a bacterial cell to the gastrointestinal tract of the subject, including the intestine of the subject.

In some embodiments, the method comprises administering a bacterial cell comprising a nucleic acid molecule comprising a synthetic promoter operably linked to a coding region of interest to a subject. For example, in some embodiments, the method comprises administering to the subject an amount of a probiotic composition comprising an amount of at least one type of bacteria, or a combination of several types of bacteria, where at least one of the bacteria comprises a nucleic acid molecule comprising a synthetic promoter operably linked to a coding region of interest to a subject.

In some embodiments, the bacteria administered according to the methods of the invention are live bacteria. One or several different types of bacteria can be administered concurrently or sequentially. Such bacteria can be obtained from any source, including being isolated from a microbiota and grown in culture using known techniques.

In some embodiments, the administered bacteria used in the methods of the invention further comprise a buffering agent. Examples of useful buffering agents include sodium bicarbonate, milk, yogurt, infant formula, and other dairy products.

Administration of a bacterium can be accomplished by any method suitable for introducing the organisms into the desired location. The bacteria can be mixed with a carrier and (for easier delivery to the gastrointestinal tract) applied to a liquid or to food. The carrier material should be non-toxic to the bacteria as well as to the subject. Preferably, the carrier contains an ingredient that promotes viability of the bacteria during storage. In various embodiments, the formulation also includes additional ingredients to improve palatability, improve shelf-life, impart nutritional benefits, and the like.

The dosage of the administered bacteria will vary widely, depending upon the frequency of administration, the manner of administration, the clearance of the bacteria from the host, and the like. In some embodiments, the initial dose may be larger, followed by smaller maintenance doses. The dose may be administered as infrequently as weekly or biweekly, or fractionated into smaller doses and administered multiple times daily, daily, semi-weekly, etc., to maintain an effective dosage level. It is contemplated that a variety of doses will be effective to achieve colonization of the gastrointestinal tract with the administered bacteria. In some embodiments, the dose ranges from about $10^6$ to about $10^{10}$ CFU per administration. In other embodiments, the dose ranges from about $10^4$ to about $10^6$ CFU per administration.

While it is possible to administer a bacteria for therapy as is, it may be desirable to administer it in a pharmaceutical formulation, e.g., in admixture with a suitable pharmaceutical excipient, diluent or carrier selected with regard to the intended route of administration and standard pharmaceutical practice. The excipient, diluent and/or carrier must be "acceptable" in the sense of being compatible with the other ingredients of the formulation and not deleterious to the subject. Acceptable excipients, diluents, and carriers for therapeutic use are well known in the pharmaceutical arts, and are described, for example, in Remington: The Science and Practice of Pharmacy. Lippincott Williams & Wilkins (A. R. Gennaro edit. 2005). The choice of pharmaceutical excipient, diluent, and carrier can be selected with regard to the intended route of administration and standard pharmaceutical practice.

Although there are no physical limitations to delivery of the formulations of the present invention, oral delivery is preferred for delivery to the gastrointestinal tract because of its ease and convenience, and because oral formulations readily accommodate additional mixtures, such as milk, yogurt, and infant formula. For delivery to lower gastrointestinal tract, the bacteria can be administered rectally or by enema.

In some embodiments, the in vivo induction of gene expression comprises administering the inducer to the subject. The inducer may be administered to the subject by any suitable means, including, but not limited to oral, rectal, topical, or parenteral administration. The dosage of the inducer will vary widely, depending upon the frequency of administration, the manner of administration, the clearance of the inducer from the subject, and the like.

Methods of Generating Mutations

In one embodiment, the present invention provides for regulated expression of a protein or peptide that is toxic in a cell through the use of a synthetic promoter described herein. In some embodiments, the method comprises administering to a cell a nucleic acid molecule comprising a synthetic promoter described herein operably linked to at least one protein or peptide that can be used in a method of selection or counter-selection of a host cell. In one embodiment, the method comprises administering to the cell a repressor, which prevents expression from the coding region of interest. In one embodiment, the cell expresses a repressor, which prevents expression from the coding region of interest. In one embodiment, the method comprises administering to the cell a nucleic acid molecule that expresses the repressor. For example, in one embodiment, the method comprises administering to the cell a vector comprising a) a synthetic promoter operably linked to a protein or peptide that is toxic to the cell; and b) a nucleic acid encoding a repressor. In some embodiments, the synthetic promoter operably linked to a protein or peptide that is toxic to the cell and the nucleic acid encoding the repressor are on the same nucleic acid molecule. In other embodiments, the synthetic promoter operably linked to the coding region of interest and the nucleic acid encoding the repressor are on different nucleic acid molecules.

In some embodiments, the method comprises administering an inducer to the cell to induce expression of the protein or peptide that is toxic to the cell. In some embodiments, the inducer is an inhibitor of the repressor. In various embodiments, the inducer is any suitable inhibitor of the repressor, including but not limited to, a nucleic acid molecule, siRNA, protein, antibody, small molecule, or the like, which inhibits the expression or activity of the repressor. In some embodiments, the inducer binds to the repressor and prevents the repressor from binding the repressor response element of the synthetic promoter.

In one embodiment, the inducer is anhydrotetracycline (aTC), which binds to tetR and decreases tetR affinity for the tetO2 response element. In certain aspects, the level of expression of the coding region of interest is dependent upon the amount or concentration of the inducer that is administered to the cell. For example, as described elsewhere herein, about a 3-fold range in expression of the coding region can be achieved by varying the amount or concentration of the inducer.

In one embodiment, expression of the protein or peptide that is toxic to the cell results in cell death of the cell that has been modified to contain the expression cassette or vector of the invention.

In one embodiment, the expression cassette comprising at least one protein or peptide that is toxic to the host cell under the inducible promoter of the invention is incorporated into the genome of the host cell, for example through recombination of a nucleotide sequence cloned into a multiple cloning site of a vector of the invention with a target genomic nucleotide sequence. Such an embodiment, can be used for selecting cells in which the target genomic nucleotide sequence has undergone an additional mutational event such that the expression cassette is eliminated from the host cell's genome or alternatively silenced. This method can be used, for example to generate deletions in a host cells genome that results in deletion or mutation of a target gene in the host cell. Therefore, in one embodiment, the invention provides methods of genetic engineering to generate deletions, mutations or variations in a target nucleic acid molecule comprising the steps of: administering to a host cell a vector comprising a) a synthetic promoter operably linked to a protein or peptide that is toxic to the cell; and b) a nucleic acid encoding a repressor, wherein the vector further comprises a nucleotide sequence having at least 80% homology to a target nucleotide sequence of the host cell, such that the expression cassette is integrated into the host cell's genome, c) administering an inducer to the cell to induce expression of the protein or peptide that is toxic to the cell. In this method, cells that have generated a mutation or have undergone a recombination event to remove the expression cassette are viable whereas cells that have not have reduced viability.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore are not to be construed as limiting in any way the remainder of the disclosure.

Example 1: Materials and Methods

Microbial Strains and Growth Conditions

All strains used are listed in Table 3 (below). All *Bacteroides thetaiotaomicron* and *Bacteroides ovatus* strains used were derivatives of *B. thetaiotaomicron* VPI-5482 or *B. ovatus* ATCC 8483 (NCBI Taxonomy ID: 411476), respectively, carrying a deletion in the tdk gene (Larsbrink, J. et al., 2014, Nature, 506:498-502; Martens, E. C. et al., 2008, Cell Host and Microbe, 4:447-457), except for the date depicted in FIG. 5, which used wildtype strains. *Bacteroides* strains were cultured anaerobically at 37° C. in liquid TYG media (10 g/L tryptone, 5 g/L yeast extract, 10 mM glucose, 100 mM potassium phosphate buffer (pH 7.2), 20 mg/L $MgSO_4$-$7H_2O$, 400 mg/L $NaHCO_3$, 80 mg/L NaCl, 0.0008% $CaCl_2$, and 4 µg/mL $FeSO_4$-$7H_2O$, 10 mg/L hemin (Sigma), 0.5 g/L cysteine and 1 mg/L vitamin K3), Gut Microbiota Medium (for FIG. 5) (10 g/L tryptone, 5 g/L yeast extract, 2.2 mM glucose, 2.9 mM cellobiose, 2.8 mM maltose, 2.2 mM fructose, 5 g/L meat extract, 100 mM potassium phosphate buffer (pH 7.2), 20 mg/L $MgSO_4$-$7H_2O$, 400 mg/L $NaHCO_3$, 80 mg/L NaCl, 0.0008% $CaCl_2$, and 4 µg/mL $FeSO_4$-$7H_2O$, 10 mg/L hemin (Sigma), 0.5 g/L cysteine and 1 mg/L vitamin K3, 0.05% Tween 80, 10 mL/L ATCC Vitamin Mix, 10 mL/L ATCC Trace Mineral Mix, 30 mM acetic acid, 1 mM isovaleric acid, 8 mM propionic acid, 4 mM butyric acid) (Goodman et al., 2011a), or on brain heart infusion (BHI; Becton Dickinson) agar supplemented with 10% horse blood (Quad Five). Cultures were grown and manipulated in an anaerobic chamber (Coy Laboratory Products) with an atmosphere of 20% $CO_2$, 10% $H_2$, and 70% $N_2$ at 37° C. *E. coli* strains EC100D pir-116 and S17-1 lambda pir were used for propagation and transfer, respectively, of R6K pir plasmids. *E. coli* strains were grown aerobically in LB medium at 37° C. When required, antibiotics were added to the medium as follows: carbenicillin 100 µg/mL, gentamicin 200 µg/mL, and erythromycin 25 µg/mL. Anhydrotetracycline (aTC; Cayman Chemicals) was dissolved in 100% ethanol at 2 mg/mL as a master stock. Working stock solutions of aTC were made at 1,000× in 100% ethanol.

Human Studies

Recruitment of healthy human volunteers, sample collection, anaerobic processing, and −80° C. storage of fecal samples in cryoprotectant under anaerobic conditions was previously described (Cullen, T. W. et al., 2015, Science, 347:170-175).

Animal Experiments

Germ-free Swiss Webster mice were maintained in flexible plastic gnotobiotic isolators with a 12-hour light/dark cycle and provided a standard, autoclaved mouse chow (5K67 LabDiet, Purina) ad libitum and autoclaved water for the duration of the experiment. Filter-sterilized aTC was added to drinking water stored in red-tinted bottles (Ancare, #PC9RH8.5RD) to inhibit degradation by light. Mice were co-housed for the duration of the experiments. Cage changes were always carried out when aTC was withdrawn from drinking water. Fecal and luminal samples were collected and processed in 2.0 mL screw cap tubes (Axygen Scientific; #SCT-200-C). Germ free status was monitored by 16S rDNA-targeted PCR of fecal DNA and anaerobic and aerobic culture of fecal samples.

Sequence Conservation in 16S Promoters

Genomic sequences of 19 different *Bacteroides* strains (Table 1) were searched using BLAST (Altschul, S. F. et al., 1990, Journal of Molecular Biology 215:403-410) for 16S rRNA loci using the *B. thetaiotaomicron* VPI-5482 (NBCI Taxonomy ID: 226186) 16S rRNA sequence as a query. For each 16S rRNA locus identified, upstream regions (up to 1000 base pairs) were manually searched for the RNA polymerase recognition sequence, TTTG(N$_{19-21}$) TANNTTTG (SEQ ID NO:96) (Mastropaolo, M. D., et al., 2009, Microbiology, 155:2683-2693). The fifth nucleotide downstream of the −7 element is a conserved cytosine residue and shown to be the transcription start site (Mastropaolo, M. D., et al., 2009, Microbiology, 155:2683-2693). This cytosine residue and the upstream 67 nucleotides were designated as a 16S rRNA promoter. In total, 182 promoters were identified and frequency logos generated for each nucleotide position using WebLogo3 (Crooks, G. E. et al., 2004, Genome Research, 14:1188-1190).

Genetic Parts

Genetic parts (promoters, ribosome binding sites (RBSs), localization signal) developed in this study are listed in Table 2. RBSs strength correlates with a complex set of features, including enrichment in adenine and thymine, secondary structure, and potential interactions with the ribosomal protein S1 (Accetto, T. et al., 2011, PLoS ONE, 6:e22914-e22919; Mimee, M. et al., 2015, Cell Syst., 1:62-71; Wegmann, U. et al., 2013, Appl. Environ. Microbiol., 79:1980-1989). Alternate RBSs of varying strengths (Mimee, M. et al., 2015, Cell Syst., 1:62-71; Wegmann, U. et al., 2013, Appl. Environ. Microbiol., 79:1980-1989), were used in this study.

Molecular Cloning

The plasmids used in this study are listed in Table 3. The template P1 and P2 promoters containing the ribosome binding site GH023 were synthesized by Integrated DNA Technologies (IDT). DNA amplification for cloning procedures were carried out using Q5 High Fidelity DNA Polymerase (New England Biolabs), and colony PCR was carried out using OneTaq DNA Polymerase (New England Biolabs). Splicing by Overlap Extension (SOE) PCR (Bryksin, A. V. et al., 2010, Biotech., 48:463-465) was utilized to insert or replace genetic parts (tetO2 or RBSs) of the parental P1 and P2 promoters, followed by Gibson cloning (HiFi DNA Assembly Master Mix, New England Biolabs). All vectors containing P1 and P2 promoters and their derivatives were built to contain an NcoI restriction site at the ATG site and a SalI restriction site further downstream. For insertion of reporters downstream of the variant promoters, vectors were digested with both NcoI and SalI, and reporters were inserted using Gibson cloning. Genetic modifications generated on plasmids and *Bacteroides* strains were verified by sequencing.

Integration of pNBU2 Vectors into *Bacteroides*

Single-copy introduction of pNBU2 vectors into *Bacteroides* sp. genomes and determination of genomic insertion site location was carried out as previously described (Koropatkin, N. M. et al., 2008, Structure, 16:1105-1115; Larsbrink, J. et al., 2014, Nature, 506:498-502; Martens, E. C. et al., 2008, Cell Host and Microbe, 4:447-457), with minor modifications described below.

For *Bacteroides* type strains, overnight cultures of *E. coli* S17-1 donor strains were diluted 1,000-fold in LB medium containing carbenicillin and *Bacteroides* recipients diluted 250-fold in TYG medium and each grown to early exponential phase (OD$_{600}$ 0.2-0.3). Donor and recipient strains were combined at a 1:10 donor:recipient culture volume ratio, centrifuged at 4,000 rpm for 20 minutes, resuspended in 100 µL of BHI liquid medium and plated as a dime-sized puddle on non-selective BHI-blood agar plates for 20 hours at 37° C. under aerobic conditions to allow for conjugation. Mating lawns were resuspended in 1 mL 1× phosphate buffered saline (PBS) and transconjugants selected by plating serial dilutions on BHI-blood agar plates containing gentamicin and erythromycin. Insertion site location was verified by PCR (primers provided in Table 3).

For *Bacteroides* isolates cultured directly from humans, the same procedure was used except equal volumes of donor (*E. coli* S17-1 pNBU2[Erm]TetR-P1T$_{DP}^{GH023}$-NanoLuc) and recipient overnight cultures were combined and 100 µL plated on BHI-blood agar plates for the conjugation step. After 20 hours of aerobic incubation at 37° C., transconjugants were selected on gentamicin and erythromycin as above. For each human isolate, 4 separate clones were colony purified on the same media and directly inoculated into Gut Microbiota Medium to test the performance of the P1T$_{DP}$ platform.

Construction of Bt::tetR and Bt$^{RS}$

A constitutively-expressing tetR construct was built by splicing 300 base pairs of the BT1311 (rpoD; σ$^{70}$) promoter (Table 2) to the tetR gene. To identify a neutral location in the *B. thetaiotaomicron* genome for stable integration of the tetR cassette, an intergenic region was searched for between the 3' ends of two genes, where disruption of either gene or the intergenic region itself by transposon insertion confers no fitness defect or benefit in rich or minimal medium, or in gnotobiotic mice mono-associated with *B. thetaiotaomicron* or colonized with multi-species communities (Goodman, A. L. et al., 2009, Cell Host and Microbe, 6:279-289). Constructs were integrated into the *B. thetaiotaomicron* genome by conjugation as described below. For strain Bt::tetR, the tetR cassette was placed between genomic position 4861701 and 4861702 (between BT3743 and BT3744).

For strain Bt$^{RS}$, repression of sialidase activity likely confers a fitness cost to the organism (Ng, K. M. et al., 2013, Nature, 502:96-99). Consequently, three constitutive tetR constructs were placed in the chromosome to reduce the risk of selecting spontaneous mutants in tetR. In addition to the construct located between BT3743 and BT3744, two additional exact copies of the construct were placed between genomic position 2660693 and 2660694 (between BT2113 and BT2114), and between genomic position 6193956 and 6193957 (between BT4719 and BT4720), generating strain Bt::3xtetR.

Unmarked Chromosomal Modifications

Unmarked chromosomal modifications, including the insertion of the constitutively-expressing tetR cassette(s), in-frame deletions of BT1754 and BT0455, replacement of the BT1754 promoter with $P1T_{DP}^{GH023}$, and replacement of the BACOVA_04598 promoter with $TetR-P1T_{DP}^{B1}$, were generated using a counterselectable allelic exchange procedure (Koropatkin, N. M. et al., 2008, Structure, 16:1105-1115). Approximately 1,000-basepair regions flanking the genomic region to be modified were amplified by PCR, joined using Gibson cloning or SOE PCR, and cloned into pExchange-tdk. Sequence-verified plasmids were introduced into Bacteroides as above, except a 1:1 donor:recipient culture volume ratio was used for conjugation. Bacteroides transconjugants (merodiploids) were selected after conjugation by dilution plating on BHI-blood agar plates containing gentamicin and erythromycin. Insertion of the pExchange-tdk vector upstream or downstream of the genomic region of interest was verified by colony PCR. Merodiploids harboring appropriate integration of the pExchange-tdk vector were grown in liquid TYG overnight, and plated onto BHI-blood agar containing 200 µg/mL 5-fluoro-2-deoxy-uridine (FUdR) (Abcam) to select for the loss of the pExchange-tdk vector. Individual clones were further verified for erythromycin sensitivity and FUdR resistance. Erythromycin-sensitive, FUdR-resistant clones were screened for the appropriate genetic manipulation by PCR and verified by sequencing.

Luciferase Assay from In Vitro Samples

The NanoLuc luciferase assay was performed as described (Mimee, M. et al., 2015, Cell Syst., 1:62-71), with the following modifications. All strains were first grown for 18 hours in TYG medium or Gut Microbiota Medium and diluted 250-fold into fresh medium in appropriate conditions (with or without aTC). Cultures were grown to mid exponential phase ($OD_{600}$ 0.3-0.4) and colony forming units (CFU) were measured by dilution plating. 500 µL of the culture was centrifuged at 21,130×g for 3 minutes, resuspended in 50 µL 1× BugBuster (Novagen) in 1×PBS and lysed by one cycle of freeze-thaw and nutation at 26° C. for 10 minutes. Lysates were cleared of cellular debris by centrifugation at 21,130×g for 10 minutes at 4° C. 10 µL of the supernatant was mixed with an equal volume of Nano-Luc Reaction Buffer using the Nano-Glo Luciferase Assay System (Promega) and incubated for 5 minutes at 26° C. to induce luminescence production. Relative Light Units (RLU) were measured using a fluorescence plate reader (BioTek Synergy H1) with an integration time of 1 second at a gain setting of 100. Luminescence values were normalized to colony forming units (CFUs) because experimental conditions (e.g., growth medium, antibiotics, aTC, heterologous gene expression) affect the correlation between CFUs and $OD_{600}$ in Bacteroides.

Polymyxin B Susceptibility

Minimum inhibitory concentrations (MICs) were determined on solid medium using E-test strips (Biomerieux) as previously described (Cullen, T. W. et al., 2015, Science, 347:170-175), except that cultures were initially grown for 18 hours in liquid medium. Cultures were adjusted to $OD_{600}$~1.0 and 100 µL of cell suspension was then spread onto BHI-blood agar plates. Surface liquid was allowed to dry in a fume hood for 10 minutes, followed by application of the E-test strip to the agar surface. Plates were incubated anaerobically at 37° C. for 24 hours before scoring the MIC.

Isolation of Bacteroides from Humans

Bacteroides isolates were enriched by plating dilutions of the fecal material on Brucella Laked Blood Agar containing Kanamycin and Vancomycin (BD #297840). After 48 hours anaerobic incubation at 37° C., candidate Bacteroides isolates were selected and cultured in Gut Microbiota Medium for DNA isolation by the cetyltrimethylammonium bromide (CTAB) method (Wilson, K., 2001, Curr. Protoc. Mol. Biol., Chapter 2:2.4.1-2.4.5) and −80° C. storage in cryoprotectant. 16S rDNA was amplified and sequenced from each isolate using primers 8F and 1492Rm (Table 3). The taxonomy of the isolate was identified by BLAST (Altschul, S. F. et al., 1990, Journal of Molecular Biology, 215:403-410) using the sequenced 16S rDNA and designated as the most closely related species. In each case, isolate 16S sequences were within 97% identity of a known species. A phylogenetic tree of sequenced 16S rDNA from the isolates and type strains was generated using Phlogeny.fr (Dereeper, A. et al., 2008, Nucleic Acids Research, 36:W465-W469; Dereeper, A. et al., 2010, BMC Evol. Biol., 10:8).

BT1754-Dependent Growth Assay

Minimal media was made as previously described (Martens, E. C. et al., 2008, Cell Host and Microbe, 4:447-457), but with the addition of 1 g/L $Na_2CO_3$, 10 mg/L $MnCl_2$-$4H_2O$, and 10 mg/L $CoCl_2$-$6H_2O$. Glucose or fructose was added as the sole carbon source at a final concentration of 0.5%. Cultures were grown in minimal medium containing glucose for 18 hours and diluted 1:1000 in minimal medium containing either glucose or fructose with or without 100 ng/mL aTC. Cultures were incubated anaerobically at 37° C. in clear flat bottom 96-well plates (Costar #3595) and growth was monitored ($OD_{600}$) every 15 minutes in a plate reader (BioTek Eon). Cell doublings per hour were calculated as $(\log(OD_{600}^{final})-\log(OD_{600}^{initial}))/(duration \times \log(2))$ from cultures during exponential phase of growth ($OD_{600}$~0.15 to ~0.4).

Periplasmic Targeting of T6SS Effectors

To direct Bte1 and Bfe1 to the periplasm upon expression in B. thetaiotaomicron, the genes encoding each effector were first PCR amplified from genomic DNA purified from B. fragilis NCTC 9343 and B. fragilis 638R, respectively, using the CTAB method. A periplasmic localization signal was searched for that would be cleaved after translocation to prevent steric hindrance of the effector. To identify proteins that encode N-terminal B. thetaiotaomicron periplasmic localization signals that are post-translationally cleaved after protein translocation, the proteome of the Bacteroides thetaiotaomicron VPI-5482 chromosome was searched for signal peptides (PTM/Processing; Molecule Processing, Signal Peptide) using UniProt (UniProt Consortium, 2015, Nucleic Acids Research, 43:D204-D212). To exclude membrane proteins that potentially encode an uncleaved signal peptide, the search was refined by an additional query for the term "periplasmic" under Protein name. To identify a short periplasmic signal, the maximum length for the signal peptide was set at 20 amino acids. BT4676, which encodes a hypothetical protein, gave the highest confidence value in predicting both a periplasmic-localized signal peptide and the position of cleavage (between amino acid 20 and 21) according to SignalP (Petersen, T. N. et al., 2011, Nat. Meth., 8:785-786). Therefore, the B. fragilis effectors were fused at the 5' end (minus the ATG start codon) to the first 63 base pairs (encoding the first 21 amino acids) of the BT4676 open reading frame (see Table 2 for sequence) in order to localize them to the periplasm after expression in *B. thetaiotaomicron*.

Monocolonized Gnotobiotic Mice

Germ-free Swiss Webster mice were orally gavaged with $1\times10^9$ CFU of Bt::tetR P1T$_{DP}^{GH023}$-NanoLuc and colonization was allowed to stabilize for at least 7 days prior to the start of the experiment. Fecal pellets were collected every day, and groups of mice were given aTC in the drinking water at various concentrations for 48 hours after stool collection on Day 3 and Day 17. Mice belonging to the same treatment group were co-housed for the duration of the experiment. To obtain samples for luminescence production, fecal pellets and intestinal lumen (~100-200 mg) were homogenized in 1 mL of 1×PBS with a single 5 mm stainless steel bead using a bead beater (BioSpec Products) at 26° C. for 1 minute on the high setting, followed by vortexing at top speed for 8 minutes. Samples were centrifuged at 500×g for 1 minute to pellet fibrous and insoluble matter. The supernatant was used for CFU determination by plating dilutions on BHI-blood agar plates containing gentamicin and erythromycin, and 500 μL was used for luminescence measurements (described below).

Defined Human Gut Microbiota Gnotobiotic Mice

Figures 12A, 12B, 12C, 12D:
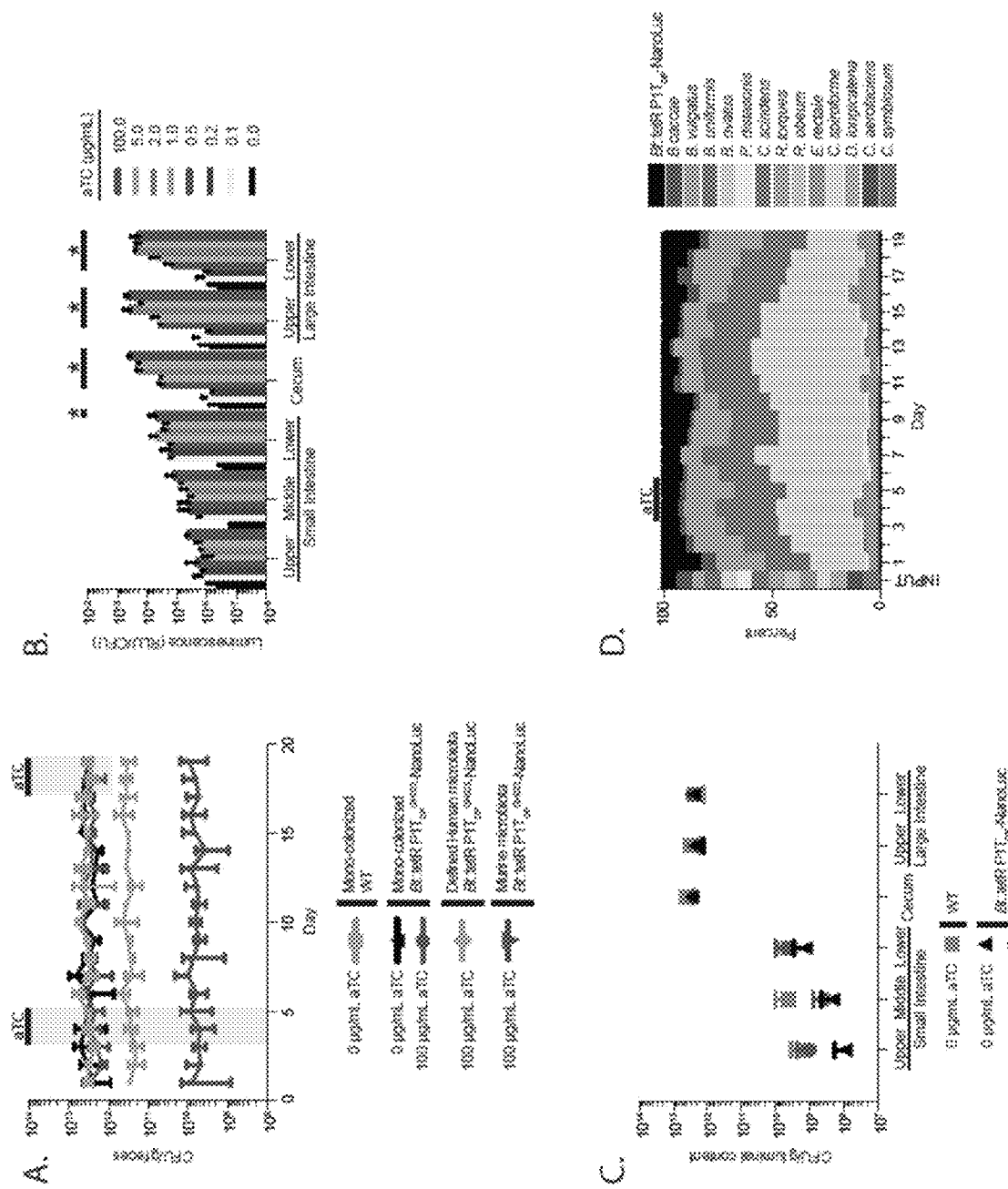

Germ-free Swiss Webster mice were orally gavaged with a mixture of $1\times10^8$ CFU of each of 14 human gut microbes shown in FIG. 12D and Table 3. With the exception of the reporter strain, all species are sensitive to gentamicin and/or erythromycin (data not shown). Colonization was allowed to stabilize for at least 7 days prior to the start of the experiment. Fecal pellets were collected daily, and mice were given aTC (100 μg/mL) in the drinking water for 48 hours after stool collection on Day 3. Fecal samples were homogenized, and fibrous/insoluble matter removed as described above. From the supernatant, 200 μL was stored for DNA purification as previously described (Goodman, A. L. et al., 2011, Nat. Protoc., 6:1969-1980) and subsequent qPCR analysis (described below), 10 μL was used for CFU determination of the reporter strain by plating dilutions on BHI-blood agar plates containing gentamicin and erythromycin, and 500 μL was used for luminescence measurements (described below).

At each time point, abundance of each species was assessed by qPCR from fecal DNA using strain specific primers described previously (Cullen, T. W. et al., 2015, Science, 347:170-175). qPCR was performed as described (Goodman, A. L. et al., 2009, Cell Host and Microbe, 6:279-289; Martens, E. C. et al., 2008, Cell Host and Microbe, 4:447-457) using a CFX96 instrument (BioRad) and SYBR FAST universal master mix (KAPA Biosystems). Mean strain quantities were calculated using a standard curve.

SPF Rag$^{-/-}$ Conventional Mice 8-10 week old SPF Rag$^{-/-}$ mice (Jackson Laboratories) (n=7) were colonized by oral gavage with $1\times10^9$ CFU of *B. thetaiotaomicron* TetR-P1T$_{DP}^{GH023}$-NanoLuc. Fecal pellets were collected daily after gavage and processed as described above. The supernatant was used for CFU determination by plating dilutions on BHI-blood agar plates containing gentamicin and erythromycin, and 500 μL was used for luminescence measurements (described below). Culturing of bacteria from fecal pellets obtained from these animals prior to gavage confirms that they do not harbor native species resistant to gentamicin and erythromycin (data not shown).

Luciferase Assay from Murine Samples

The 500 μL collected from the resuspended fecal supernatant was centrifuged at 21,130×g for 3 minutes to pellet bacterial cells, which were then resuspended in 50 μL 1× BugBuster (Novagen) in 1×PBS and lysed by one round of freeze-thaw and 10 minutes of nutation at 26° C. Samples were centrifuged at 21,130×g for 10 minutes at 4° C., and 10 μL of the supernatant was mixed with an equal volume of NanoLuc Reaction Buffer to induce luminescence production. Luminescence was measured after a 5 minute incubation at 26° C. on a plate reader (BioTek Synergy H1) with an integration time of 1 second at a gain setting of 100. Luminescence values were normalized to colony forming units (CFUs) determined by dilution plating of the resuspended fecal supernatant on BHI-blood agar plates containing gentamicin and erythromycin.

Sialic Acid and aTC in Murine Samples

Groups of 6 germ-free Swiss Webster mice were orally gavaged with $1\times10^9$ CFU of the desired *B. thetaiotaomicron* strain. Fecal samples (~100-200 mg) were collected daily for 12 days. aTC (100 μg/mL) was administered in drinking water for 12 hours after fecal collection on day 1. Fecal samples were homogenized in 1 mL of 1× tris-buffered saline (TBS) with a single 5 mm stainless steel bead using a bead beater (BioSpec Products) at 26° C. for 1 minute on the high setting, followed by vortexing at top speed for 8 minutes. Samples were then centrifuged at 500×g for 1 minute to pellet fibrous and insoluble matter. Bacterial cells from 600 μL of the supernatant was isolated through centrifugation at 21,130×g for 3 minutes, resuspended in 50 μL of Sialidase Reaction buffer (50 mM Tris-HCl pH 7.0, 5 mM EDTA) containing 1× BugBuster, and stored at −80° C. for ex vivo sialidase measurements (described below).

To the remaining material, 400 mg of 0.1 mm glass beads was added and further homogenized by bead beating for 2 minutes. Insoluble material was pelleted by centrifuging the sample for 3 minutes at 21,130×g, and 20 μL of the supernatant was used for mass spectrometry measurements of sialic acid and aTC by liquid chromatography coupled tandem mass spectrometry (QqQ) and mass spectrometry (qTOF), respectively.

For sialic acid measurements, 5 μL of internal standard solution (50 μM 1,2,3-$^{13}$C$_3$ sialic acid in H$_2$O) were added to each sample (20 μL) and proteins were precipitated through addition of 100 μL organic solvents at −20° C. (acetonitrile:methanol, 1:1). After incubation at −20° C. for 1 h, samples were centrifuged at 4,000×g for 15 min and 100 μL supernatant was collected, dried under vacuum at 22° C., and re-suspended in 32 μL H$_2$O. LC-MS/MS analysis was carried out using an Agilent 1290 UHPLC system coupled to an Agilent 6490A QqQ mass spectrometer. Chromatographic separation was performed on a BEH Amide column (Waters, 150 mm×2.1 mm, 1.7 μm particle size) using mobile phase A: H$_2$O, 0.1% formic acid and B: acetonitrile, 0.1% formic acid at 45° C. 2 μL of processed sample were injected at 99% B and 0.4 mL/min flow followed by a linear gradient to 70% B over 10 min and 0.4 mL/min flow, leading to sialic acid elution at 6.5 min. The column was re-equilibrated at starting conditions for 8 min. The QqQ was operated in negative ionization mode using dynamic MRM scans with the following source parameters: VCap: 3500 V, nozzle voltage: 2000 V, gas temp: 275° C.; drying gas 12 L/min; nebulizer: 35 psig; sheath gas temp 275° C.; sheath gas flow 12 L/min. MRM parameters were optimized following the manufacturer's recommendation: Sialic acid 308.1 m/z to 58.8, 87, 97, 9, 118.9, and 169.9 m/z with respective collision energies 33, 13, 29, 9, 13 (au). Corresponding settings were used for the 1,2,3-$^{13}$C$_3$ sialic acid standard. The MassHunter Quantitative Analysis Software (Agilent, version 7.0) was used for peak integration with the most abundant ion fragment as quantifier and the others as qualifiers of the peak. Quantification was based on calibration curves using commercially available sialic acid and the signal intensity of the internal standard spiked into each sample.

For aTC measurements, 5 μL of internal standard solution (0.25 μM sulfamethoxazole and caffeine in $H_2O$) were added to each sample (20 μL) and further processed as described above. Dried samples were re-suspended in 4 μL methanol and diluted in 12 μL $H_2O$. Chromatographic separation was performed on a C18 Kinetex Evo column (Phenomenex, 100 mm×2.1 mm, 1.7 μm particle size) using mobile phase A: $H_2O$, 0.1% formic acid and B: methanol, 0.1% formic acid at 45° C. 10 μL of sample were injected at 100% A and 0.4 mL/min flow followed by a linear gradient to 95% B over 5.5 min and 0.4 mL/min flow leading to aTC, caffeine and sulfamethoxazole elution at 3.0, 1.9, 2.1 min, respectively. The qTOF was operated in positive scanning mode (50-1000 m/z) and the following source parameters: VCap: 3500 V, nozzle voltage: 2000 V, gas temp: 225° C.; drying gas 13 L/min; nebulizer: 20 psig; sheath gas temp 225° C.; sheath gas flow 12 L/min. Online mass calibration was performed using a second ionization source and a constant flow (5 μL/min) of reference solution (121.0509 and 922.0098 m/z). Compounds were identified based on the retention time of chemical standards and their accurate mass (tolerance 20 ppm). The MassHunter Quantitative Analysis Software (Agilent, version 7.0) was used for peak integration and quantification was based on calibration curves using chemical standards and the signal intensity of the internal standard spiked into each sample.

Sialidase Activity in Murine Samples

Bacterial cells (collected and stored as described above) were lysed through one round of freeze-thaw followed by nutation for 10 minutes at 26° C. Cell lysates, which contained sialidase activity, were obtained from the supernatant after centrifugation at 21,130×g for 10 minutes at 4° C. The reaction to determine sialidase activity was performed in a total volume of 100 μL consisting of 72 μL Sialidase Reaction Buffer, 10 μL of 100 mM of substrate 2-O-(p-Nitrophenyl)-t-D-N-acetylneuraminic acid (pNP-SA; Sigma-Aldrich) resuspended in Sialidase Reaction Buffer, and 18 μL of cell lysate. The reaction mixture was incubated at 37° C. and 10 μL of the reaction was transferred to an equal volume of ice-cold acetonitrile at 0, 5, 10, 15, 20, 25, 30, and 60 minutes to stop the reaction. 5 μL of internal standard solution (1 μM sulfamethoxazole and caffeine in $H_2O$) were added to each sample (20 μL) and further processed as described above. Dried samples were re-suspended in 6 μL methanol followed by the addition of 26 μL $H_2O$ and further dilution (1:4) in $H_2O$. Quantification of the enzyme reaction product, p-nitrophenol (pNP), was identical to the LC-MS analysis of aTC described above, but with reduced injection volume (5 μL) and methanol replacing acetonitrile as solvent B for the reversed phase chromatography. Retention time of pNP was 2.1 min and a commercially available standard was used for the calibration curve. Linear fits of pNP were performed for at least the first 10 min of the enzyme reaction using the 'polyifit' function of Matlab R2016a (Mathworks). Linear fit values were normalized to amount of protein in the cellular lysates added to each reaction, which was determined by Bradford.

A best fit line (FIG. 7D) based on Michaelis-Menten kinetics was created (Prism 6) on data plotting sialic acid levels (FIG. 7C) against fecal sialidase activity (FIG. 7B) from fecal pellets collected daily between Day 0 (prior to aTC administration) and Day 6 (when sialidase activity becomes undetectable) from mice carrying the $Bt^{RS}$ strain (n=4 mice).

Quantification and Statistical Analysis

Datasets were analyzed within the GraphPad Prism 6 software. Pairwise comparisons were generated with two-tailed t tests. P values and n values are indicated.

Analysis of Defined Microbial Communities

Relative abundance calculations based on qPCR were used to construct an OTU table for alpha and beta diversity analyses in QIIME v1.8 (Caporaso, J. G. et al., 2010, Nat. Meth., 7:335-336). Alpha diversity (Simpson, Shannon, and Simpson_e metrics) was compared between day 3 (immediately prior to aTC administration) and each other day using a paired Student's t-test and a p-value cutoff of 0.05; no significant differences were found regardless of multiple hypothesis testing correction. Beta diversity analysis was conducted using Hellinger distances.

Example 2: Engineered tetO2-Containing Promoters Maintain High Levels of Gene Expression Highly active, broadly conserved *Bacteroides* promoters provide an ideal template for a regulated gene expression platform for these organisms. *B. thetaiotaomicron* RNA-seq experiments indicate that 16S rDNA promoter activity can produce 20-30% of total cellular RNA, consistent with other bacteria (Dennis, P. P. et al., 2008, EcoSal Plus, 3:1-49; Rey, F. E. et al., 2010, J. Biol. Chem., 285:22082-22090). Because the P1 promoter sequence upstream of the *B. thetaiotaomicron* 16S rDNA gene BT_r09 is known to function in other *Bacteroides* (Wegmann, U. et al., 2013, Appl. Environ. Microbiol., 79:1980-1989), this sequence provides an ideal template for a regulated gene expression platform in this genus.

Intergenic regions upstream of *Bacteroides* 16S rDNAs generally contain two RNAP binding regions capable of initiating transcription, designated P1 (located farthest upstream of the 16S rDNA coding region) and P2 (Mastropaolo, M. D. et al., 2009, Microbiology, 155:2683-2693). Frequency logos generated from 182 16S rDNA promoters representing 74 different 16S rDNA loci across 19 genome-sequenced *Bacteroides* species reveal several highly conserved sequence elements (FIG. 1A, Table 1).

TABLE 1

Name and strain IDs of species used for identifying promoter regions upstream of 16S rRNA

| Species | NCBI Taxonomy ID |
| --- | --- |
| *Bacteroides caccae* CL03T12C61 | 997873 |
| *Bacteroides cellulosilyticus* CL02T12C19 | 997874 |
| *Bacteroides dorei* CL02T00C15 | 997875 |
| *Bacteroides eggerthii* 1_2_48FAA | 665953 |
| *Bacteroides faecis* MAJ27 | 1077285 |
| *Bacteroides finegoldii* CL09T03C10 | 997888 |
| *Bacteroides fragilis* 638R | 862962 |
| *Bacteroides fragilis* NCTC 9343 | 272559 |
| *Bacteroides intestinalis* DSM 17393 | 471870 |
| *Bacteroides oleiciplenus* YIT 12058 | 742727 |
| *Bacteroides ovatus* CL02T12C04 | 997885 |
| *Bacteroides plebeius* DSM 17135 | 484018 |
| *Bacteroides salanitronis* DSM 18170 | 667015 |
| *Bacteroides salyersiae* CL02T12C01 | 997887 |
| *Bacteroides stercoris* ATCC 43183 | 449673 |
| *Bacteroides thetaiotaomicron* VPI-5482 | 226186 |
| *Bacteroides uniformis* CL03T00C23 | 997889 |
| *Bacteroides vulgatus* ATCC 8482 | 435590 |
| *Bacteroides xylanisolvens* CL03T12C04 | 997892 |

Consistent with other constitutive *Bacteroides* promoters, the 16S rDNA promoters encode strongly conserved −33 (TTTG) and −7 (TAnnTTTG) RNAP binding sites (Bayley, D. P. et al., 2000, FEMS Microbiol. Lett., 193:149-154; Mastropaolo, M. D. et al., 2009, Microbiology, 155:2683-2693). Upstream of the −33 element, repeated A-rich tracts are spaced 12-13 base pairs apart, consistent with these conserved sequences representing an UP-element which in *E. coli* stimulates transcription initiation (Gourse, R. L. et al., 2000, Mol. Microbiol., 37:687-695). Finally, conserved A/T-rich regions between the −33 and −7 elements may play an important role in RNAP binding and/or transcription activation. This analysis suggests permissive and restricted regions for manipulation of the promoter sequence.

To transform the constitutive BT_r09 P1 promoter into an inducible system, control elements that meet three key criteria were searched for. Most importantly, the inducer should not be present in undefined growth medium used to culture *Bacteroides* and other human gut anaerobes, nor in the gut or tissue of mice and other mammals, and not in standard animal diets (i.e., not a poly- or monosaccharide or analogue). Second, the inducer should not be toxic to *Bacteroides* at concentrations that permit maximal promoter activation nor be consumed as a carbon source or other nutrient. Third, the regulatory elements should be capable of repressing strong promoters, allowing deletion mutant phenotypes to be recapitulated when regulated gene(s) are repressed and permitting a wide range of expression levels in response to varying inducer concentration. The aTC-regulated control elements from the *E. coli* Tn10 transposon fit these three criteria (Bertram, R. et al. 2008, Microbial Biotechnology, 1:2-16). *Bacteroides* grow at wildtype rates in aTC concentrations typically used to control gene expression from tetracycline-regulated promoters (FIG. 8A) (Lutz, R. et al., 1997, Nucleic Acids Research, 25:1203-1210).

Several variant P1 promoters were first created containing the tetO2 operator in each of three locations: upstream of the −33 (distal; P1TD), within the spacer region between the −33 and −7 (core; P1TC), or downstream of the transcription start site (proximal; P1TP) (FIG. 1B and Table 2). In each location, tetO2 sequences were engineered as sequence insertions, partial substitutions, or complete substitutions in the orientation that best preserves the consensus promoter sequence (FIG. 1A). An additional promoter containing the tetO2 operator in both the distal and proximal regions (P1T$_{DP}$) was created.

TABLE 2

Genetic parts

| SEQID NO. | Part Name | Description | DNA Sequence |
|---|---|---|---|
| 1 | NanoLuc | Luciferase reporter (from Promega) | ATGGTCTTCACACTCGAAGATTTCGTTGG GGACTGGCGACAGACAGCCGGCTACAACC TGGACCAAGTCCTTGAACAGGGAGGTGTG TCCAGTTTGTTTCAGAATCTCGGGGTGTC CGTAACTCCGATCCAAAGGATTGTCCTGA GCGGTGAAAATGGGCTGAAGATCGACATC CATGTCATCATCCCGTATGAAGGTCTGAG CGGCGACCAAATGGGCCAGATCGAAAAAA TTTTTAAGGTGGTGTACCCTGTGGATGAT CATCACTTTAAGGTGATCCTGCACTATGG CACACTGGTAATCGACGGGGTTACGCCGA ACATGATCGACTATTTCGGACGGCCGTAT GAAGGCATCGCCGTGTTCGACGGCAAAAA GATCACTGTAACAGGGACCCTGTGGAACG GCAACAAAATTATCGACGAGCGCCTGATC AACCCCGACGGCTCCCTGCTGTTCCGAGT AACCATCAACGGAGTGACCGGCTGGCGGC TGTGCGAACGCATTCTGGCGTAA |
| 2 | lpxF | Gene BT1854; reporter for growth on polymyxin B | ATGATAGAATTTCTTTCGGATATAGACAC CCAACTGCTTTTGTTCTTCAATGGAATAC ATTCGCCTTTCTGGGATTACTTCATGAGT GCATTCACAGGTAAAGTTATATGGGTCCC GATGTATGCCAGTATCTTATATATACTGC TCAAGAATTTTCATTGGAAAGTGGCTTTG TGCTATGTGGTAGCGATCGCCCTCACTAT CACGTTTGCCGATCAGATGTGCAATAGTT TTCTTCGTCCGCTGGTAGGTCGCCTGCGT CCCTCCAATCCGGAAAATCCGATAGCGGA TTTGGTCTATATTGTGAATGGAAGACGAG GAGGAGGATTCGGTTTCCCTTCCTGTCAT GCTGCCAATTCTTTCGGACTTGCCATATT TCTGATTTGCCTGTTCCGTAAACGCTGGT TAAGCATATTTATCGTACTTTGGGCATTT ACCAACTCTTATACACGCCTGTACCTGGG ATTGCATTATCCCGGTGATTTAGTAGCAG GAGCCATTATCGGTGGATTCGGAGGTTGG CTGTTCTACTTTATCGCCCACAAGTTAAC GGCACGACTTCAGTCAGACACTCCTGTTC CTGGAAAGGGTGCCGGAATGAAACAAACA GAAGTTATGATCTATACCGGATTGCTGAC TTTAGCAGGCATTATCATCTATTCCATCG TGCAAAGTTAG |

TABLE 2-continued

Genetic parts

| SEQID NO. | Part Name | Description | DNA Sequence |
|---|---|---|---|
| 3 | BT1754 | HTCS gene BT1754; reporter for growth in fructose | ATGATGAGATGGATGAAGACGATGAGATA TCTGAAGTGGATGCTGGTGCTGTTTGGTT TAATCGGGATGACGGCTTGCCGGCAGGAT ACACCCCATTTTCGTATTGGGGTGGCTCA ATGCAGCGATGATTCATGGCGACATAAGA TGAATGATGAGATTCTTCGGGAAGCAATG TTTTATAATGGCGTTTCGGTGGAAATCCG TTCGGCAGGAGATGATAACAGTAAGCAGG CGGAAGATGTCCATTATTTTATGGACGAA GGAGTCGATCTGCTGATTATTTCCGCTAA CGAAGCTGCTCCTATGACTCCGATTGTAG AAGAAGCTTATCAGAAAGGCATCCCCGTT ATTCTTGTAGACCGGAAGATTCTTTCGGA TAAATATACTGCCTATATCGGAGCCGATA ATTATGAAATCGGTCGTTCGGTAGGAAAC TATATTGCCTCCAGTCTGAAAGGGAAGGG AAATATAGTAGAACTGACAGGATTGAGCG GTTCGACTCCTGCAATGGAACGGCATCAG GGATTTATGGCTGCCATCAGTAAATTCCC GGATATAAAGCTGATTGATAAAGCGGATG CTGCGTGGGAACGTGGTCCGGCAGAGATA GAAATGGATAGTATGCTTCGGAGGCATCC TAAGATTGATGCTGTGTATGCCCATAATG ACCGTATCGCTCCGGGTGCCTATCAGGCA GCAAAGATGGCAGGGCGGGAGAAGGAAAT GATTTTTGTCGGCATAGATGCCTTGCCGG GTAAGGGAAACGGACTGGAACTGGTTTTG GACAGTGTGCTGGATGCCACCTTTATCTA TCCGACCAATGGCGATAAGGTACTGCAAC TGGCTATGGACATTCTGGAGAAGAAACCC TATCCCAAAGAAACGGTGATGAATACCGC TGTTGTGGACCGTACCAACGCACACGTCA TGCAGTTGCAGACTACACACATCTCCGAA CTCGATAAAAAGATTGAAACGCTCAACGG ACGTATCGGTGGATACCTCTCTCAGGTAG CTACACAACAGGTCGTTTTATACGGCAGT CTGATTATCCTTTTATTGGTAGCCGGCTT ATTATTGGTCGTTTATAAATCACTCCGCT CTAAGAATCGCTTGAATAAAGAGCTTTTT AAGCAGAAGCAGCAATTGGAAGAGCAGCG TGACAAACTGGAAGAACAGCGTGACCAAT TGATACAGCTCTCTCATCAACTGGAAGAA GCTACCCATGCCAAGCTGGTCTTTTTCAC CAATATTTCTCACGACTTCCGTACTCCGT TGACATTGGTTGCCGACCCGGTAGAACAT TTATTGGCGGACAAGACATTGAGTGGAGA TCAGCACCGGATGCTCATGCTGATTCAGC GAAATGTGAATATCCTTTTGCGCCTGGTC AATCAGATTTTGGATTTCCGTAAATATGA AAACGGCAAGATGGAATATACTCCGGTTA CGGTGGATGTCCTTTCTTCTTTCGAAGGA TGGAATGAGTCTTTTCAGGCGGCAGCCCG TAAGAAGCATATCCATTTTTCTTTTGATA GTATGCCGGATACGGATTATCATACACTG GCAGACATGGAGAAGCTGGAACGTATTTA TTTCAATCTCCTGTCCAATGCCTTTAAGT TTACACCGGAAAACGGGAAAATAGCCATC CGTCTGTCTTCCCTTAGTAAAGAGGACAA GCGATGGATACGTTTCACGGTGGCAAATA CCGGTTCCATGATTTCTGCCGAACATATC CGCAATGTATTCGACCGTTTCTATAAGAT TGATATGCACCATACCGGTTCGGGAATCG GACTGGCATTGGTAAAAGCCTTCGTAGAA ATGCACGGTGGTATGATCTCCGTAGAGAG CGATGAGAAACAGGGCACGGTCTTTACCG TTGAACTGCCTGTACAGTCTTGTGAGGCT GTTGCTGCCGAACCGGATACCACCCTTGT TTCTGCGGATTCCCGTACAACAGATGTTC TATTGGCAGAAGAGGAAGAACTGGAAAAA GGATATGACTCTTCCAAACCGTCCGTACT GATTATTGATGATAATGAGGATATCCGTT CGTATGTCCATACGCTGTTGCATACAGAC TATACGGTGATTGAAGCGGCAGACGGCTC CGAAGGAATCCGTAAGGCTATGAAGTATG TTCCGGACCTGATCATTTCTGATGTGATG |

TABLE 2-continued

Genetic parts

| SEQID NO. | Part Name | Description | DNA Sequence |
|---|---|---|---|
| | | | ATGCCGGGCATTGATGGCATTGAATGTTG<br>CCGCCGGCTGAAAAGTGAGTTACAGACCT<br>GTCATATTCCGGTTATTCTGCTGACAGCG<br>TGTTCACTGGACGAACAGCGTATTCAGGG<br>ATATGACGGTGGTGCGGATTCTTATATTT<br>CAAAGCCGTTCAGTTCACAGCTGTTGCTG<br>GCACGTGTCCGCAATCTGATCGATTCTCA<br>CCGTCGTCTGAAACAGTTCTTTGGTGACG<br>GGCAGACATTGGCAAAAGAAGATGTCTGC<br>GATATGGACAAGGATTTTGTAGAAAGATT<br>CAAGTCATTGATTGAAGAGAAAATGGGAG<br>ACTCCGGTTTGAATGTGGAGGACTTGGGC<br>AAAGACATGGGACTAAGCCGTGTGCAGCT<br>TTATCGCAAGATTAAATCATTGACTAACT<br>ACTCTCCGAATGAATTGCTCCGTATCGCC<br>CGTTTGAAGAAGGCAGCTTCTTTGCTTGC<br>TTCTTCGGACATGACCGTAGCGGAGATTG<br>GTTATGAAGTCGGTTTCAGTTCACCTTCT<br>TATTTCGCCAAGTGCTATAAAGAGCAGTT<br>TGGAGAGAGCCCGACAGATTTCCTGAAAA<br>GGAAAGGATGA |
| 4 | ss | Periplasmic localization signal from BT4676 | ATGAAGAAAATTTTATCTTTGCTTGTGAT<br>GGCTATTGTAGCTATACAGTTCTCATTTG<br>CCGGC |
| 5 | ss-bte1 | Periplasmic localized T6SS effector from *B. fragilis* NCTC 9343 | ATGAAGAAAATTTTATCTTTGCTTGTGAT<br>GGCTATTGTAGCTATACAGTTCTCATTTG<br>CCGGCGGTAAGGAAATAGAAATAAAGAAA<br>TTGCCAGAGTTCGAGGCTATGGTGAATGC<br>CGGTAATACGACCTATACGGGATTGGTAG<br>AAGGCATCGGGTATGTGTATTGGACAACA<br>GAAACCCTATATTTTATCCGCACTAATCC<br>AGAACAATTATGGGCGATTCCAAAATATC<br>AGCAAATACCTTTCCCCTATTTTCAAAGG<br>AAAGATGCAATCATTGAGACCAAAACATT<br>ACATACACTCCATGTCTTGTCAAAAGATG<br>AACTGTTGAAATTGGATTACGATGCCTAT<br>TATGCATTTTATGGTATCGTGGAGGAGAT<br>GCTAAAATTTATTCATCGGGCGGATGCTA<br>TTAAAAGTTATTGTGAAATACCTCTTCCC<br>ATAATAAAATCCAAAGGAGCACTAAAGGG<br>AAATGACGCAAGAAATGGGATACTATCAT<br>TAGGTAGTCAAATAAATGACCAAATCGGA<br>GCTCCCCTTGATGCAGCGAATATGCTAAT<br>GGATAATAAACATATAGGCAAAATTGGAG<br>ATGGATTGTCGCTTATTTCTATTATAGAT<br>GAGGTAGGTAATGGTGAATATTGGTCAGC<br>TGCCGGAGACATTTTACTGTTTGCAGCCG<br>GAAAAACAAAATTAAGTCCCTATATGACT<br>GTCATAAGTTTAGGCACATGGATGTATGA<br>GACGGACTTGATGCAATGGAGATTAGCAT<br>GTATAAATTATAGCGATTACAAAAAAACA<br>CTAATAAAATATCGAGAATTACAAAAAAA<br>ATTTGAAAGTGGAGACAAATCTGTAGAGG<br>AAAAGATGAATGAATGTCACAAAATACTG<br>AATTCACATTATATAGAGATGCAAAAAAA<br>TTTAGGTAATCTAGGAGTTAAATTCTAA |
| 6 | ss-bfe1 | Periplasmic localized T6SS effector from *B. fragilis* 638R | ATGAAGAAAATTTTATCTTTGCTTGTGAT<br>GGCTATTGTAGCTATACAGTTCTCATTTG<br>CCGGCGCTTATAGAAATGAATATAAAACG<br>CAAAGTGAATTTAATGTCATCTTGGAACG<br>GGGGGATGACTATGAAGGATTTGTAGTTG<br>GCTTGGGATATACTTGGATGAGTAGCAAG<br>GTAATTCTACCGGTAAATCAAAACGGATG<br>GAGTCCAATATCTCGGAATGTTTCGGTGG<br>ACGAGAGTTTTCATACGATAGTCTCAGAA<br>AGGAAATACGATACCTCCCAATATGCCTA<br>TGAAAAAAGTCTGATGCAAGATCCAACAA<br>AAGTTTCCGAAAAGGTCCGTGACTTAATA<br>GTTAAAAACAAAGGTAATAATATCACTGA<br>GATAAATTTAGGCCAAGAAAAGCAATATT<br>TGCCCACGGATAATAGTCAGATAAGTATT |

TABLE 2-continued

Genetic parts

| SEQID NO. | Part Name | Description | DNA Sequence |
|---|---|---|---|
| | | | GTAATTACTGACACTGGCAGTCGGTACGA AATTGTGATTAGTGCCACGGATAACTCAA ATGGAAAGACTTATGAGGCAAAGTATGAG AGTTTGACGGACTTGGTGTCAGCGGTACG CGATTCTGGTAGCCTGCCTGCTGTAAATA AGGAAGGACCCAATCTGGAAGGACTGGCA GGGTTAGGATTCGGAATTGCTGAAACAGC CGGAAATTGGGCTGAGAAGATTATGGATA ATCGAGGTGCGTACTTACCTAAGCAGATG CGTTTCTCGCCCAAAACGCTTCCGCCGAT TATAAGATTGCCTTTAGGGAACTATCAAG TCCCCGCTAAAGGTATGAGTAGAGTGCGT GGAGTAGGTAAAGCTTTGGGATGGGCAGG AATGGTGCTTACTGGCTATCAAGTTGTGC GTGATGTGCAAAATGGTCGATTTGCCGTG GCAGGTACAAGAATTGCCGTAGCAGGTTT AGCTTATGGCGTTACTTTTATTCCCTATG TCGGTTGGGTCTTAGCTATCGGTATCGGA GTGGCTGATTATACTTGGGGTGACGAGTT CTATGACTGGATAGACAATAGAGCTTCTG AATTGGAAATGTGGTGGGACGGTGTAAGA TTAGCATTATGA |
| 7 | tetR (E. coli) | Transcriptional Repressor | ATGTCTAGATTAGATAAAAGTAAAGTGAT TAACAGCGCATTAGAGCTGCTTAATGAGG TCGGAATCGAAGGTTTAACAACCCGTAAA CTCGCCCAGAAGCTAGGTGTAGAGCAGCC TACATTGTATTGGCATGTAAAAAATAAGC GGGCTTTGCTCGACGCCTTAGCCATTGAG ATGTTAGATAGGCACCATACTCACTTTTG CCCTTTAGAAGGGGAAAGCTGGCAAGATT TTTTACGTAATAACGCTAAAAGTTTTAGA TGTGCTTTACTAAGTCATCGCGATGGAGC AAAAGTACATTTAGGTACACGGCCTACAG AAAAACAGTATGAAACTCTCGAAAATCAA TTAGCCTTTTTATGCCAACAAGGTTTTTC ACTAGAGAATGCATTATATGCACTCAGCG CTGTGGGGCATTTTACTTTAGGTTGCGTA TTGGAAGATCAAGAGCATCAAGTCGCTAA AGAAGAAAGGGAAACACCTACTACTGATA GTATGCCGCCATTATTACGACAAGCTATC GAATTATTTGATCACCAAGGTGCAGAGCC AGCCTTCTTATTCGGCCTTGAATTGATCA TATGCGGATTAGAAAAACAACTTAAATGT GAAAGTGGGTCTTAA |
| 8 | P1 | Constitutive promoter (last nucleotide is +1 TSS) | TTTTGCACCCGCTTTCCAAGAGAAGAAAG CCTTGTTAAATTGACTTAGTGTAAAAGCG CAGTACTGCTTGACCATAAGAACAAAAAA ACTTCCGATAAAGTTTGGAAGATAAAGCT AAAAGTTCTTATCTTTGCAGTC |
| 9 | GH023 | RBS | GAAATAAAGACATATAAAA |
| 10 | P1-GH023 | Constitutive promoter + RBS GH023 | TTTTGCACCCGCTTTCCAAGAGAAGAAAG CCTTGTTAAATTGACTTAGTGTAAAAGCG CAGTACTGCTTGACCATAAGAACAAAAAA ACTTCCGATAAAGTTTGGAAGATAAAGCT AAAAGTTCTTATCTTTGCAGTCCGAAATA AGACATATAAAAGAAAAGACACCATG |
| 11 | tetO2 | operator binding site for TetR | TCCCTATCAGTGATAGAGA |
| 12 | P1TD | Synthetic aTC-inducible promoter (distal tetO2) + RBS GH023 | TTTGCACCCGCTTTCCAAGAGAAGAAAGC CTTGTTAAATTGACTTAGTGTAAAGCGC AGTACTGCTTGACCATAAGAACAAAAAAA TCTCTATCACTGATAGGGATAAAGTTTGG AAGATAAAGCTAAAAGTTCTTATCTTTGC AGTCCGAAATAAAGACATATAAAGAAAA GACACCATG |

TABLE 2-continued

Genetic parts

| SEQID NO. | Part Name | Description | DNA Sequence |
|---|---|---|---|
| 13 | P1TC | Synthetic aTC-inducible promoter (core tetO2) + RBS GH023 | TTTTGCACCCGCTTTCCAAGAGAAGAAAG CCTTGTTAAATTGACTTAGTGTAAAAGCG CAGTACTGCTTGACCATAAGAACAAAAAA ACTTCCGATAAAGTTTGGTCCCTATCAGT GATAGAGATTATCTTTGCAGTCCGAAATA AAGACATATAAAAGAAAAGACACCATG |
| 14 | P1TP | Synthetic aTC-inducible promoter (proximal tetO2) + RBS GH023 | TTTTGCACCCGCTTTCCAAGAGAAGAAAG CCTTGTTAAATTGACTTAGTGTAAAAGCG CAGTACTGCTTGACCATAAGAACAAAAAA ACTTCCGATAAAGTTTGGAAGATAAAGCT AAAAGTTCTTATCTTTGCAGTCTCCCTAT CAGTGATAGAGACGAAATAAAGACATATA AAAGAAAAGACACCATG |
| 15 | P1TDP | Synthetic aTC-inducible promoter (distal and promixal tetO2) + RBS GH023 | TTTTGCACCCGCTTTCCAAGAGAAGAAAG CCTTGTTAAATTGACTTAGTGTAAAAGCG CAGTACTGCTTGACCATAAGAACAAAAAA ATCTCTATCACTGATAGGGATAAAGTTTG GAAGATAAAGCTAAAAGTTCTTATCTTTG CAGTCTCCCTATCAGTGATAGAGACGAAA TAAAGACATATAAAAGAAAAGACACCATG |
| 16 | P2 | Constitutive promoter (last nucleotide is + 1 TSS) | AAGAAAAGGCGTTTTGTTTTTCTTCTTTA CCTTCTTTCCCTTTCGCTAAGAGAGTCTG AGAAACGATAGAAAAAGAAAAGCGAAAAA ACTTCCGAAAACATTTGGTAGTTAAAATA AAACCTCTTACCTTTGCACCC |
| 17 | PBT1311 | Constitutive promoter of BT1311 (upstream 300 base pairs) | TGATCTGGAAGAAGCAATGAAAGCTGCTG TTAAGTCTCCGAATCAGGTATTGTTCCTG ACAGGTGTATTCCCATCCGGTAAACGCGG ATACTTTGCAGTTGATCTGACTCAGGAAT AAATTATAAATTAAGGTAAGAAGATTGTA GGATAAGCTAATGAAATAGAAAAAGGATG CCGTCACACAACTTGTCGGCATTCTTTTT TGTTTTATTAGTTGAAAATATAGTGAAAA AGTTGCCTAAATATGTATGTTAACAAATT ATTTGTCGTAACTTTGCACTCCAAATCTG TTTTTAAAGA |
| 18 | A21 | RBS | CGCATTTTAAAATAAAATAAATTATTTAT GATATTAAACGAAT |
| 19 | B1 | RBS | CGCATTTTAAAATAAAATAAATAATTTAC TTAATTAAACGAAT |
| 20 | rpiL* | RBS | CGCATTTTAAAATAAAATAAATTATTTAT TTAATTAAACGAAT |
| 21 | B41 | RBS | CGCATTTTAAAATAAAATAAATCATATAG TTAATTAAACGAAT |
| 22 | B40 | RBS | CGCATTTTAAAATAAAATAAATCATGTAG TTAATTAAACGAAT |
| 23 | C56 | RBS | CGCATTTTAAAATAAAATAAATTATTCGT TTAGTTAAACGAAT |
| 24 | P1TDP-A21 | Synthetic aTC-inducible promoter (distal and promixal tetO2) + RBS A21 | TTTGCACCCGCTTTCCAAGAGAAGAAAGC CTTGTTAAATTGACTTAGTGTAAAAGCGC AGTACTGCTTGACCATAAGAACAAAAAA TCTCTATCACTGATAGGGATAAAGTTTGG AAGATAAAGCTAAAAGTTCTTATCTTTGC AGTCTCCCTATCAGTGATAGAGACGCATT TTAAAATAAAATAAATTATTTATGATATT AAACGAATCCATG |
| 25 | P1TDP-B1 | Synthetic aTC-inducible promoter (distal and | TTTGCACCCGCTTTCCAAGAGAAGAAAGC CTTGTTAAATTGACTTAGTGTAAAAGCGC AGTACTGCTTGACCATAAGAACAAAAAA TCTCTATCACTGATAGGGATAAAGTTTGG AAGATAAAGCTAAAAGTTCTTATCTTTGC |

TABLE 2-continued

Genetic parts

| SEQID NO. | Part Name | Description | DNA Sequence |
|---|---|---|---|
| | | promixal tetO2) + RBS B1 | AGTCTCCCTATCAGTGATAGAGACGCATT TTAAAATAAATAAATAATTTACTTAATT AAACGAATCCATG |
| 26 | P1TDP-rpiL* | Synthetic aTC-inducible promoter (distal and promixal tetO2) + RBS rpiL* | TTTGCACCCGCTTTCCAAGAGAAGAAAGC CTTGTTAAATTGACTTAGTGTAAAAGCGC AGTACTGCTTGACCATAAGAACAAAAAA TCTCTATCACTGATAGGGATAAAGTTTGG AAGATAAAGCTAAAAGTTCTTATCTTTGC AGTCTCCCTATCAGTGATAGAGACGCATT TTAAAATAAATAAATTATTTATTTAATT AAACGAATCCATG |
| 27 | P1TDP-B41 | Synthetic aTC-inducible promoter (distal and promixal tetO2) + RBS B41 | TTTTGCACCCGCTTTCCAAGAGAAGAAAG CCTTGTTAAATTGACTTAGTGTAAAAGCG CAGTACTGCTTGACCATAAGAACAAAAAA ATCTCTATCACTGATAGGGATAAAGTTTG GAAGATAAAGCTAAAAGTTCTTATCTTTG CAGTCTCCCTATCAGTGATAGAGACGCAT TTTAAAATAAATAAATCATATAGTTAAT TAAACGAATCCATG |
| 28 | P1TDP-B40 | Synthetic aTC-inducible promoter (distal and promixal tetO2) + RBS B40 | TTTGCACCCGCTTTCCAAGAGAAGAAAGC CTTGTTAAATTGACTTAGTGTAAAAGCGC AGTACTGCTTGACCATAAGAACAAAAAA TCTCTATCACTGATAGGGATAAAGTTTGG AAGATAAAGCTAAAAGTTCTTATCTTTGC AGTCTCCCTATCAGTGATAGAGACGCATT TTAAAATAAATAAATCATGTAGTTAATT AAACGAATCCATG |
| 29 | P1TDP-C56 | Synthetic aTC-inducible promoter (distal and promixal tetO2) + RBS C56 | TTTGCACCCGCTTTCCAAGAGAAGAAAGC CTTGTTAAATTGACTTAGTGTAAAAGCGC AGTACTGCTTGACCATAAGAACAAAAAA TCTCTATCACTGATAGGGATAAAGTTTGG AAGATAAAGCTAAAAGTTCTTATCTTTGC AGTCTCCCTATCAGTGATAGAGACGCATT TTAAAATAAATAAATTATTCGTTTAGTT AAACGAATCCATG |
| 30 | P2-A21 | Constitutive promoter + RBS A21 | AAGAAAAGGCGTTTTGTTTTTCTTCTTTA CCTTCTTTCCCTTTCGCTAAGAGAGTCTG AGAAACGATAGAAAAAGAAAAGCGAAAAA ACTTCCGAAAACATTTGGTAGTTAAAATA AAACCTCTTACCTTTGCACCCGCGCATTT TAAAATAAATAAATTATTTATGATATTA AACGAAT |
| 31 | P2-A21-tetR; P1TDP | Single unit tetracycline inducible cassette | TTAAGACCCACTTTCACATTTAAGTTGTT TTTCTAATCCGCATATGATCAATTCAAGG CCCGAATAAGAAGGCTGGCTCTGCACCTTG GTGATCAAATAATTCGATAGCTTGTCGTA ATAATGGCGGCATACTATCAGTAGTAGGT GTTTCCCTTTCTTCTTTAGCGACTTGATG CTCTTGATCTTCCAATACGCAACCTAAAG TAAAATGCCCCACAGCGCTGAGTGCATAT AATGCATTCTCTAGTGAAAAACCTTGTTG GCATAAAAAGGCTAATTGATTTTCGAGAG TTTCATACTGTTTTTCTGTAGGCCGTGTA CCTAAATGTACTTTTGCTCCATCGCGATG ACTTAGTAAAGCACATCTAAAACTTTTAG CGTTATTACGTAAAAAATCTTGCCAGCTT TCCCCTTCTAAAGGGCAAAGTGAGTATG GTGCCTATCTAACATCTCAATGGCTAAGG CGTCGAGCAAAGCCCGCTTATTTTTTACA TGCCAATACAATGTAGGCTGCTCTACACC TAGCTTCTGGGCGAGTTTACGGGTTGTTA AACCTTCGATTCCGACCTCATTAAGCAGC TCTAATGCGCTGTTAATCACTTTACTTTT ATCTAATCTAGACATATTCGTTAATATC ATAAATAATTTATTTTATTTTAAAATGCG CGGGTGCAAAGGTAAGAGGTTTTATTTTA ACTACCAAATGTTTTCGGAAGTTTTTTCG CTTTTCTTTTTCTATCGTTTCTCGAGACTC TCTTAGCGAAAGGGAAAGAAGGTAAAGAA |

TABLE 2-continued

Genetic parts

| SEQ ID NO. | Part Name | Description | DNA Sequence |
|---|---|---|---|
| | | | GAAAAACAAAACGCCTTTTCTTTTTTGCA CCCGCTTTCCAAGAGAAGAAAGCCTTGTT AAATTGACTTAGTGTAAAAGCGCAGTACT GCTTGACCATAAGAACAAAAAAATCTCTA TCACTGATAGGGATAAAGTTTGGAAGATA AAGCTAAAAGTTCTTATCTTTGCAGTCTC CCTATCAGTGATAGAGACGAAATAAAGAC ATATAAAAGAAAAGACACCATG |

TABLE 3

Bacterial strains, plasmids, and primers used in this study

| Strains, Plasmid, Primer Name | | Notes and/or sequence (5'-3') | Insert | Source Reference |
|---|---|---|---|---|
| | *Bacteria species and strains* | | | |
| | *E. coli* EC100D pir-116 | F-mcrA Δ(mrr-hsdRMS-mcrBC) φ80dlacZΔM15 ΔlacX74 recA1 endA1 araD139 Δ(ara, leu)7697 galU galK λ-rpsL (StrR) nupG pir-116(DHFR) | | PMID_8125283 |
| | *E. coli* S17-1 lambda pir | recA pro hsdR RP4-2-Tc::Mu-Km::Tn7 λ-pir | | PMID_6340113 |
| | *B. thetaiotaomicron* VPI-5482 | | | ATCC 29148 |
| | *B. thetaiotaomicron* VPI-5482 tdk | In-frame deletion of BT2275 | | PMID_18611383 |
| 1xtetR | *B. thetaiotaomicron* VPI-5482 tdk; BT1311p-tetR-1 | tetR expressed from the BT1311 promoter placed between chromosomal position 4861701 and 4861702 | | This study |
| | *B. thetaiotaomicron* VPI-5482 tdk; BT1311p-tetR-1; P1TDP-BT1754 | BT1754 promoter replaced with P1T_DP-GH023 | | This study |
| | *B. thetaiotaomicron* VPI-5482 DBT1754 | In-frame deletion of tdk; BT1754 in Dtdk background | | This study |
| 2xtetR | *B. thetaiotaomicron* VPI-5482 tdk BT1311p-tetR-2 | 1xtetR; tetR expressed from the BT1311 promoter placed between chromosomal position 2660693 and 2660694 | | This study |
| 3xtetR | *B. thetaiotaomicron* VPI-5482 tdk BT1311p-tetR-3 | 2xtetR; tetR expressed from the BT1311 promoter placed between chromosomal position 6193956 and 6193957 | | This study |
| | *B. thetaiotaomicron* VPI-5482 tdk; BT1311p-tetR-3; DBT0455 | 3xtetR; In-frame deletion of BT0455 | | This study |
| | *Bacteroides fragilis* NCTC 9343; ATCC 25285 | | | ATCC 25285 |
| | *Bacteroides fragilis* 638R | | | PMID_20829291 |

TABLE 3-continued

Bacterial strains, plasmids, and primers used in this study

| Strains, Plasmid, Primer Name | Notes and/or sequence (5'-3') | Insert | Source Reference |
|---|---|---|---|
| *Bacteroides ovatus* ATCC 8483 | | | ATCC 8483 |
| *Bacteroides ovatus* ATCC 8483 tdk | in-frame deletion of BACOVA_03071 | | PMID_24463512 |
| *Bacteroides ovatus* ATCC 8483 tdk; DBACOVA_04598 | in-frame deletion of BACOVA_04598 (lpxF homologue) | | This study |
| *Bacteroides ovatus* ATCC 8483 tdk; TetR-P1T_DP-BACOVA_04598 | BACOVA_04598 promoter replaced with TetR-P1T_DP-B1 | | This study |
| *Bacteroides uniformis* ATCC 8492 | | | ATCC 8492 |
| *Bacteroides vulgatus* ATCC 8482 | | | ATCC 8482 |
| *Bacteroides thetaiotaomicron* 1 | Isolate from human donor 1 | | This study PMID_21436049 |
| *Bacteroides ovatus* 2 | Isolate from human donor 2 | | This study PMID_21436049 |
| *Bacteroides xylanisolvens* 3 | Isolate from human donor 3 | | This study PMID_21436049 |
| *Bacteroides intestinalis* 1 | Isolate from human donor 1 | | This study PMID_21436049 |
| *Bacteroides intestinalis* 3 | Isolate from human donor 3 | | This study PMID_21436049 |
| *Bacteroides intestinalis* 4 | Isolate from human donor 4 | | This study PMID_21436049 |
| *Bacteroides uniformis* 1 | Isolate from human donor 1 | | This study PMID_21436049 |
| *Bacteroides uniformis* 3 | Isolate from human donor 3 | | This study PMID_21436049 |
| *Bacteroides uniformis* 4 | Isolate from human donor 4 | | This study PMID_21436049 |
| *Bacteroides fragilis* 4 | Isolate from human donor 4 | | This study PMID_21436049 |
| *Bacteroides dorei* 2 | Isolate from human donor 2 | | This study PMID_21436049 |
| *Bacteroides dorei* 3 | Isolate from human donor 3 | | This study PMID_21436049 |
| *Bacteroides vulgatus* 1 | Isolate from human donor 1 | | This study PMID_21436049 |
| *Bacteroides cellulosilyticus* 3 | Isolate from human donor 3 | | This study PMID_21436049 |
| Bacteroides eggerthii 4 | Isolate from human donor 4 | | This study PMID_21436049 |
| Allelic exchange plasmids | | | |
| pExchange_tdk | Suicide vector carrying cloned tdk (BT2275) from *B. thetaiotaomicron* for counter-selection, AmpR, ErmR | | PMID_18611383 |

TABLE 3-continued

Bacterial strains, plasmids, and primers used in this study

| Strains, Plasmid, Primer Name | Notes and/or sequence (5'-3') | Insert | Source Reference |
|---|---|---|---|
| pExchange_tdk_BT1311p-tetR-1 | Integration construct carrying 1kb flanks to integrate between BT3743 and BT3744, AmpR, ErmR | | This study |
| pExchange_tdk_BT1311p-tetR-2 | Integration construct carrying 1kb flanks to integrate between BT3743 and BT3744, AmpR, ErmR | | This study |
| pExchange_tdk_BT1311p-tetR-3 | Integration construct carrying 1kb flanks to integrate between BT4719 and BT4720 AmpR, ErmR | | This study |
| pExchange_tdk_BT1754_DEL | Deletion construct carrying 1kb flanks of BT1754, AmpR, ErmR | | This study |
| pExchange_tdk_P1T_DP_GH023-BT1374 | Replacement construct replacing 200 base pairs of BT1754 promoter with P1T_D-GH023P, AmpR, ErmR | | This study |
| pExchange_tdk_BACOVA_04598_DEL | Deletion construct carrying 1kb flanks of BACOVA_04598 AmpR, ErmR | | This study |
| pExchange_tdk_P1T_DP-B1-BACOVA_04598 | Replacement construct replacing 62 base pairs of BACOVA_04598 promoter with TetR-P1T_DP-B1, AmpR, ErmR | | This study | pNBU2 vectors for single-site integration at attB sites

| | | | |
|---|---|---|---|
| pNBU2_erm | Integrates cloned fragments to NBU2 att sites, ErmR, AmpR | | PMID_18611383 |
| pNBU2_erm_P1-GH023 | P1-GH023_RBS | | This study |
| pNBU2_erm_P1T_D-GH023 | P1-GH023_RB5, distal tetO2 | | This study |
| pNBU2_erm_P1T_C-GH023 | P1-GH023_RBS, core tetO2 | | This study |
| pNBU2_erm_P1T_P-GH023 | P1-GH023_RBS, proximal tetO2 | | This study |
| pNBU2_erm_P1T_DP-GH023 | P1-GH023_RBS, distal and proximal tetO2 | | This study |
| pNBU2_erm_P2-GH023 | P2-GH023 RBS | | This study |
| pNBU2_erm_P1-GH023-NanoLuc | P1-GH023 RBS | NanoLuc | This study |
| pNBU2_erm_P1T_D-GH023-NanoLuc | P1-GH023_RBS, distal tetO2 | NanoLuc | This study |
| pNBU2_erm_P1T_C-GH023-NanoLuc | P1-GH023_RBS, core tetO2 | NanoLuc | This study |
| pNBU2_erm_P1T_P-GH023-NanoLuc | P1-GH023_RBS, proximal tetO2 | NanoLuc | This study |

TABLE 3-continued

Bacterial strains, plasmids, and primers used in this study

| Strains, Plasmid, Primer Name | Notes and/or sequence (5'-3') | Insert | Source Reference |
|---|---|---|---|
| pNBU2_erm_P1T_DP-GH023-NanoLuc | P1-GH023_RBS, distal and proximal tetO2 | NanoLuc | This study |
| pNBU2_erm_P2-GH023-NanoLuc | P2-GH023 RBS | NanoLuc | This study |
| pNBU2_erm_P1-GH023-lpxF | P1-GH023 RBS | lpxF | This study |
| pNBU2_erm_P1T_D-GH023-lpxF | P1-GH023_RBS, distal tetO2 | lpxF | This study |
| pNBU2_erm_P1T_C-GH023-lpxF | P1-GH023_RBS, core tetO2 | lpxF | This study |
| pNBU2_erm_P1T_P-GH023-lpxF | P1-GH023_RBS, proximal tetO2 | lpxF | This study |
| pNBU2_erm_P1T_DP-GH023-lpxF | P1-GH023_RBS, distal and proximal tetO2 | lpxF | This study |
| pNBU2_erm_P2-GH023-lpxF | P2-GH023 RBS | lpxF | This study |
| pNBU2_erm_P1T_DP-GH023-ss-bte1 | P1-GH023_RBS, distal and proximal tetO2 | Periplasmic localized bte1 under control of P1T_DP | This study |
| pNBU2_erm_P1T_DP-GH023-ss-bfe1 | P1-GH023_RBS, distal and proximal tetO2 | Periplasmic localized bfe1 under control of P1T_DP | This study |
| pNBU2_erm_P1T_DP-A21 | P1 -A21_RBS, distal and proximal tetO2 | | This study |
| pNBU2_erm_P1T_DP-B1 | P1 -B 1_RBS, distal and proximal tetO2 | | This study |
| pNBU2_erm_P1T_DP-rpiL* | P1 -rpiL*_RBS, distal and proximal tetO2 | | This study |
| pNBU2_erm_P1T_DP-B41 | P1 -B 41_RBS, distal and proximal tetO2 | | This study |
| pNBU2_erm_P1T_DP-B40 | P1 -B 40_RBS, distal and proximal tetO2 | | This study |
| pNBU2_erm_P1T_DP-C56 | P1 -056_RBS, distal and proximal tetO2 | | This study |
| pNBU2_erm_P1T_DP-A21-NanoLuc | P1 -A21_RBS, distal and proximal tetO2 | NanoLuc | This study |
| pNBU2_erm_P1T_DP-B1-NanoLuc | P1-B1_RBS, distal and proximal tetO2 | NanoLuc | This study |
| pNBU2_erm_P1T_DP-rpiL*-NanoLuc | P1 -rpiL *_RBS, distal and proximal tetO2 | NanoLuc | This study |
| pNBU2_erm_P1T_DP-B41-NanoLuc | P1-B41_RBS, distal and proximal tetO2 | NanoLuc | This study |
| pNBU2_erm_P1T_DP-B40-NanoLuc | P1-B40_RBS, distal and proximal tetO2 | NanoLuc | This study |
| pNBU2_erm_P1T_DP-C56-NanoLuc | P1-056_RBS, distal and proximal tetO2 | NanoLuc | This study |
| pNBU2_erm-TetR-P1T_DP-GH023 | single-unit tetracycline-inducible promoter; tetR driven by P2-A21 | | This study |

TABLE 3-continued

Bacterial strains, plasmids, and primers used in this study

| Strains, Plasmid, Primer Name | Notes and/or sequence (5'-3') | Insert | Source Reference |
|---|---|---|---|
| | promoter; P1T_DP-GH023 regulatable promoter | | |
| pNBU2_erm-TetR-P1T_DP-GH023-NanoLuc | single-unit tetracycline-inducible promoter; tetR driven by P2-A21 promoter; P1T_DP-GH023 regulatable promoter | NanoLuc | This study |

Primers

| | | | |
|---|---|---|---|
| 8F | AGAGTTTGATCCTGGCTCAG (SEQ ID NO: 32) | 16S rDNA sequencing | |
| 1492Rm | CGGCTACCTTGTTACGACTT (SEQ ID NO: 33) | 16S rDNA sequencing | |
| del_1754_A | cttgatatcgaattcctgca CTTTTTCGTCTGCGGACATT AATG (SEQ ID NO: 34) | Deletion of BT1754 | |
| del_1754_B | atcaatgaaaTTCATAGTTC TTTCTGTAATCCAATTAAG (SEQ ID NO: 35) | Deletion of BT1754 | |
| del_1754_C | gaactatgaaaTTTCATTGAT ATCGTAAAGAGGGATATATG (SEQ ID NO: 36) | Deletion of BT1754 | |
| del_1754_D | ttcccctccaccgcggtggc TGGCATTGTTGCTGTGCTAT C (SEQ ID NO: 37) | Deletion of BT1754 | |
| del_0455_A | cttgatatcgaattcctgca AGAATTCACCACCCTGAAC (SEQ ID NO: 38) | Deletion of BT0455 | |
| del_0455_B | gacttdcatAAATGGGGGTA TTAGTTAATTTAAC (SEQ ID NO: 39) | Deletion of BT0455 | |
| del_0455_C | accccatttATGAAAAGTC TTCGAATCTTTTTGG (SEQ ID NO: 40) | Deletion of BT0455 | |
| del_0455_D | ttcccctccaccgcggtggc GCCAGCATATTCGGGTAAAA ATTATTTTC (SEQ ID NO: 41) | Deletion of BT0455 | |
| del_B0_04598_A | cttgatatcgaattcctgca TTCATGGACCCGAAAATAG (SEQ ID NO: 42) | Deletion of BACOVA_04598 | |
| del_B0_04598_B | atgttgtgttCAGGCTTTAT TGATCTATTTTAATG (SEQ ID NO: 43) | Deletion of BACOVA_04598 | |
| del_B0_04598_C | ataaagcctgAACACAACAT ATTTCGAACTAAAAAG (SEQ ID NO: 44) | Deletion of BACOVA_04598 | |
| del_B0_04598_D | ttcccctccaccgcggtggc AACAACTTGCCCGAAGAATG (SEQ ID NO: 45) | Deletion of BACOVA_04598 | |
| P1T_DP-GH023-NanoLuc-A | acatataaaagaaaagacac ATGGTCTTCACACTCGAAG (SEQ ID NO: 46) | Placement of NanoLuc into PIT DP-GH023 vector | |

TABLE 3-continued

Bacterial strains, plasmids, and primers used in this study

| Strains, Plasmid, Primer Name | Notes and/or sequence (5'-3') | Insert | Source Reference |
|---|---|---|---|
| P1T_DP-GH023-NanoLuc-B | actggaagataggcaattag TTACGCCAGAATGCGTTC (SEQ ID NO: 47) | Placement of NanoLuc into P1T DP-GH023 vector | |
| P1T_DP-GH023-BT1854-A | acatataaaagaaaagacac ATGATAGAATTTCTTTCGGA TATAG (SEQ ID NO: 48) | Placement of BT1854 into P1T DP-GH023 vector | |
| P1T_DP-GH023-BT1854-B | actggaagataggcaattag CTAACTTTGCACGATGGAAT AG (SEQ ID NO: 49) | Placement of BT1854 into P1T_DP-GH023 vector | |
| P1T_DP-GH023-BT0455-A | acatataaaagaaaagacac ATGAAAAGAAATCATTATTT ATTTACC (SEQ ID NO: 50) | Placement of BT0455 into P1T_DP-GH023 vector | |
| P1T_DP-GH023-BT0455-B | actggaagataggcaattag TCATCGAATCAAATCTTTCA G (SEQ ID NO: 51) | Placement of BT0455 into P1T_DP-GH023 vector | |
| Primers for promoter-NanoLuc fusions | | | |
| NanoLuc A | ATGGTCTTCACACTCGAAGA TTTCGTTG (SEQ ID NO: 52) | For fusing to promoter regions - 5' primer | |
| NanoLuc B | cttgatatcgaattcctgca TTACGCCAGAATGCGTTCGC (SEQ ID NO: 53) | For fusing to promoter regions - Gibson cloning into pNBU2-Erm digested with SalI - 3' primer | |
| BT0408_US | ttccctccaccgcggtggc ATTCAAAATCAGGTTCCATC CTTCCTTAG (SEQ ID NO: 54) | | |
| BT0408_DS | tcttcgagtgtgaagaccat AATTTATACTGTTTAAAATG ATTATGATACAACAAATATA ACATTTTTC (SEQ ID NO: 55) | | |

TABLE 3-continued

Bacterial strains, plasmids, and primers used in this study

| Strains, Plasmid, Primer Name | Notes and/or sequence (5'-3') | Insert | Source Reference |
|---|---|---|---|
| BT1973_US | ttccctccaccgcggtggc ATGATTCATAGTACAGTCTA CTTGACGTTTACC (SEQ ID NO: 56) | | |
| BT1973_DS | tcttcgagtgtgaagaccat GATATCATATTTTAAAAGGT TATTCTGATAAAATGTAAAC TGCTC (SEQ ID NO: 57) | | |
| BT0646_US | ttccctccaccgcggtggc GCCAAGTATGGTTTCTTGGG ATATCG (SEQ ID NO: 58) | | |
| BT0646_DS | tcttcgagtgtgaagaccat AATTCTAAAGTTTTAATTAA TACTATAGTTAAATCATCTG TTTAATTAACAATGC (SEQ ID NO: 59) | | |
| BT1311_US | ttccctccaccgcggtggc TGATCTGGAAGAAGCAATGA AAGCTG (SEQ ID NO: 60) | | |
| BT1311_DS | tcttcgagtgtgaagaccat TCTTTAAAAACAGATTTGGA GTGCAAAGTTACG (SEQ ID NO: 61) | | |
| BT3895_US | ttccctccaccgcggtggc AAGATTTGTATCATTCGGAT TTGGTAGACG (SEQ ID NO: 62) | | |
| BT3895_DS | tcttcgagtgtgaagaccat AATTAGTTCAGAATTGAGAG TGGAAAATTGATAGTTC (SEQ ID NO: 63) | | |
| BT2500_US | ttccctccaccgcggtggc AGTTATTGGCTGCAAAGGTA GATAATATTCTGTTC (SEQ ID NO: 64) | | |
| BT2500_DS | tcttcgagtgtgaagaccat AATTGTATATTTTTATTAG TTCAACTTTCTTTTTTGTT CTTCTG (SEQ ID NO: 65) | | |
| BT0539_US | ttccctccaccgcggtggc TAATTCACAAAGGAAATTTC TGAAATATATTGTTTATCAG C (SEQ ID NO: 66) | | |
| BT0539_DS | tcttcgagtgtgaagaccat AAGCTAAAAATAAAATGATT GTTTTATCCTGAATGTATC (SEQ ID NO: 67) | | |
| BT0455_US | ttccctccaccgcggtggc CAGCAGAATACATAGAACAG GAAGAAAACG (SEQ ID NO: 68) | | |
| BT0455_DS | tcttcgagtgtgaagaccat AAATGGGGGTATTAGTTAAT TTAACGAAGGC (SEQ ID NO: 69) | | |

TABLE 3-continued

Bacterial strains, plasmids, and primers used in this study

| Strains, Plasmid, Primer Name | Notes and/or sequence (5'-3') | Insert | Source Reference |
|---|---|---|---|
| BT4213_US | ttccctccaccgcggtggc CATAGATTAAAACTGTTTTC AGGATTAGATTAAGGG (SEQ ID NO: 70) | | |
| BT4213_DS | tcttcgagtgtgaagaccat CTCTTTTTAATTTATTTTAT CGGGTTCCTATTGATAAC (SEQ ID NO: 71) | | |
| BT4719_US | ttccctccaccgcggtggc CACGGTCGCCGGTATAGC (SEQ ID NO: 72) | | |
| BT4719_DS | tcttcgagtgtgaagaccat ATACTATAAAAATGTTTTTT AATGAGTACTATTTACTTGC TTTG (SEQ ID NO: 73) | | |
| BT0633_US | ttccctccaccgcggtggc GGTGGTGACGTAAGCCGTAA AC (SEQ ID NO: 74) | | |
| BT0633_DS | tcttcgagtgtgaagaccat CAGGAAGCCCGAAAAAGACA GAAC (SEQ ID NO: 75) | | |
| BT1854_US | ttccctccaccgcggtggc ATTGCCGCTACGCTGCTTTC (SEQ ID NO: 76) | | |
| BT1854_DS | tcttcgagtgtgaagaccat AAAATAAATCGTATTATTAA AAGGTGGATTTGTCTGATC (SEQ ID NO: 77) | | |
| BT0295_US | ttccctccaccgcggtggc CTCATAGTGGTGGTAAGGGT GG (SEQ ID NO: 78) | | |
| BT0295_DS | tcttcgagtgtgaagaccat GACATTTTATTTGTCCTATG TTGTATTGGGTG (SEQ ID NO: 79) | | |
| BT3486_US | ttccctccaccgcggtggc TCTTTGGCTTTAGAGCGTCA GATC (SEQ ID NO: 80) | | |
| BT3486_DS | tcttcgagtgtgaagaccat AATTATTCCGATTTAATTAA CACCATTCTCATTGC (SEQ ID NO: 81) | | |
| BT0481_US | ttccctccaccgcggtggc GCTGAAACATACAGAGGAAT ATGCCC (SEQ ID NO: 82) | | |
| BT0481_DS | tcttcgagtgtgaagaccat AACTGTGATGAATTAGATAT CTATTCTTTTATACTTTGTT G (SEQ ID NO: 83) | | |
| BT2778_US | ttccctccaccgcggtggc GTTTCCACTCTTTCTTCTAT AAATTTGTATTTACCC (SEQ ID NO: 84) | | |
| BT2778_DS | tcttcgagtgtgaagaccat GTGCGTGTATTATTTTAATA TGATGAATAGAAACCG (SEQ ID NO: 85) | | |

TABLE 3-continued

Bacterial strains, plasmids, and primers used in this study

| Strains, Plasmid, Primer Name | Notes and/or sequence (5'-3') | Insert | Source Reference |
|---|---|---|---|
| BT4618_US | ttcccctccaccgcggtggc ATCCACCATTGAGCACCAAC GAC (SEQ ID NO: 86) | | |
| BT4618_DS | tcttcgagtgtgaagaccat TTTTTCTTCGTATTAAAATT TATGCCGCAAAAGTATAGG (SEQ ID NO: 87) | | |
| BT4227_US | ttcccctccaccgcggtggc GTTTCTTGCGAAACAAACAA AAGAACAAAAC (SEQ ID NO: 88) | | |
| BT4227_DS | tcttcgagtgtgaagaccat TTTAGTTTTGATTTTAATGT GTGATGCTATAATTCTTTTT TTTAG (SEQ ID NO: 89) | | |
| BT1709_US | ttcccctccaccgcggtggc TTGCATAAAATCTTTATTGG AAAAGTTAATAAAACAATAG C (SEQ ID NO: 90) | | |
| BT1709_DS | tcttcgagtgtgaagaccat TTTGATAAATTTACATATGG ATACAATATCCAAAGAAACA G (SEQ ID NO: 91) | | |
| BT3347_US | ttcccctccaccgcggtggc TCATCATCACACCTACATAA AGTTATGCAAAC (SEQ ID NO: 92) | | |
| BT3347_DS | tcttcgagtgtgaagaccat AAATATAAATAATAAAATGG TTAAAGTGCATCCGAAC (SEQ ID NO: 93) | | |
| BT4179_US | ttcccctccaccgcggtggc CTTTCTAAATGGTAGTTTAA ATCTTCTCTGTAGTGC (SEQ ID NO: 94) | | |
| BT4179_DS | tcttcgagtgtgaagaccat TGCCTTTATATAATCCGGTA AACGATTGTTAG (SEQ ID NO: 95) | | |

To first investigate the positional effects of the tetO2 operators on basal gene expression in the absence of the TetR repressor, the native P1 and P2 promoters, and each synthetic promoter, were fused to a standard *Bacteroides* RBS (GH023) (Wegmann, U. et al., 2013, Appl. Environ. Microbiol., 79:1980-1989), followed by the NanoLuc luciferase gene as a reporter (Hall, M. P. et al., 2012, ACS Chem. Biol., 7:1848-1857). Integration of these constructs into the *B. thetaiotaomicron* genome in single copy at a standard location revealed luminescence approximately four orders of magnitude higher than a control strain that lacks a promoter upstream of NanoLuc (FIG. 1C). Placement of tetO2 in the distal, core, and/or proximal regions of P1 decreased promoter activity 1.8- to 6.8-fold (FIG. 1C). Together, these results suggest that tetO2 insertion affects promoter activity, but reporter activity remains 4,200-fold to 16,000-fold above background, depending on operator placement.

To test the function of native *Bacteroides* genes expressed under the control of these engineered promoters, the Nano-Luc reporter was replaced with BT1854 (lpxF). LpxF is a phospholipid phosphatase that determines resistance to cationic antimicrobial peptides (including polymixin B; PMB) in *Bacteroides*, and deletion of lpxF in *B. thetaiotaomicron* reduces PMB resistance by four orders of magnitude (Cullen, T. W. et al., 2015, Science, 347:170-175). Expression of lpxF under the control of the native P1, native P2, P1T$_D$, P1T$_P$, and P1T$_{DP}$ promoters in a *B. thetaiotaomicron* lpxF mutant increases PMB resistance to wildtype levels, while the P1TC-lpxF fusion does not (FIG. 1D).

Example 3: A Synthetic Inducer Modulates Gene Expression Over a Broad Dynamic Range Next, a constitutive tetR cassette was integrated in a neutral (not required for fitness) location in the *B. thetaiotaomicron* genome to create Bt::tetR (FIG. 2A). Introduction of the panel of promoter-NanoLuc fusions (FIG. 1B) into Bt::tetR revealed that while TetR has no effect on the activity of the native P1 promoter, all of the tetO2-containing promoters exhibit a significant decrease in activity in the presence of TetR (FIG. 2B, red bars). Of these promoters, P1T$_{DP}$ shows the greatest repression by TetR, with reporter expression 6,800-fold above background in the absence of TetR (FIG. 1C) and decreasing to within 4-fold of background levels when TetR is present (FIG. 2B, red bars).

Figures 8A, 8B, 8C, 8D:
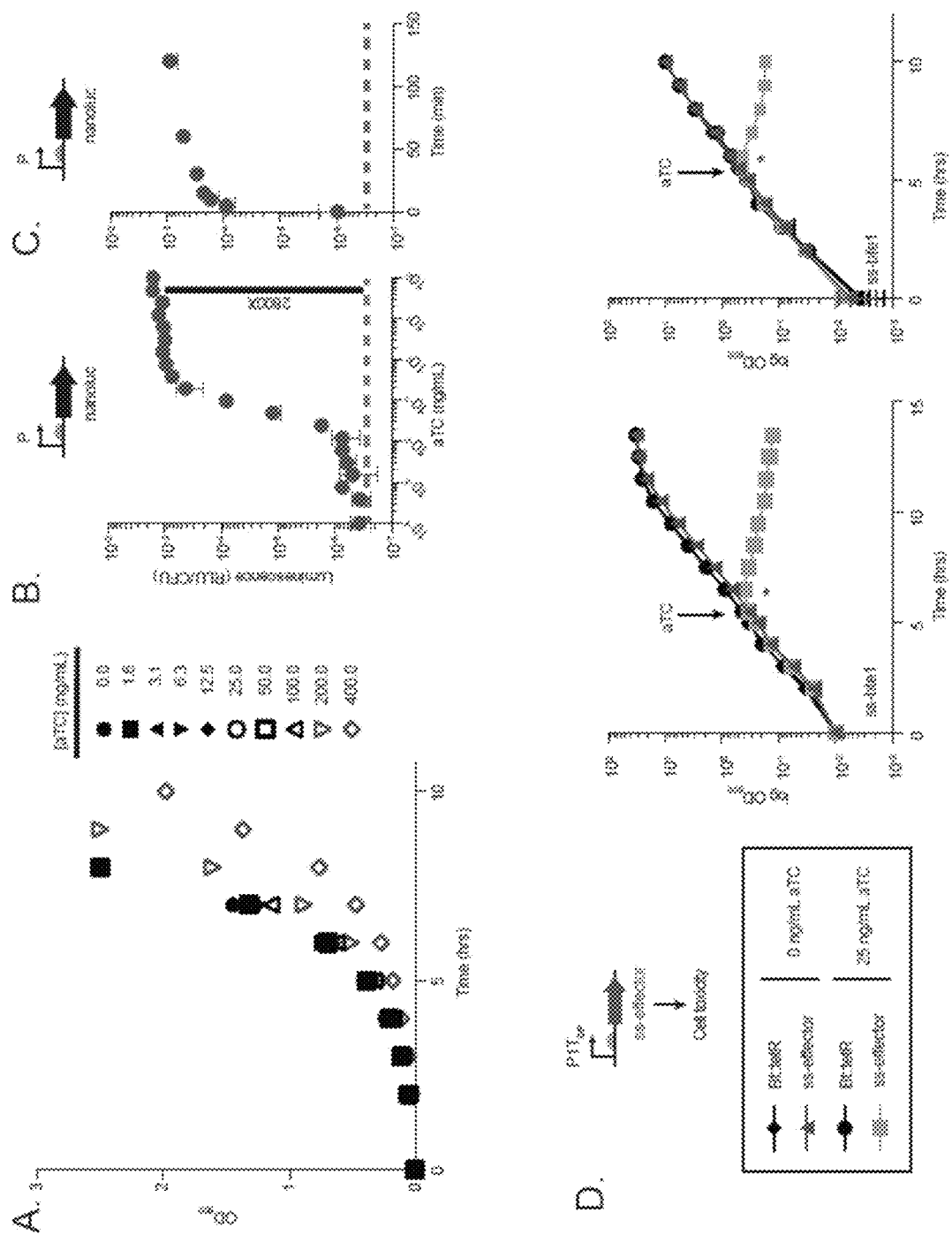
FIG. 8D, depicts results from example experiments showing the regulation of *Bacteroides* gene expression via a synthetic inducer, and attaining regulatory control of endogenous loci and highly toxic gene products.
(FIG. 8A) *Bacteroides* grow at wildtype rates in aTC concentrations typically used to control gene expression from tetracycline-regulated promoters.
(FIG. 8B, and FIG. 8C) $P1T_{DP}$ expression can be tuned over a 100-fold range in aTC concentration and induces in response to aTC within one round of cell division.

Addition of aTC (100 ng/mL) to strains constitutively expressing TetR derepresses each of the tetO2-containing promoters, producing reporter levels equivalent to those measured in strains lacking tetR (FIG. 2B, green bars versus FIG. 1C). This indicates that aTC readily reaches the *Bacteroides* cytoplasm. While the promoters with a single tetO2 exhibit at most an 80-fold induction of reporter activity in the presence of aTC, promoter P1T$_{DP}$ increases luminescence over 2,000-fold in response to the inducer (FIG. 2B). Consistent with this result, introduction of the panel of promoter-lpxF fusions into an lpxF mutant constitutively expressing TetR (Bt::tetR lpxF) revealed that TetR represses expression of the P1T$_{DP}$-lpxF fusion to levels that reduce PMB MIC by over 10,000-fold, functionally equivalent to the absence of lpxF entirely (<0.064 µg/mL; FIG. 2C). In strains carrying the other promoters, TetR expression also reduces PMB MIC, although some resistance remains (FIG. 2C). Except for P1TC, addition of 100 ng/mL aTC restores PMB MIC to wildtype levels in each case (FIG. 2C). Additional examination of the sensitivity and temporal dynamics of the system showed that P1T$_{DP}$ expression can be tuned over a 100-fold range in aTC concentration and induces in response to aTC within one round of cell division (FIG. 8B and S1C). Together, these results highlight the utility of the P1T$_{DP}$ platform for stringent regulation of both exogenous and endogenous genes in *B. thetaiotaomicron*.

Example 4: Acquiring Regulatory Control of Endogenous Loci

Figures 3A, 3B, 3C:
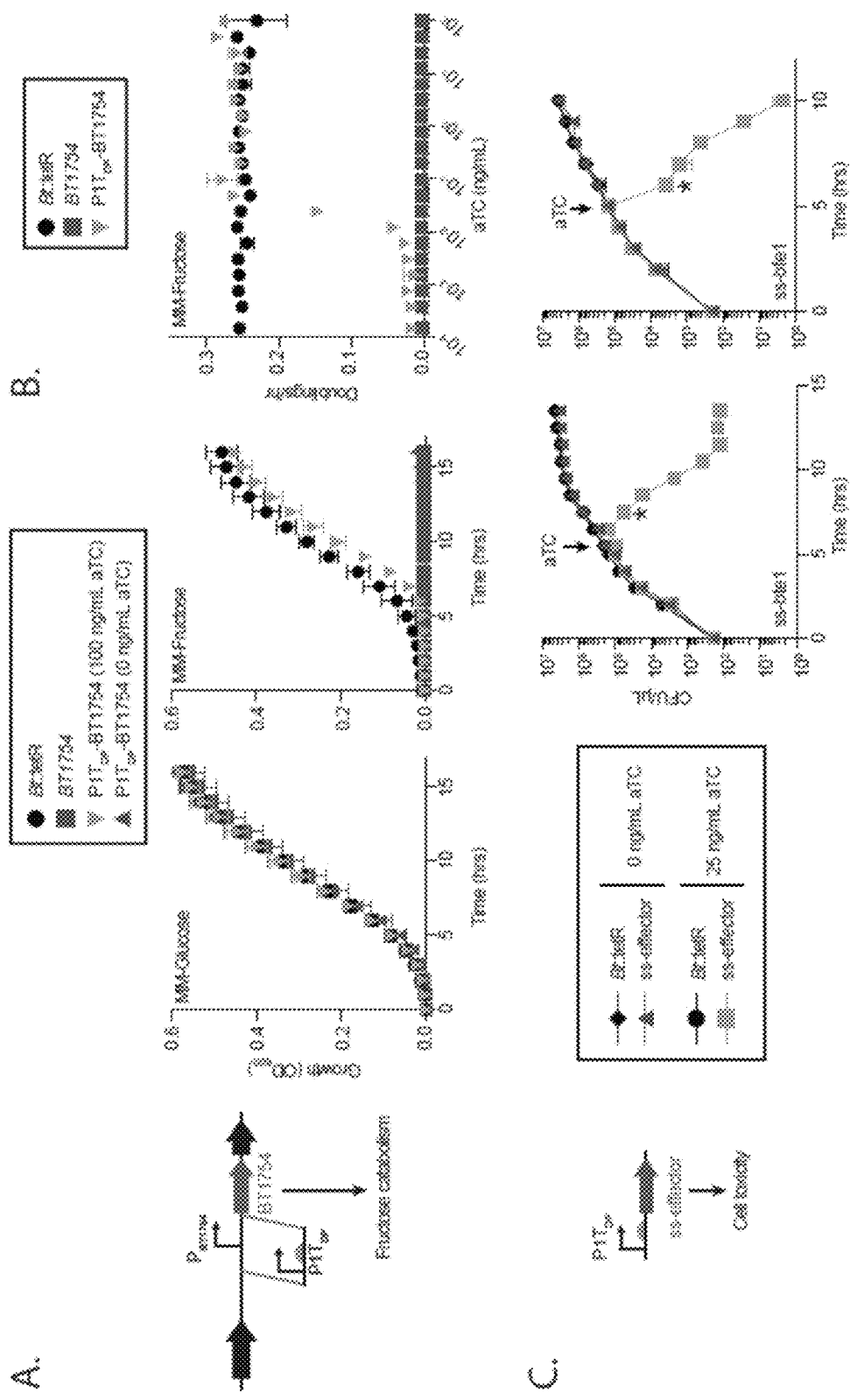
FIG. 3A through FIG. 3C, depicts results from example experiments showing the attainment of regulatory control of endogenous loci and highly toxic gene products.

Regulatory control of a gene or locus can be acquired by deleting gene(s) of interest and then returning the gene(s) under the control of an engineered promoter as shown for lpxF above. However, direct replacement of the native promoter provides an important one-step alternative, especially if there are complications in creating a gene deletion (e.g. essential genes; deletions that impact the regulation of neighboring genes) and/or complementation (e.g. long, multiple, or undefined operons; repeating or low-complexity sequences recalcitrant to amplification). The hybrid two-component sensor BT1754 regulates a multi-gene polysaccharide utilization locus required for growth on fructose. The 200 base pairs upstream of BT1754 was replaced with the 200 base pair P1T$_{DP}$ promoter (FIG. 3A) in Bt::tetR (designated Bt::tetR P1T$_{DP}^{GH023}$-BT1754). Growth of Bt::tetR P1T$_{DP}^{GH023}$-BT1754 is entirely dependent on the addition of aTC in fructose but not glucose (FIG. 3A). Additionally, cell doubling rates in fructose can be readily tuned by varying aTC concentrations (FIG. 3B). Together, these studies establish that the P1T$_{DP}$ system can be used to assume control of endogenous loci in *Bacteroides*.

Example 5: Gene Expression is Tightly Repressed in the Absence of Inducer

Tight control in the OFF state is a critical goal for engineered gene regulatory platforms. In theory, genes that encode highly deleterious proteins should be nonlethal under repressing conditions if tight control is achieved. The Type VI secretion system (T6SS)-delivered antibacterial effectors Bte1 and Bfe1, encoded by *B. fragilis* strains NCTC 9343 and 638R, respectively, allow these strains to efficiently kill *B. thetaiotaomicron* upon transient contact (Chatzidaki-Livanis, M. et al., 2016, Proceedings of the National Academy of Sciences, 113:3627-3632; Wexler, A. G. et al., 2016, Proceedings of the National Academy of Sciences, 113: 3639-3644). Translational fusions of each effector with an N-terminal periplasmic localization signal sequence ("ss") were constructed and placed these fusions under the control of P1T$_{DP}$ in Bt::tetR (FIG. 3C). Expression of ss-Bte1 or ss-Bfe1 in *B. thetaiotaomicron* is highly toxic, because addition of aTC results in immediate decreases in viability and culture density (FIG. 3C and FIG. 8D). Toxicity resulting from aTC-induced effector expression is likely a consequence of their underlying mechanism of action and not from overproduction of a heterologous protein, as expression of either effector without a periplasmic signal sequence does not affect *B. thetaiotaomicron* viability (data not shown). In the OFF state (without aTC), growth of strains carrying P1T$_{DP}$-ss-bte1, P1T$_{DP}$-ss-bfe1, and the Bt::tetR parental strain is equivalent (FIG. 3C and FIG. 8D). Together, these studies establish that the P1T$_{DP}$ platform provides strict repression of gene expression in the OFF state.

Figures 4A, 4B, 4C:
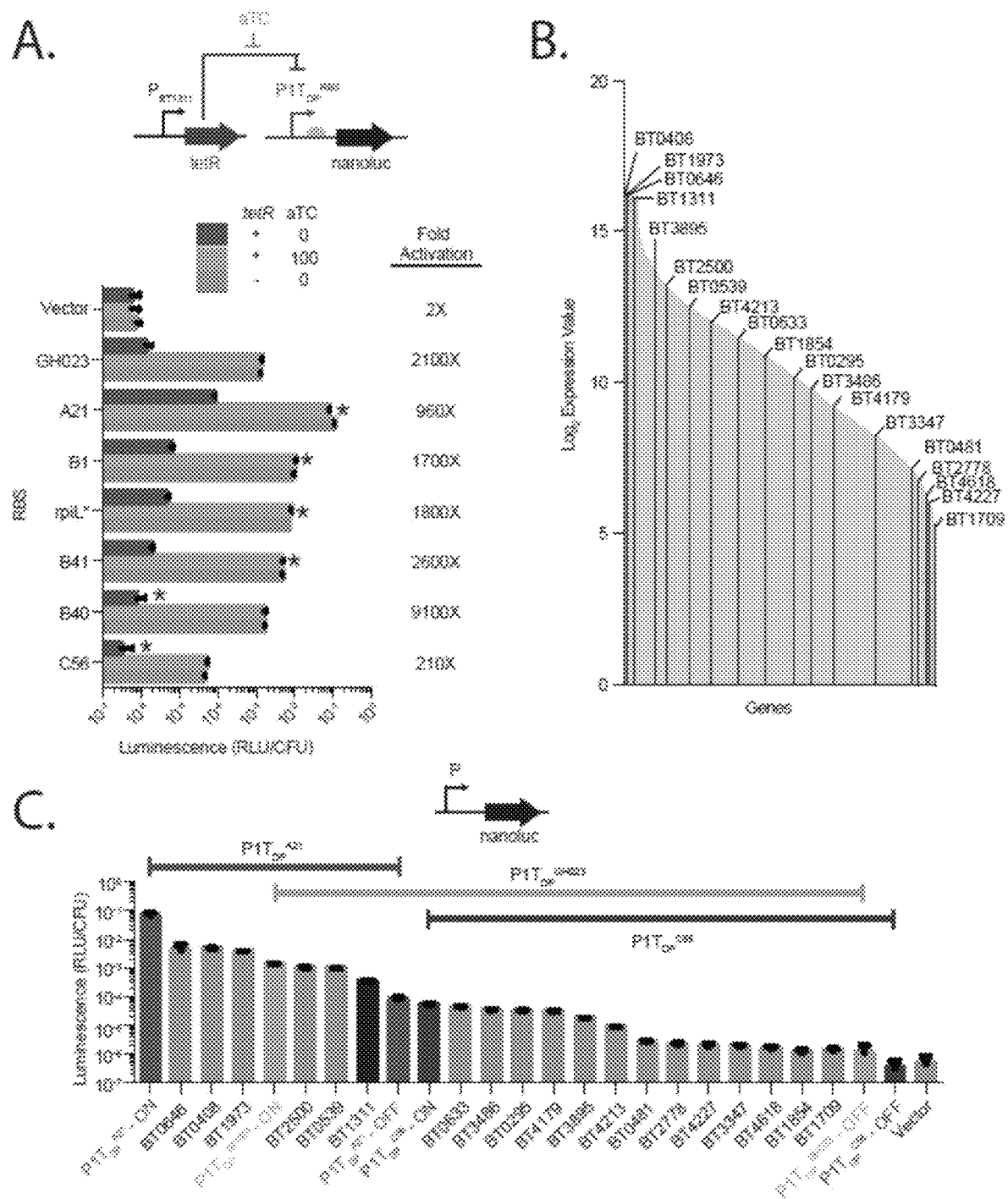
FIG. 4A through FIG. 4C, depicts results from example experiments showing that a panel of ribosome binding sites extends the dynamic range of $P1T_{DP}$ to over 105-fold, spanning the complete range of native gene expression in *B. thetaiotaomicron*.

Example 6: An RBS Panel Extends the Dynamic Range of the *Bacteroides* Inducible Promoter to Capture Promoter Activity Levels Observed Across the *B. thetaiotaomicron* Transcriptome Ribosome binding site (RBS) variation provides an additional layer of gene expression control to engineered promoters. The original RBS (GH023) in P1T$_{DP}$ was replaced with 6 alternate RBSs (designated P1T$_{DP}^{RBS}$) (Mimee, M. et al., 2015, Cell Systems, 1:62-71). The 6 RBSs modulate P1T$_{DP}$ promoter expression by three orders of magnitude, in a pattern generally similar to that previously reported for a native *B. thetaiotaomicron* promoter (FIG. 4A, FIG. 9A, FIG. 9B) (Mimee, M. et al., 2015, Cell Systems, 1:62-71). RBS variation impacts expression in the induced and uninduced state proportionally (FIG. 9A and FIG. 9B) and can extend the dynamic response to aTC: for example, P1T$_{DP}^{B40}$ provides negligible expression in the uninduced state (1.4-fold over background) which increases 9,100-fold when aTC is provided, a 3.3-fold increase over P1T$_{DP}^{GH023}$. Luminescence production from P1T$_{DP}$-NanoLuc carrying each RBS is comparable between wildtype *B. thetaiotaomicron* and Bt::tetR in the ON state, suggesting that varying the RBS does not disrupt promoter activation and that TetR repression is fully relieved in all RBS variants with the addition of aTC (FIG. 4A; green bar vs grey bar). Together, this panel of RBS variants coupled to the P1T$_{DP}$ promoter further extends the range of expression to 320,000-fold (e.g., between P1T$_{DP}^{C56}$ in the OFF state and P1T$_{DP}^{A21}$ in the ON state).

Figures 9A, 9B, 9C:
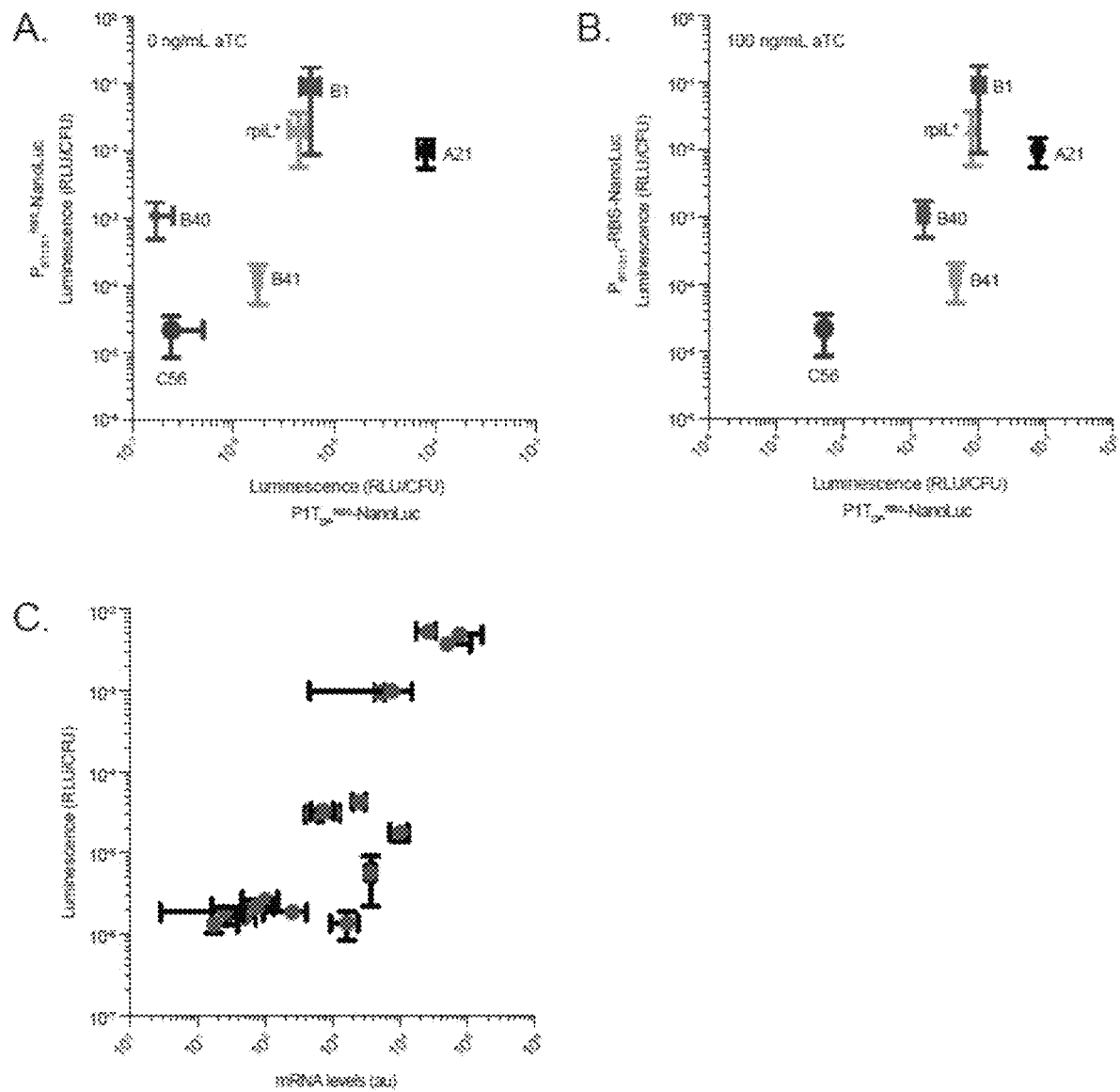
FIG. 9A through FIG. 9C, depicts results from example experiments showing that a panel of ribosome binding sites extends the dynamic range of $P1T_{DP}$ to over 105-fold, spanning the complete range of native gene expression in *B. thetaiotaomicron*.

To compare this range of expression to native promoter strengths in *B. thetaiotaomicron*, the NanoLuc reporter was fused to the promoters of 18 *B. thetaiotaomicron* ORFs whose mRNA levels span the complete expression range of this organism in rich medium based on transcriptome studies (Sonnenburg, J. L. et al., 2005, Science, 307:1955-1959) (FIG. 4B). Luminescence production from these 18 promoter fusions is largely proportional to the previously reported mRNA levels of the corresponding ORFs (FIG. 9C). The P1T$_{DP}$ platform fully spans the range of native promoter activities, producing luminescence levels ranging from 14-fold higher than the strongest native promoter tested (P1T$_{DP}$A21, ON state) to 6.7-fold lower than the weakest native promoter tested (P1T$_{DP}$$^{C56}$, OFF state) (FIG. 4C). Notably, the expression range of P1T$_{DP}$$^{GH023}$ alone captures ~86% of the 18 native *B. thetaiotaomicron* promoters tested, which corresponds to ~97% of the transcriptome (FIG. 4C). These results establish that the P1T$_{DP}$ platform provides the capacity to express *Bacteroides* proteins to their native levels.

Figure 5:
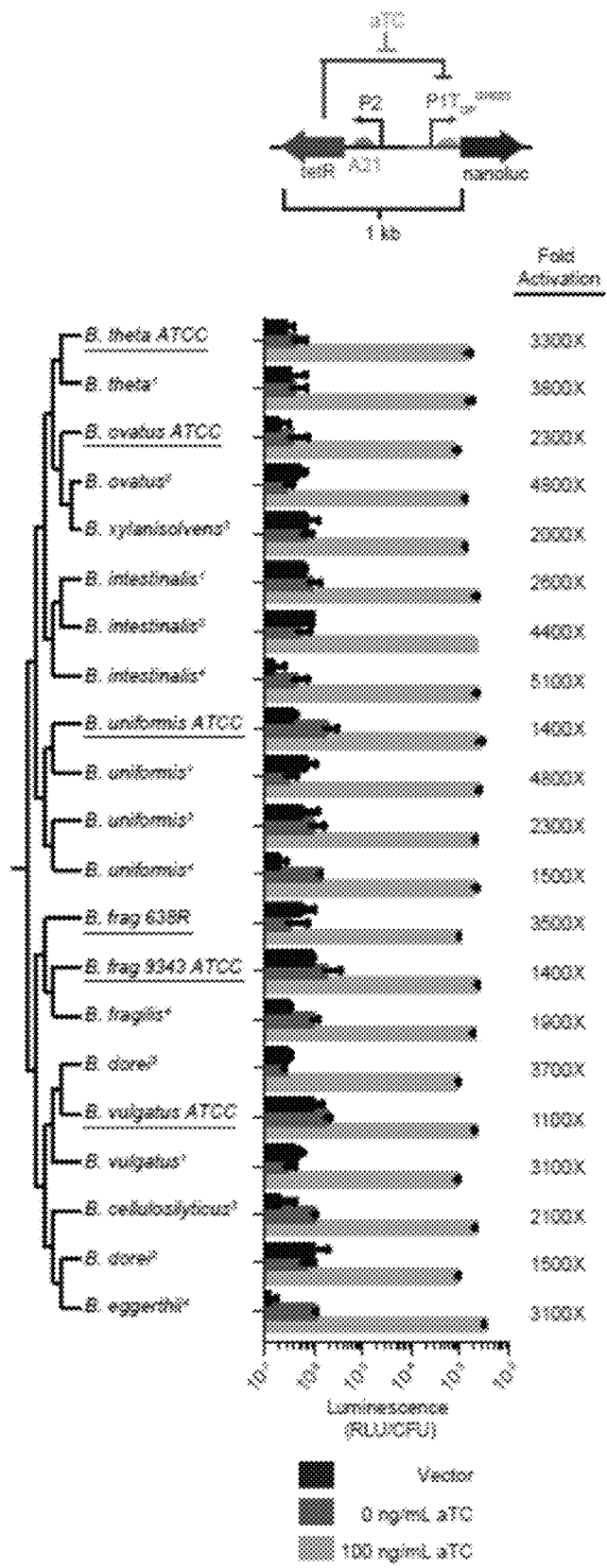
FIG. 5 depicts results from example experiments showing that a self-contained, inducible expression cassette functions across diverse *Bacteroides* species. Strains are sorted by 16S rDNA phylogeny, with type strains (Table 3) underlined and novel isolates (isolated directly from human donors) noted with superscript indicating donor number. Activity of TetR-$P1T_{DP}^{GH023}$-NanoLuc in each strain is shown. Error bars represent the standard deviation of three biological replicates on separate days.

Example 7: Evaluation and Performance of the P1T$_{DP}$ Platform in Different *Bacteroides* Species To facilitate gene expression control across species, a self-contained, ~1 kb inducible expression cassette was built (designated TetR-P1T$_{DP}$) in which tetR is expressed from the P2$^{A21}$ promoter and oriented in the opposite direction from P$_1$T$_{DP}$$^{GH023}$, thereby providing the ability to artificially regulate gene expression in unmodified strains of multiple species in a single step (FIG. 5). TetR-P1T$_{DP}$$^{GH023}$-NanoLuc reporter fusions displayed robust induction over 3 orders of magnitude in an aTC-dependent manner in 6 different *Bacteroides* type strains representing 5 species (FIG. 5, underlined). The cassette was also introduced into 15 additional *Bacteroides* isolates (representing 11 different species) cultured directly from 4 unrelated human donors. These isolates encode diverse 16S rRNA gene sequences and exhibit doubling times ranging from 38 to 137 minutes in rich medium, consistent with a broad range of phylogeny and physiology (FIG. 5). The TetR-P1T$_{DP}$$^{GH023}$-NanoLuc cassette could be readily introduced into all isolates, and each exhibited robust induction of luminescence in an aTC-dependent manner (FIG. 5).

Figure 10A:
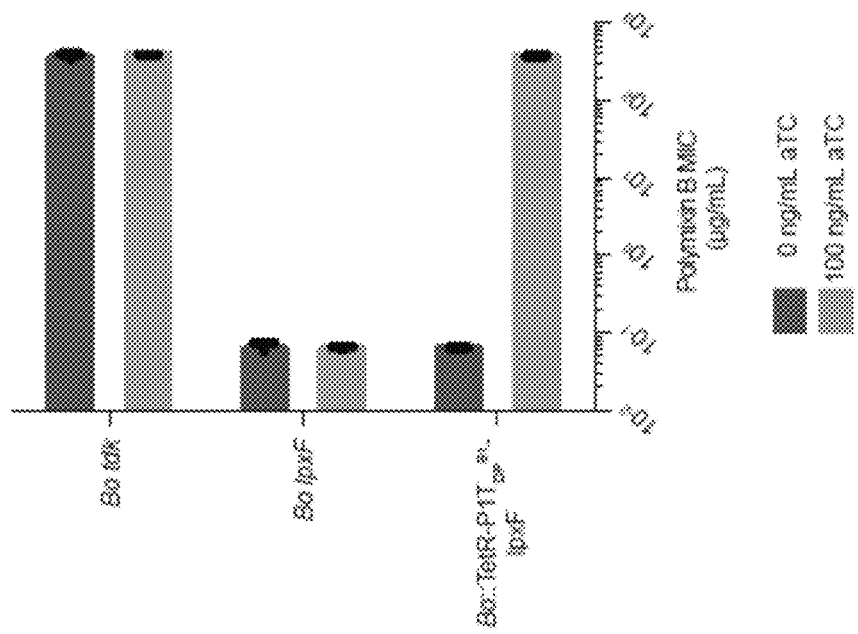
FIG. 10A and FIG. 10B, depicts results from example experiments showing that a self-contained, inducible expression cassette functions to induce PMB resistance to be entirely dependent on aTC.
Figure 10B:
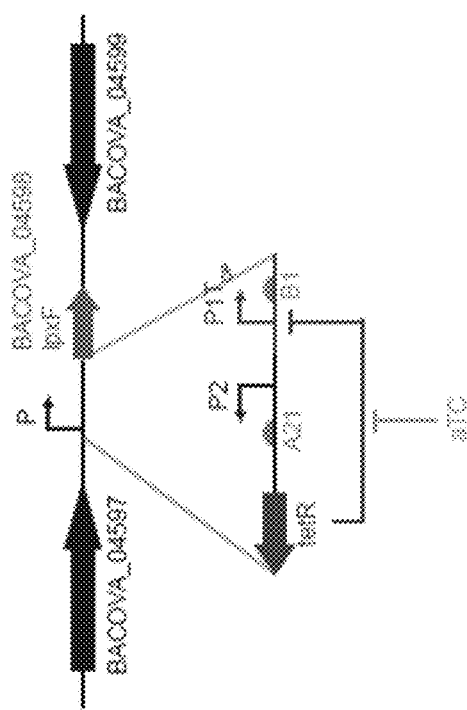

To further test the cross-species performance of TetR-P1T$_{DP}$, this platform was used to acquire regulatory control of an endogenous gene in wildtype *B. ovatus*. To this end, the lpxF homolog in *B. ovatus* was identified (BA-COVA_04598) and the 62 base pairs upstream of this gene were replaced with the TetR-P1T$_{DP}$$^{B1}$ cassette (FIG. 10A). With this one-step promoter replacement, PMB resistance becomes entirely dependent on aTC (FIG. 10B). Together, these results indicate that the key requirements of the P1T$_{DP}$ regulatory system—comprising the P1 and P2 promoters, tetO2 operator sequences, TetR repressor, and responsiveness to aTC—are widely functional across this genus, in both type strains and novel isolates.

Example 8: Control of *B. thetaiotaomicron* Gene Expression in the Mouse Gut

Figure 11:
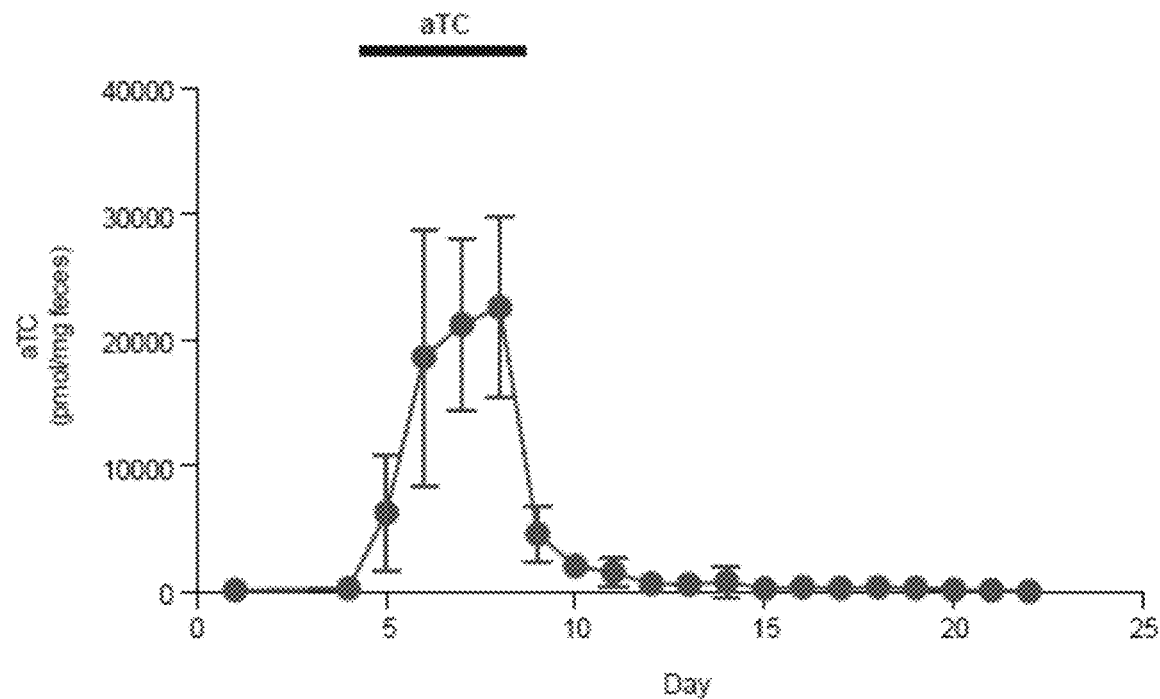
FIG. 11 depicts results from example experiments showing that the inducer is undetectable prior to exogenous addition. Liquid chromatography-mass spectrometry (LC-MS)-based quantification of aTC in fecal pellets reveals that the inducer is undetectable prior to exogenous addition, is readily detected within 24 hours of its addition to drinking water, and is again undetectable 6 days after its removal from the water, exhibiting a half-life of 19 hours in vivo.

A central design element of the P1T$_{DP}$ platform is the use of a synthetic inducer that should be absent from mammalian intestinal tissue and diet. To test this system in vivo, aTC was first introduced at a concentration that does not adversely affect mouse health (100 μg/mL) (Kotula, J. W. et al., 2014, Proceedings of the National Academy of Sciences, 111:4838-4843) for 4 days into the drinking water of gnotobiotic mice carrying wildtype *B. thetaioatomicron*. Liquid chromatography-mass spectrometry (LC-MS)-based quantification of aTC in fecal pellets reveals that the inducer is undetectable prior to exogenous addition, is readily detected within 24 hours of its addition to drinking water, and is again undetectable 6 days after its removal from the water, exhibiting a half-life of 19 hours in vivo (FIG. 11). Germfree mice given the same regime of aTC administration rapidly show comparable aTC levels in fecal pellets (data not shown), indicating that *B. thetaiotaomicron* does not degrade aTC in vivo.

Figures 6A, 6B, 6C, 6D:
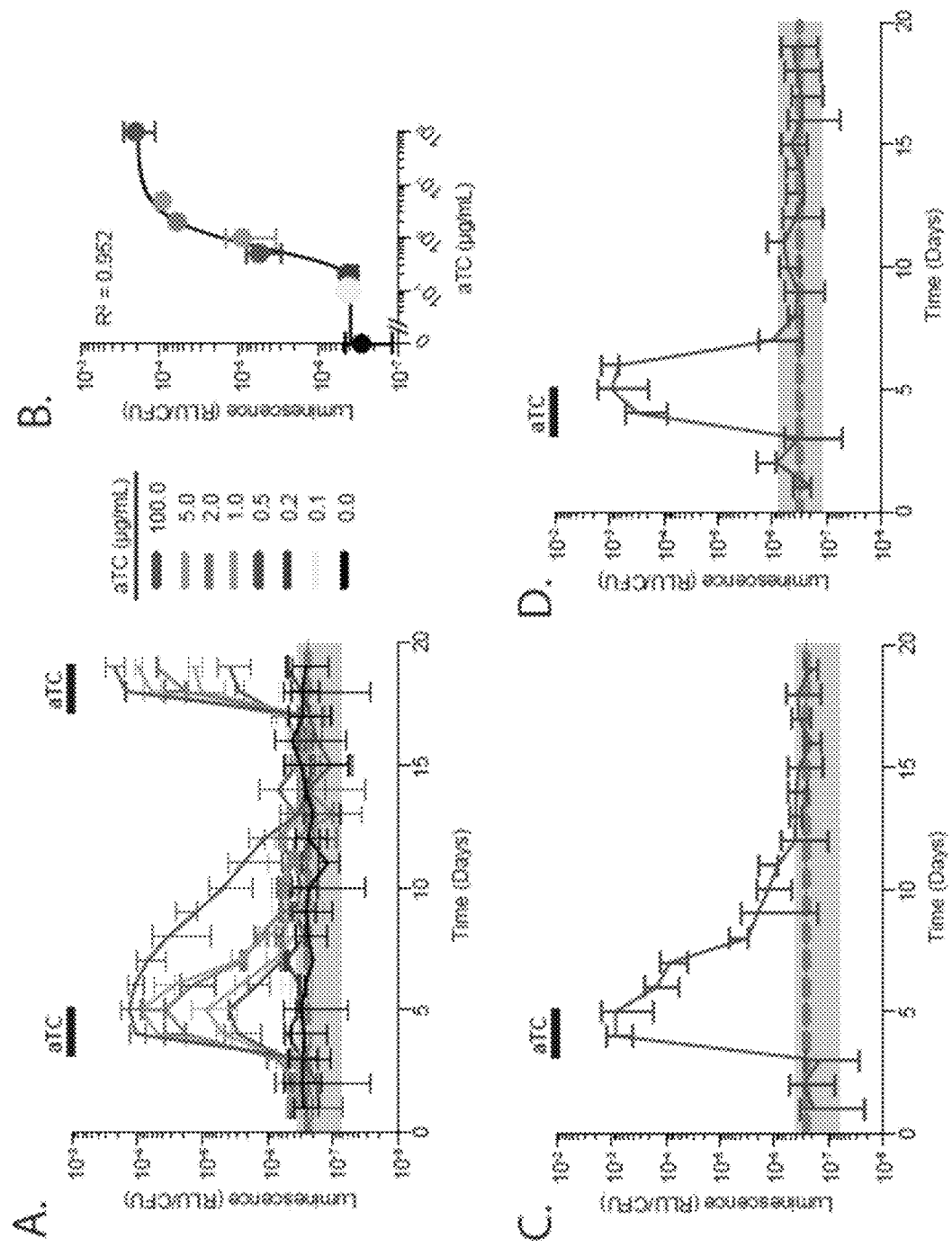
FIG. 6A through FIG. 6D, depicts results from example experiments showing exogenous control of *Bacteroides* gene expression in mice via a synthetic inducer.

To directly test the function of the P1T$_{DP}$ platform in the context of the mammalian gut, groups of germfree mice were colonized with Bt::tetR P1T$_{DP}$$^{GH023}$-NanoLuc. On days 3-5 and 17-19, aTC was added to the drinking water and promoter activity quantified by measuring luminescence in fecal pellets over time and along the length of the gut at day 19. Within 24 hours of aTC addition (the first timepoint after induction), luminescence in fecal pellets increased ~1,000-fold (FIG. 6A, red line). When aTC was removed, luminescence returned to levels observed in fecal pellets of mice colonized with wildtype *B. thetaiotaomicron* (FIG. 6A, grey dashed line and shading), indicating that the promoter returns to a tight OFF state upon inducer removal in vivo (NanoLuc half-life of 3-4 days; complete repression 9 days after aTC removal). The longer half-life of luminescence versus aTC is likely due to the high stability of the engineered Nanoluc protein (Hall, M. P. et al., 2012, ACS Chem. Biol., 7:1848-1857). By contrast, mice colonized with Bt:: tetR P1T$_{DP}$$^{GH023}$-NanoLuc and maintained for the same time period without aTC exhibit no induction of luminescence (FIG. 6A, black line). This engineered system and aTC exposure do not impact *B. thetaiotaomicron* stability in the gut (FIG. 12A), and the kinetics and magnitude of induction are identical each time aTC is provided and are highly reproducible across mice (FIG. 6A). Administration of lower aTC concentrations to mice carrying the reporter strain resulted in the induction of intermediate luminescence measurements within 24 hours, with detectable responses starting at 0.2-0.5 μg/mL aTC (FIG. 6A). The response of P1T$_{DP}$ to aTC inside the gut can be accurately described using a sigmoidal function ($R^2$=0.952) (FIG. 6B), suggesting that 100 μg/mL aTC provides maximal gene induction in vivo. Modulation of gene expression by varying aTC concentrations is recapitulated in the distal small intestine, cecum and throughout the large intestine (FIG. 12B, and FIG. 12C).

Figure 12E:
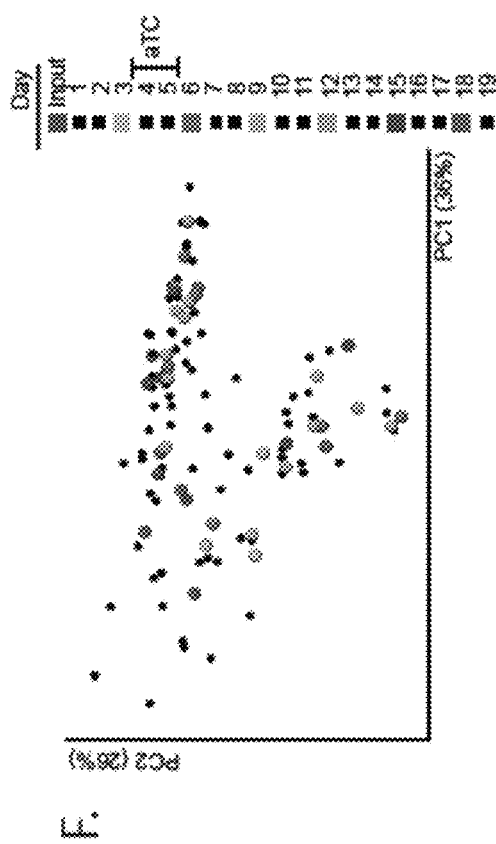
Figure 12F:
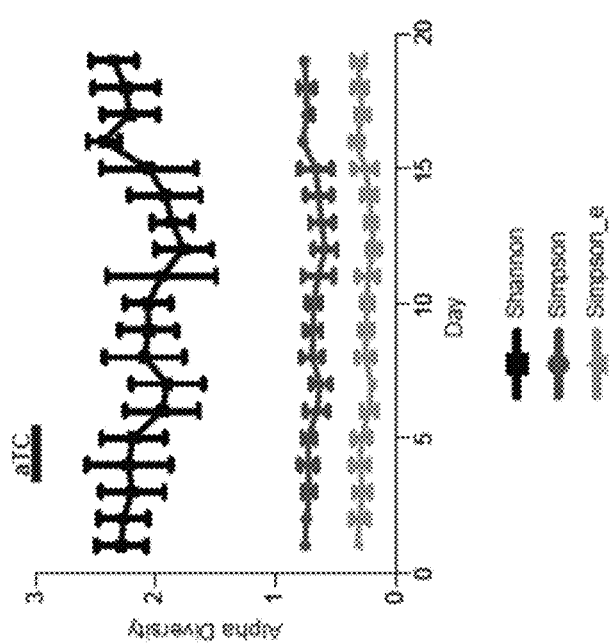
FIG. 12F, depicts results from example experiments showing that the engineered system and aTC exposure do not impact *B. thetaiotaomicron* stability in the gut.

To test the function of P1T$_{DP}$ platform in the context of a complex microbiota, germ-free mice were colonized with a community consisting of Bt::tetR P1T$_{DP}$$^{GH023}$-NanoLuc and 13 additional microbial species representative of the 3 dominant phyla found in the human gut. In this community context, Bt::tetR P1T$_{DP}$$^{GH023}$-NanoLuc represented ~11% of the total community (~3×10$^{11}$ CFU/mL) based on strain- and species-specific qPCR analysis on DNA isolated from fecal pellets and selective culturing (FIG. 12A, and FIG. 12D). Prior to aTC addition (days 1-3), fecal pellets exhibited no induction of luminescence (compared to luminescence measurements from mice monocolonized with wildtype *B. thetaiotaomicron*; FIG. 6C, grey dashed line and shading), indicating that this human community does not produce compounds that activate P1T$_{DP}$. Within 24 hours of administering 100 μg/mL aTC (day 4), luminescence in fecal pellets increased ~4,500-fold, and was stable throughout aTC administration (days 4-5). Fecal luminescence returned to baseline levels after removing the inducer, with complete repression 7-9 days after removal. Alpha and beta diversity analyses of these communities over the 19-day experiment indicate that the presence of aTC did not impact community structure (FIG. 12D, FIG. 12E, FIG. 12F). Additionally, CFU measurements of Bt::tetR P1T$_{DP}$$^{GH023}$-NanoLuc were unchanged throughout the experiment (FIG. 12A), indicating that increases in luminescence are due to in vivo gene modulation in the target organism, not changes in the relative or absolute abundance of this species in the community.

The performance of the $P1T_{DP}$ platform was further interrogated within a complete microbiota. Like most human gut *Bacteroides*, *B. thetaiotaomicron* is rapidly outcompeted in conventional, specific pathogen-free (SPF) wildtype mice that harbor a native murine microbiota. However, this species stably colonizes conventional, SPF $Rag^{-/-}$ animals at ~0.2-0.5% of the total community, similar to its natural abundance in humans (Cullen, T. W. et al., 2015, Science, 347:170-175; Lee, S. M. et al., 2014, Nature, 501:426-429). Conventional $Rag^{-/-}$ mice were gavaged with Bt::tetR $P1T_{DP}^{GH023}$-NanoLuc and aTC administered for 48 hours beginning 3 days after gavage. Luminescence in fecal pellets prior to aTC administration (days 1-3) was similar to that observed in fecal pellets before Bt::tetR $P1T_{DP}^{GH023}$-NanoLuc was introduced, demonstrating tight repression in the absence of aTC (FIG. 6D, grey dashed line and shading). Addition of aTC to the drinking water resulted in a 4,800-fold increase in fecal luminescence which was sustained for the duration of aTC administration and returned to baseline levels 3 days after aTC removal, suggesting that a complete murine microbiota does not produce any inducing molecules, degrade aTC, nor inhibit the ability of the $P1T_{DP}$ platform to activate and repress optimally. Further, aTC does not affect the stability of *B. thetaiotaomicron* in a complete murine microbiota (FIG. 12A). These results demonstrate that the $P1T_{DP}$ platform enables predictable tuning of gene expression within the microbiota in vivo.

Example 9: Inducible Expression Platforms Reveal New Dynamics of Host-Microbiome Interactions To demonstrate the utility of this system, sialic acid (N-acetylneuraminic acid), a sugar liberated from the gut mucosa by sialidases expressed by certain commensal bacteria lacking the necessary enzymes for sialic acid catabolism, was focused on. Free sialic acid is a nutrient source for the antibiotic-associated enteric pathogens *Clostridium difficile* and *Salmonella typhimurium*, and can determine pathogen burden in mouse models (McDonald, N. D. et al., 2016, mBio, 7:e02237-15; Ng, K. M., et al., 2013, Nature, 502:96-99). Mucosal glycoproteins carrying sialic acid also serve as viral receptors (Wasik, B. R. et al., 2016, Trends in Microbiology, 24:991-1001). Despite this broad importance, how commensal sialidase activity determines sialic acid levels in the gut lumen is unexplored. While a healthy microbiota has been reported to produce low levels of free sialic acid, at least one antibiotic formulation alters the community to increase luminal sialic acid concentrations, creating a pathogen-sensitive state (Ng, K. M., et al., 2013, Nature, 502:96-99). It is unknown whether antibiotic-induced sialic acid release reflects a specific reconfiguration of the microbiota dependent on the initial community composition and antibiotics used, or instead is a result of fundamental properties of this microbiome-host interaction.

Figures 13A, 13B, 13C, 13D:
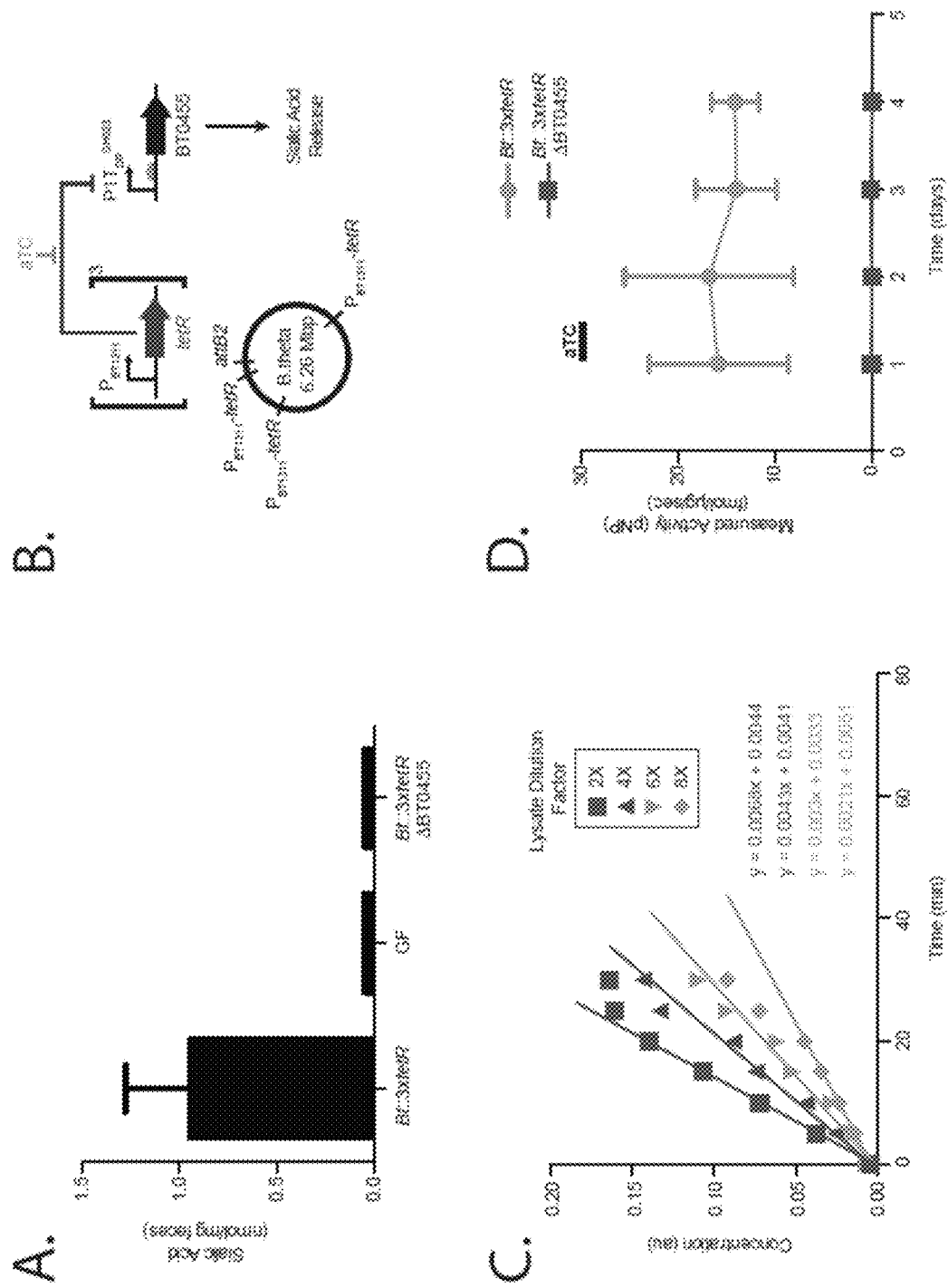
FIG. 13A through FIG. 13F, depicts results from example experiments showing that modulating commensal sialidase expression in mice reveals that sialic acid persists in the gut after microbial enzyme activity is repressed and uncovers a non-linear relationship between enzyme activity and luminal sialic acid.

As previously reported (Ng, K. M., et al., 2013, Nature, 502:96-99), *B. thetaiotaomicron* efficiently liberates sialic acid from the gut mucosa of monoassociated gnotobiotic mice; this activity is dependent on the *B. thetaiotaomicron* sialidase BT0455 (FIG. 13A). To understand how commensal sialidase activity modifies the gut environment, BT0455 was placed under the control of the $P1T_{DP}^{GH023}$ promoter (Bt::3xtetR BT0455 $P1T_{DP}^{GH023}$-BT0455, abbreviated $Bt^{RS}$ for regulated sialidase; FIG. 13B). Germfree mice were colonized with $Bt^{RS}$ (or Bt::3xtetR or Bt::3xtetR BT0455 controls) and fecal samples collected daily before and after 12 hours of aTC induction via drinking water. Quantification of aTC in fecal pellets by LC-MS revealed that inducer levels spike within 12 hours of administration and become undetectable 24 hours later (FIG. 7A).

Figures 13E, 13F:
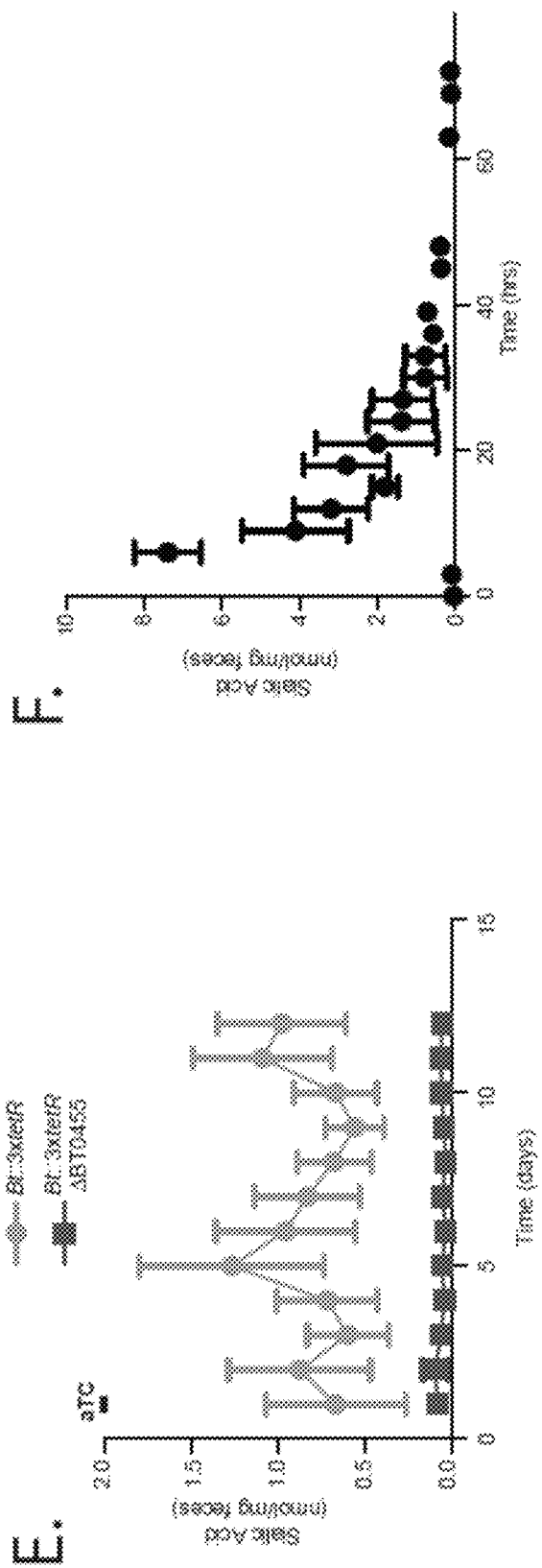

To measure sialidase enzyme activity, cell-free lysates from fecal samples were incubated with the artificial substrate 2-O-(p-Nitrophenyl)-tropheacetylneuraminic acid (pNP-SA), which is hydrolyzed by sialidases, and the subsequent release of the pNP moiety was monitored over time by LC-MS. pNP-SA was provided in 10-fold molar excess to its $K_m$ ($K_m$=0.11 mM) (Park, K. H. et al., 2013, BBA—Proteins and Proteomics, 1834:1510-1519) in order to ensure direct proportionality between the calculated initial reaction velocity and the sialidase concentration in each sample (FIG. 13C). Prior to aTC administration, fecal samples from mice carrying $Bt^{RS}$ show no detectable sialidase activity, indicating tight repression of the enzyme and the absence of pNP in the gut (FIG. 7B and FIG. 13E). After induction, sialidase activity of $Bt^{RS}$-associated mice became equivalent to the control strain expressing BT0455 from its native promoter, suggesting that the $P1T_{DP}$ platform expressed the gene to wildtype levels (FIG. 7B). Sialidase activity was again undetectable 4 days after aTC removal (FIG. 7B). By contrast, fecal samples from control mice monocolonized with wildtype or BT0455 *B. thetaiotaomicron* strains exhibit constitutive or no sialidase activity, respectively (FIG. 13D).

LC-MS/MS was next used to quantify free sialic acid liberated from the host mucosa in the same fecal pellets. Consistent with the ex vivo sialidase activity results, prior to aTC treatment, mice colonized with $Bt^{RS}$ had low levels of fecal sialic acid, equivalent to germfree animals or those colonized with the BT0455 deletion mutant (FIG. 7C, FIG. 13A, and FIG. 13E). After aTC was provided in drinking water, fecal sialic acid levels in $Bt^{RS}$ mice were equivalent to mice colonized with wildtype *B. thetaiotaomicron* (FIG. 7C, FIG. 13A, and FIG. 13E). The inducer was not directly responsible for sialic acid release, because mice colonized with the BT0455 deletion mutant had no increase in fecal sialic acid upon aTC administration (FIG. 13A and FIG. 13E). Strikingly, significant levels of sialic acid persisted in $Bt^{RS}$ animals for multiple days after both inducer and sialidase activity were no longer detectable (FIG. 7C, grey shading). Consistent with this result, exogenous sialic acid delivered by oral gavage to gnotobiotic mice monocolonized with *B. thetaiotaomicron* BT0455 exhibits a half-life of ~9 hours (FIG. 13F). Together, these results indicate that the levels of this microbiome-dependent metabolite reflect not only the current activity of the microbiota, but also its activity from days before.

Figures 7A, 7B, 7C, 7D:
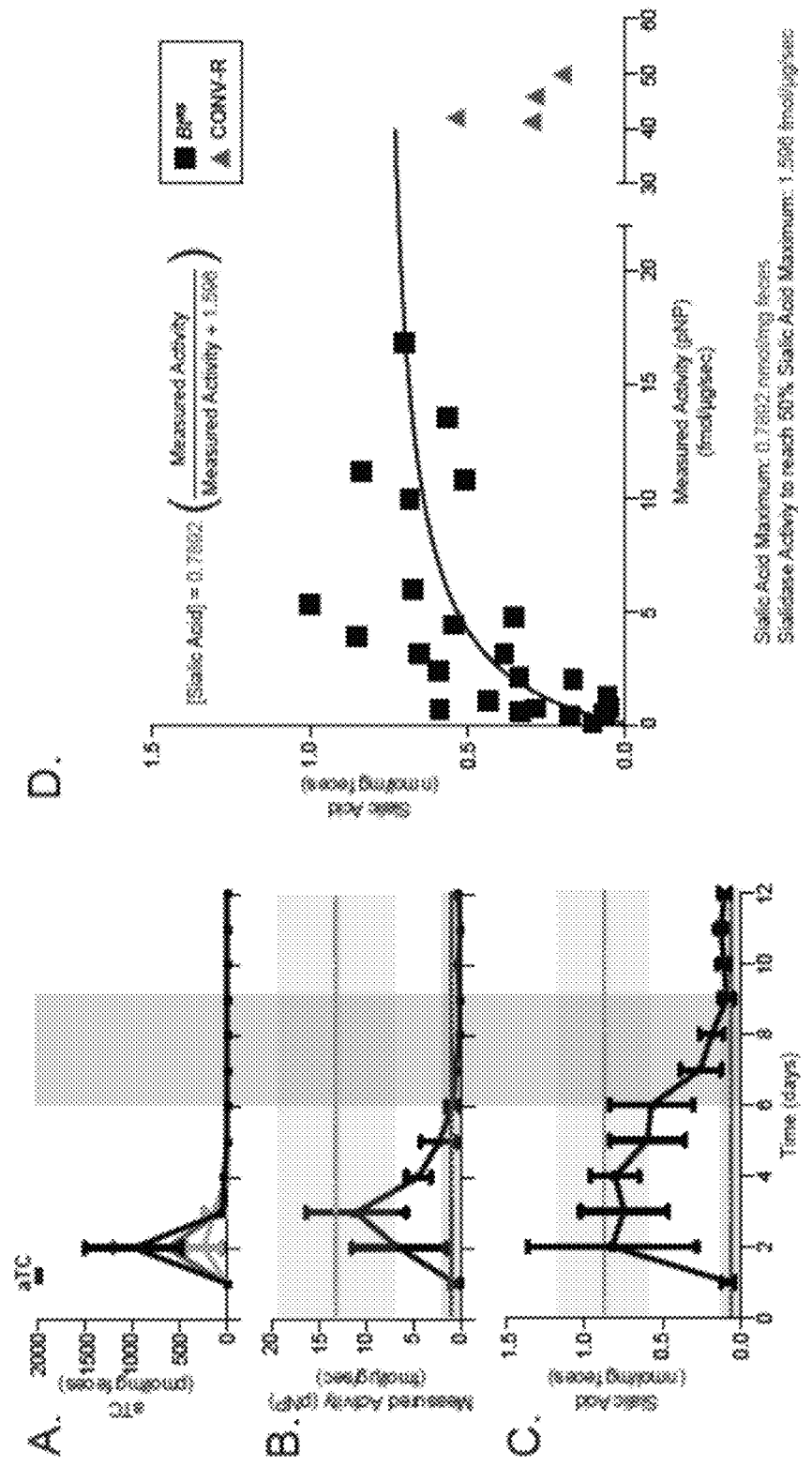
FIG. 7A through FIG. 7D, depicts results from example experiments showing that modulating commensal sialidase expression in mice reveals that sialic acid persists in the gut after microbial enzyme activity is repressed and uncovers a non-linear relationship between enzyme activity and luminal sialic acid.

$Bt^{RS}$ dynamically modulates sialidase expression in response to changing inducer levels, providing the opportunity to compare sialidase activity and fecal sialic acid concentration in vivo as aTC is eliminated from the gut and sialidase gene expression changes accordingly (FIG. 7D). At low levels of sialidase activity, fecal sialic acid scales in proportion to enzyme activity. However, this relationship becomes non-linear once sialidase activity exceeds 25% of the maximum: regardless of sialidase levels, free sialic acid concentration remains constant (FIG. 7D). This suggests that in microbial communities exhibiting at least 25% of the enzyme activity of *B. thetaiotaomicron*, substrate availability (i.e., the host), not community enzyme activity, is the limiting factor that determines free sialic acid levels. Indeed, activity measured in fecal samples from wildtype SPF (conventional) mice reveals high levels of sialidase activity and intermediate levels of free sialic acid, suggesting that the liberation of sialic acid from the mucosa of these animals is substrate (host)-limited and not enzyme-limited. By contrast, catabolism of free sialic acid is likely enzyme (microbe)-limited, as the substrate of this reaction (sialic acid) is readily detectable in SPF animals (FIG. 7D). In this way, these results using precise modulation of a single microbiome-encoded activity in vivo suggest that it is not necessary for antibiotics to reconfigure the microbiota in any specific manner in order to increase free sialic acid levels: instead, even general antibacterial activity can reduce sialic acid catabolism without a proportional impact on the sialic liberation from the host, shifting the community into an increasingly pathogen-sensitive state.

The lack of genetic tools for gut anaerobes and the incompatibility of genetic parts from model organisms are significant obstacles in the microbiome field. Inducible promoters are particularly valuable, because the ability to activate or prevent the expression of target genes over one or more time intervals allows real-time analysis of the contribution of these genes over the course of microbiome establishment, host development, or disease progression (Rogers, J. K. et al., 2015, Nucleic Acids Research, 43:7648-7660). Tightly regulated, highly inducible expression platforms also provide the basis for more complex synthetic architectures.

Herein, a panel of tunable expression platforms that allow *Bacteroides* gene expression to be strictly controlled by the presence of a synthetic inducer not found in bacterial growth media, mouse intestines or diets, or the human and mouse microbial communities tested in this study were developed. In the absence of inducer, gene expression is repressed to levels that recapitulate the phenotypes of strains lacking the target gene. When aTC is provided, individual promoters within this panel exhibit up to a $10^4$-fold dynamic range of expression, and promoter activity across the panel ranges $3 \times 10^5$-fold. This dynamic control of gene repression and expression are recapitulated or even exceeded in mice, and investigation of sialic acid provides a first example of insights gained from manipulating a host-microbe interaction by tuning expression of a single gene in the microbiome.

Variations in TetR-regulated promoters expand the versatility, range, and regulatory properties of this system (Bertram, R. et al., 2008, Microbial Biotechnology, 1:2-16; Hillen, W. et al., 1994, Annu. Rev. Microbiol., 48:345-369). For example, modifications of TetR have been identified that alter its specificity for tetracycline analogs (Henssler, E.-M. et al., 2004, Biochemistry, 43:9512-9518; Scholz, O. et al., 2003, Journal of Molecular Biology, 329:217-227), change its allosteric interactions so that aTC acts as a corepressor (Kamionka, A. et al., 2004, Nucleic Acids Research, 32:842-847; Scholz, O. et al., 2004, Mol. Microbiol., 53:777-789), or change its operator specificity to selectively recognize distinct tetO variants (Helbl, V. et al., 1998, Journal of Molecular Biology, 276:313-318; Helbl, V. et al., 1998, Journal of Molecular Biology, 276:319-324; Krueger, M. et al., 2007, Gene, 404:93-100). These modifications considerably expand the range of conceivable applications of TetR-regulated systems and increase the possibilities for multi-gene regulation within *Bacteroides*.

The absence of aTC or related molecules in mice, their diets, or the microbial community allows precise control of *Bacteroides* gene expression in vivo, potentially enabling on-demand delivery of therapeutic compounds. The tetracycline analog doxycycline is highly stable and binds tightly to TetR, and has been administered to mice for several months at a time (Bohl, D. et al., 1998, Blood, 92:1512-1517; Manfredsson, F. P. et al., 2009, Molecular Therapy, 17:1857-1867). The use of tetracycline analogs that differ in stability and sensitivity to host metabolism, bioavailability and excretion will increase the options for fine temporal control in microbiome studies. Additionally, administering inducers through different routes (orally via water, diet, or time- or pH-dependent delayed release capsules (Cetin, M. et al., 2011, Pharmaceutical Development and Technology, 18:570-576); via enema; or surgically through catheterization of specific locations in the GI tract) will allow additional means to precisely tune gene expression in a spatially restricted manner. Lastly, the use of a synthetic inducer to alter gene expression will enable functional and kinetic studies of the microbiome in a matter that does not itself perturb the dynamics of microbial metabolism, growth, and community composition as could be anticipated from the administration of dietary polysaccharides or sugars. Further, changes in host diet and its component polysaccharides are unlikely to impact reporter function.

Figure 14:
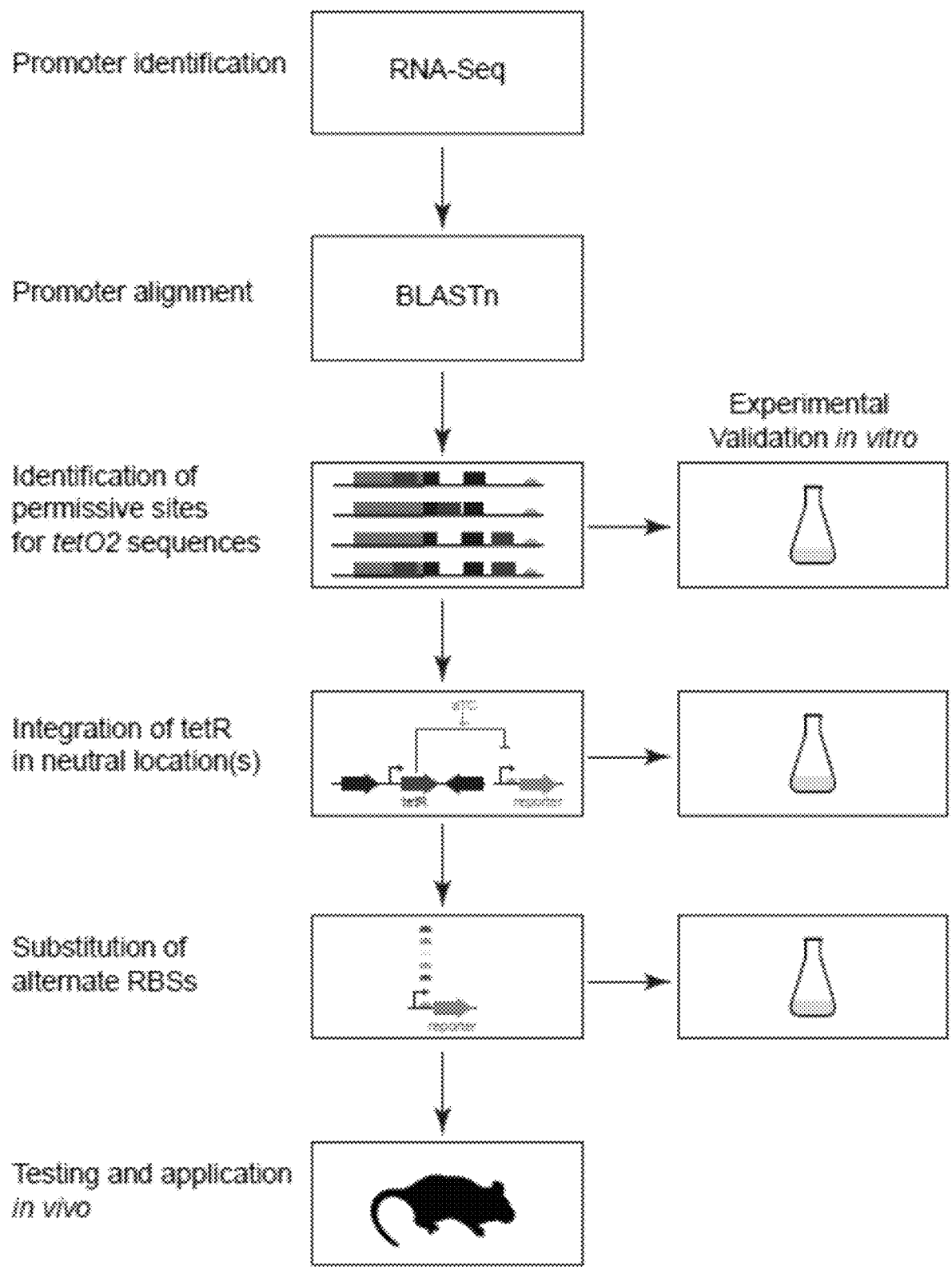
FIG. 14 depicts a diagram of the regulated expression platform, which was designed using general principles that apply across the microbiome.
Figure 15:
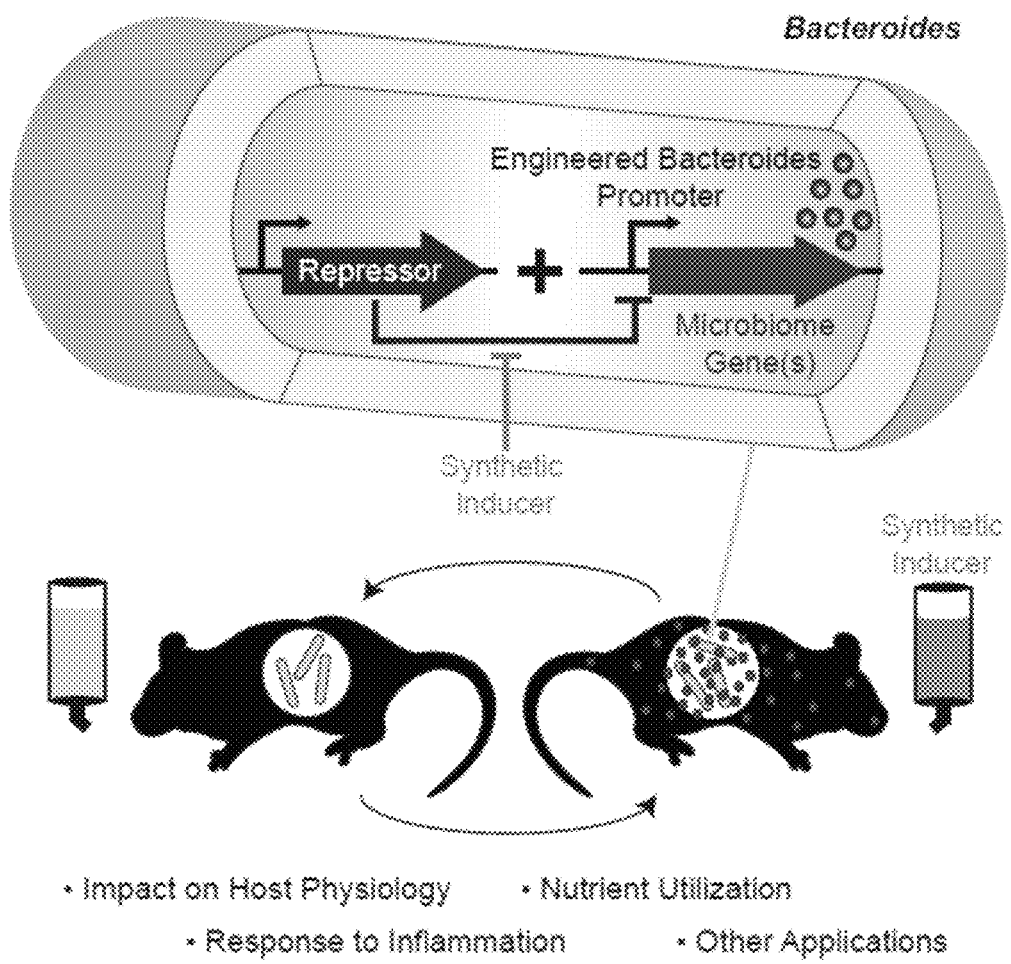
FIG. 15 depicts a diagram of the regulated expression platform in *Bacteroides*. This system can be utilized to have an impact on host physiology, including nutrient utilization, responses to inflammation, and other applications.

This regulated expression platform was designed using general principles that should apply across the microbiome (FIG. 14), and provides a route for regulated gene expression in other prominent genera from the human gut microbiome and in microbes that inhabit other body regions or habitats. These genetic platforms could potentially be combined with important recent developments (Kotula, J. W. et al., 2014, Proceedings of the National Academy of Sciences, 111:4838-4843; Mimee, M. et al., 2015, Cell Systems, 1:62-71) and will enable progress in understanding the biochemical and ecological processes that contribute to the homeostasis of the intestinal microbiome and its impact on host health and disease.

Example 10: Inducible Expression Platforms Reveal New Dynamics of Host-Microbiome Interactions This invention also enables a novel approach for genome engineering. This novel approach allows precise, markerless genome editing of wildtype bacteria directly isolated from humans, and unlike currently available methods, does not require any prior genetic manipulation.

Current methods for performing deletions in *Bacteroides* involve counterselection strategies that utilize genes that are lethal to the host strain under specific conditions. These include using the thymidine kinase gene (tdk) which is sensitive to 5-fluoro-2'-deoxyuridine (FUDR) or thymidylate synthetase gene (thyA) that is sensitive to trimethoprim. Both of these strategies require the host to have mutations in either of the genes (tdk, thyA) used for counterselection and that these mutants show sensitivity to FUDR or trimethoprim. Another strategy shown to be an option for counterselection in *Bacteroides fragilis* and *Bacteroides thetaiotaomicron* utilizes a mutated pheS* (the a-subunit of phenylalanyl tRNA synthase) which causes toxicity in the presence of p-chloro-phenylalanine (p-Cl-phe). However, production of pheS* has not worked in rich media, requiring that the species be culturable in minimal defined media. Thus the limitations to this approach include host strain susceptibility to mutant pheS*, and limited growth media conditions. Out of all the reported strategies, there exists no method for genetic deletions in *Bacteroides* that allow for deletions in wild-type host strains with a broadly applicable counter-selection method that could be used in not only type strains but also wild or clinical isolates of *Bacteroides* sp.

The tunable expression platform described in this invention allows for strictly controlled gene expression of *Bacteroides* species in the presence of a synthetic inducer aTC. It was shown that this expression platform can be coupled to expression of toxic effectors from the *Bacteroides* Type VI secretion system (or other toxic proteins). These effectors are highly toxic to bacterial species that do not express immunity genes to combat the effector toxicity. It was shown that expression of two of these effectors (Bte1 and Bfe1), both encoded by *B. fragilis* strains NCTC 9343 and 638R, respectively, remain tightly controlled in the engineered expression system. In the absence of the inducer, aTC, these lethal genes are not expressed allowing normal growth of *Bacteroides* sp. containing a plasmid with the inducible promoter driving expression of these effectors. In the presence of aTC, toxicity is apparent through immediate decrease in cell viability.

Figure 16:
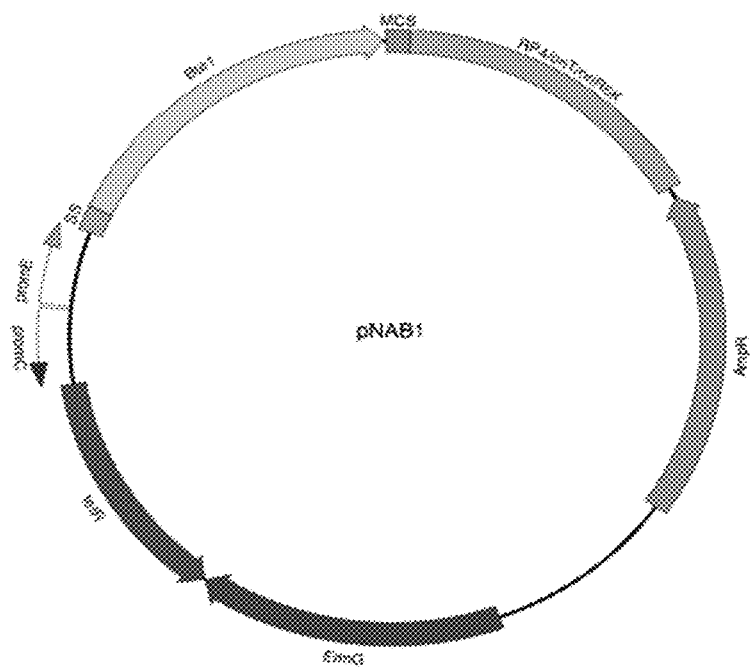
FIG. 16 depicts diagrams of pNAB1 and pNAB2. pNAB1 and pNAB2 include a constitutive promoter (promC) driving expression of the repressor tetR and an engineered promoter (P1T$_{DP}$) driving expression of either one toxic effector (pNAB1 utilizing Bte1) or two toxic effectors (pNAB2 utilizing Bte1 and Bfe1). These toxic effectors can be readily substituted for any effector secreted by the Type VI secretion system in *Bacteroides* or other organisms, bacteriocins, or other toxic proteins. The RBS for the engineered promoter (P1T$_{DP}$) can be substituted for any of the ones described in this invention to control the promoter strength. The constitutive promoter (promC) is interchangeable with other constitutive promoters.
Figure 16:
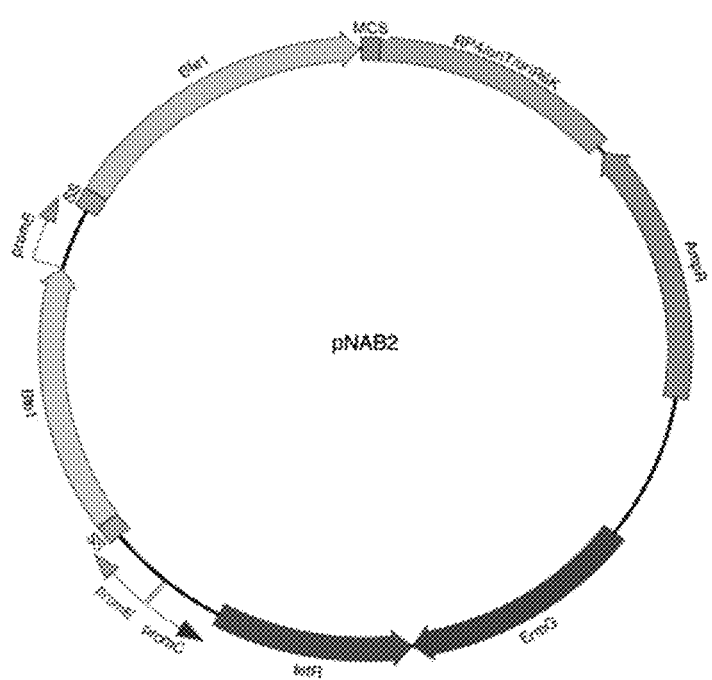

Taking advantage of the tightly controlled inducible promoter and the strength of these toxic effectors, non-replicating (suicide) plasmids were built with the following components: one or two toxic effectors under the control of the aTC inducible promoter system; a constitutively expressed gene encoding the TetR repressor; a multiple cloning site for introduction of target alleles (for deletion, insertion, or modification of nucleotide sequences); selectable markers for *E. coli* and *Bacteroides*. The number and choice of effectors (including any effector secreted by the Type VI secretion system in *Bacteroides* or other organisms, bacteriocins, or other toxic proteins) can be readily substituted as part of the invention. These plasmids, pNAB1 and pNAB2, are capable of inserting into a target genetic site by homologous recombination with the target allele in the plasmid. Because aTC is absent, no toxicity is observed. Upon introduction of the inducer, aTC, these plasmids express the toxic effectors and only those cells that have undergone a second homologous recombination (to create a mutant or revertant) remain. In contrast to the TDK approach, (1) the host *Bacteroides* strain does not need to be modified in any way (e.g., the strain does not need to a tdk or other mutant), (2) the toxic effectors are highly potent toxins that show broad toxicity across species, (3) the suicide plasmid is highly modular and with multiple effectors available in the Type VI secretion system different effectors could be substituted based on their effectiveness in the target bacteria of interest. In addition, the presence of 2 effectors in pNAB2 circumvents mutations to disrupt their toxicity. Plasmid maps of pNAB1 and pNAB2 are shown in FIG. 16.

The utility of this system is demonstrated in multiple proof-of-principle studies in wild-type strains of *Bacteroides thetaiotaomicron* and *Bacteroides vulgatus*. This is a novel strategy as markerless deletions in wild type *Bacteroides* sp. in rich media has not been done before and genetic modification of wild type *Bacteroides vulgatus* has never been reported. As a proof of principle, the gene lpxF which is responsible for resistance of *Bacteroides thetaiotaomicron* to the antimicrobial peptide Polymyxin B (PMB) was deleted from wildtype *B. theta* with both pNAB1 and pNAB2. Deletions were confirmed by PCR and mutants also exhibited loss of PMB resistance when grown on plates with PMB.

Figure 17:
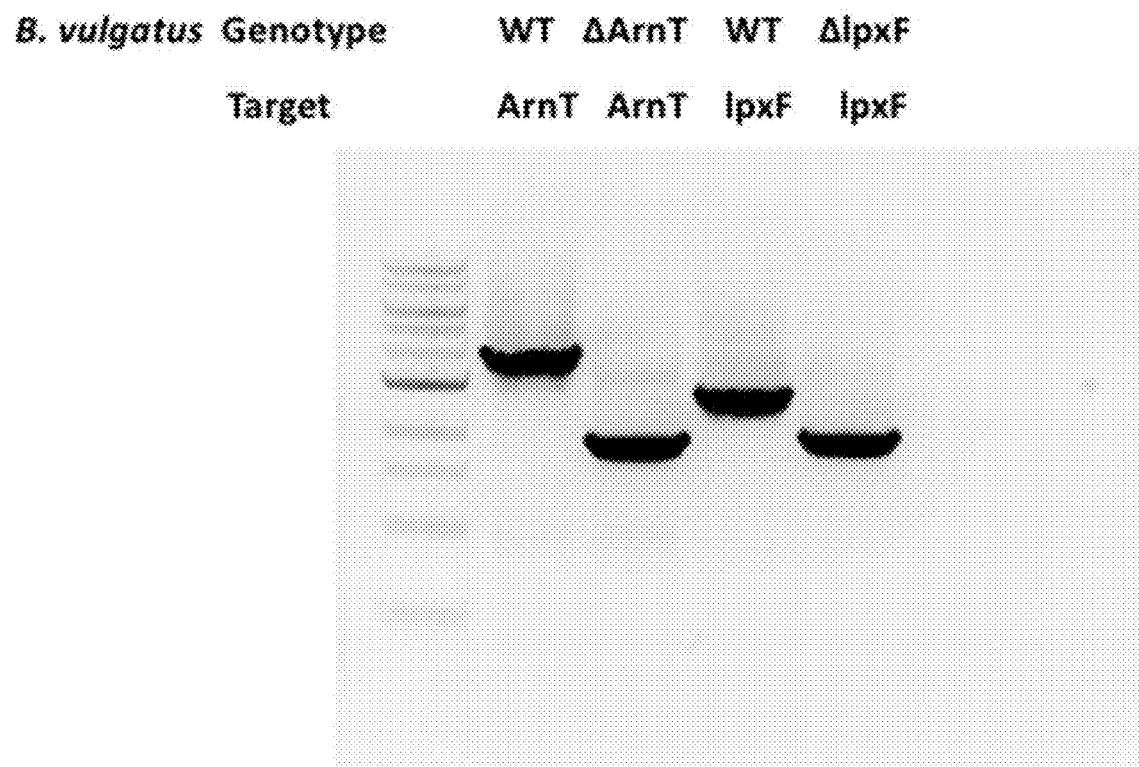
FIG. 17 depicts the results from example experiments demonstrating PCR confirmation of deletions of two independent genes in WT *Bacteroides vulgatus* ATCC 8482 using pNAB2 deletion system. Primers were located outside of the regions used for the allelic exchange. Presence of ArnT gene (Bvu_1068) produces an amplicon of 3533 bp, while the deletion mutant (ΔBvu_1068) amplicon size is 1808 bp reflecting deletion of ArnT gene size 1725 bp. Presence of lpxF gene (Bvu_3293) produces an amplicon of 2615 bp, while the deletion mutant (ΔBvu_3293) amplicon size is 1907 bp reflecting deletion of lpxF gene size 708 bp.

As a second proof of principle, the lpxF homolog was deleted and also the arnT homolog from *Bacteroides vulgatus* using pNAB2 (FIG. 17). These experiments have shown deletions of two separate genes in two independent *Bacteroides* species using this invention.

This system provides a much needed tool in *Bacteroides* genetics. The field has been very limited in its ability to perform genetics with wild type species due to limitations in deletion strategies. This deletion strategy provides a broadly applicable, tightly controlled system that would allow for genetic deletions in *Bacteroides* sp., including direct isolates from humans or other animals, that previously had no method for obtaining such mutants. The ability to work in wild type species instead of a mutant host bacteria eliminates any consequences known or unknown to having the host previously modified. By contrast, the TDK and other systems require the use of a genetically modified parent strain, which adds a difficult engineering step; further, studies of the modified parent strain are compromised by the TDK or other deletion that impacts other aspects of bacterial biology. The future implications of this system include the ability to perform deletions in a wide variety of *Bacteroides* sp. but also the ability to study genetics in wild isolates or clinical isolates in which very little is known. It will help provide insight into properties of clinical isolates that are not able to be studied in lab adapted strains.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A nucleic acid molecule comprising an inducible synthetic promoter variant of a *Bacteroides* 16S ribosomal DNA (rDNA) promoter, wherein the inducible synthetic promoter comprises the nucleotide sequence selected from the group consisting of SEQ ID NO: 12, SEQ ID NO: 13, SEQ ID NO: 14, SEQ ID NO: 15, SEQ ID NO: 24, SEQ ID NO: 25, SEQ ID NO: 26, SEQ ID NO: 27, SEQ ID NO: 28, and SEQ ID NO: 29.

2. The nucleic acid molecule of claim 1, wherein the inducible synthetic promoter further comprises an element selected from the group consisting of one or more repressor response element, a ribosomal binding site (RBS), and a combination thereof.

3. The nucleic acid molecule of claim 2, wherein the synthetic promoter further comprises at least one tetO2 repressor response element comprising the nucleotide sequence as set forth in SEQ ID NO:11.

4. The nucleic acid molecule of claim 2, wherein the RBS comprises the nucleotide sequence selected from the group consisting of SEQ ID NO:9, SEQ ID NO:18, SEQ ID NO:19, SEQ ID NO:20, SEQ ID NO:21, SEQ ID NO:22 and SEQ ID NO:23.

5. The nucleic acid molecule of claim 1, wherein the inducible synthetic promoter is operably linked to a coding region.

6. The isolated nucleic acid molecule of claim 5, wherein the coding region encodes at least one selected from the group consisting of a therapeutic RNA, a therapeutic peptide, a protein, and a toxic protein.

7. The nucleic acid molecule of claim 1 comprising an expression cassette comprising the inducible synthetic promoter variant of the *Bacteroides* 16S rDNA promoter.

8. The expression cassette of claim 7, wherein the inducible synthetic promoter comprises one or more repressor response elements, and further wherein the expression cassette comprises a nucleotide sequence encoding a repressor.

9. A cell modified for inducible gene expression comprising the nucleic acid molecule of claim 1.

10. The cell of claim 9, wherein the inducible synthetic promoter comprises one or more repressor response elements, and further wherein the cell is modified to express a repressor.

11. A method of inducing gene expression in a cell, comprising contacting the cell of claim 9 with an inducer.

12. The method of claim 11, wherein the inducible synthetic promoter further comprises one or more repressor response elements, and further wherein the cell is modified to express a repressor, thereby inhibiting expression of the coding region in the absence of the inducer, and further wherein the inducer inhibits the activity of the repressor, thereby inducing expression of the coding region.

13. The method of claim 12, wherein the inducible synthetic promoter further comprises at least one tetO2 repressor response element comprising the nucleotide sequence as set forth in SEQ ID NO:11.

* * * * *